United States Patent
Maloney et al.

(10) Patent No.: US 10,266,488 B2
(45) Date of Patent: Apr. 23, 2019

(54) 4-((2-HYDROXY-3-METHOXYBENZYL)AMINO)BENZENESULFONAMIDE DERIVATIVES AS POTENT AND SELECTIVE INHIBITORS OF 12-LIPOXYGENASE

(71) Applicants: Eastern Virginia Medical School, Norfolk, VA (US); THE REGENTS OF THE UNIVERSITY OF CALIFORNIA, SANTA CRUZ, Oakland, CA (US); THE UNITED STATES OF AMERICA DEPARTMENT OF HEALTH AND HUMAN SERVICES, Bethesda, MD (US); Thomas Jefferson University, Philadelphia, PA (US)

(72) Inventors: David J. Maloney, Point Of Rocks, MD (US); Diane K. Luci, Germantown, MD (US); Ajit Jadhav, Chantilly, VA (US); Theodore Holman, Santa Cruz, CA (US); Jerry L. Nadler, Norfolk, VA (US); Michael Holinstat, Wallingford, PA (US); David Taylor-Fishwick, Norfolk, VA (US); Anton Simeonov, Bethesda, MD (US); Adam Yasgar, Washington, DC (US); Steven McKenzie, Springfield, PA (US)

(73) Assignees: Eastern Virginia Medical School, Norfolk, VA (US); The Regents of the University of California Santa Cruz, Santa Cruz, CA (US); The United States of America Department of Health and Human Services, Washington, DC (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/028,386

(22) PCT Filed: Oct. 10, 2014

(86) PCT No.: PCT/US2014/060174
§ 371 (c)(1),
(2) Date: Apr. 8, 2016

(87) PCT Pub. No.: WO2015/054662
PCT Pub. Date: Apr. 16, 2015

(65) Prior Publication Data
US 2017/0001955 A1 Jan. 5, 2017

Related U.S. Application Data

(60) Provisional application No. 61/987,129, filed on May 1, 2014, provisional application No. 61/889,396, filed on Oct. 10, 2013.

(51) Int. Cl.
C07D 277/82 (2006.01)
C07D 235/30 (2006.01)
(Continued)

(52) U.S. Cl.
CPC ............. *C07C 311/44* (2013.01); *A61P 7/02* (2018.01); *C07D 211/28* (2013.01);
(Continued)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,089,809 A | 5/1978 | Farrior, Jr. | |

(Continued)

FOREIGN PATENT DOCUMENTS

| | | |
|---|---|---|
| AU | 2011244937 | 11/2011 |
| AU | 2013202912 | 5/2013 |

(Continued)

OTHER PUBLICATIONS

PubChem: Compound ML355; CID 70701426. Electronic Resource. Retrieved online on Feb. 14, 2017: [https://pubchem.ncbi.nlm.nih.gov/compound/70701426].*

(Continued)

*Primary Examiner* — Anna Pagonakis
(74) *Attorney, Agent, or Firm* — Wilmer Cutler Pickering Hale and Dorr LLP

(57) ABSTRACT

Human lipoxygenases (LOXs) are a family of iron-containing enzymes involved in catalyzing the oxidation of polyunsaturated fatty acids to provide the corresponding bioactive hydroxyeicosatetraenoic acid (HETE) metabolites. These eicosanoid signaling molecules are involved in a (Continued)

number of physiologic responses such as platelet aggregation, inflammation, and cell proliferation. Platelet-type 12-(S)-LOX (12-LOX) is of particular interest because of its demonstrated role in skin diseases, diabetes, platelet hemostasis, thrombosis, and cancer. Disclosed herein is the identification and medicinal chemistry optimization of a 4-((2-hydroxy-3-methoxybenzyl)amino)benzenesulfonamide-based scaffold. The compounds display nM potency against 12-LOX and excellent selectivity over related lipoxygenases and cyclooxygenases. In addition to possessing favorable ADME properties, the compounds also inhibit PAR-4 induced aggregation and calcium mobilization in human platelets, and reduce 12-HETE in mouse/human beta cells. The compounds can also be used in methods for treating or preventing a 12-lipoxygenase mediated disease or disorder.

9 Claims, 23 Drawing Sheets

(51) Int. Cl.
| | |
|---|---|
| C07D 263/58 | (2006.01) |
| C07C 311/44 | (2006.01) |
| A61P 7/02 | (2006.01) |
| C07D 277/52 | (2006.01) |
| C07D 211/28 | (2006.01) |
| C07D 213/76 | (2006.01) |
| C07D 217/02 | (2006.01) |
| C07D 217/22 | (2006.01) |
| C07D 239/69 | (2006.01) |
| C07D 261/16 | (2006.01) |
| C07D 295/135 | (2006.01) |
| C07D 333/36 | (2006.01) |
| C07D 417/12 | (2006.01) |

(52) U.S. Cl.
CPC ......... *C07D 213/76* (2013.01); *C07D 217/02* (2013.01); *C07D 217/22* (2013.01); *C07D 235/30* (2013.01); *C07D 239/69* (2013.01); *C07D 261/16* (2013.01); *C07D 263/58* (2013.01); *C07D 277/52* (2013.01); *C07D 277/82* (2013.01); *C07D 295/135* (2013.01); *C07D 333/36* (2013.01); *C07D 417/12* (2013.01)

(56) References Cited

U.S. PATENT DOCUMENTS

| | | |
|---|---|---|
| 4,233,871 A | 11/1980 | Alessi |
| 4,438,052 A | 3/1984 | Weder et al. |
| 4,438,253 A | 3/1984 | Casey et al. |
| 4,485,054 A | 11/1984 | Mezei et al. |
| 4,532,089 A | 7/1985 | MacDonald |
| 4,605,669 A | 8/1986 | Summers, Jr. |
| 4,623,661 A | 11/1986 | Summers, Jr. |
| 4,652,441 A | 3/1987 | Okada et al. |
| 4,761,403 A | 8/1988 | Gunn et al. |
| 4,822,811 A | 4/1989 | Summers |
| 4,897,269 A | 1/1990 | Mezei |
| 4,897,422 A | 1/1990 | Summers, Jr. |
| 5,100,669 A | 3/1992 | Hyon et al. |
| 5,112,848 A | 5/1992 | Brooks et al. |
| 5,120,752 A | 6/1992 | Brooks et al. |
| 5,571,821 A | 11/1996 | Chan et al. |
| 5,574,062 A | 11/1996 | Hashimoto et al. |
| 5,665,428 A | 9/1997 | Cha et al. |
| 5,710,171 A | 1/1998 | Dinsmore et al. |
| 5,770,222 A | 6/1998 | Unger et al. |
| 5,795,855 A | 8/1998 | Schneider et al. |
| 5,820,880 A | 10/1998 | Alving et al. |
| 5,919,792 A | 7/1999 | Duggan et al. |
| 6,140,351 A | 10/2000 | Arnaiz et al. |
| 6,217,875 B1 | 4/2001 | Murai et al. |
| 6,225,329 B1 | 5/2001 | Richter et al. |
| 6,262,112 B1 | 7/2001 | Mittendorf et al. |
| 6,287,588 B1 | 9/2001 | Shih et al. |
| 6,391,568 B1 | 5/2002 | Schneider et al. |
| 6,498,185 B1 | 12/2002 | Arnaiz et al. |
| 6,573,278 B2 | 6/2003 | Mittendorf et al. |
| 6,586,475 B1 | 7/2003 | Kato et al. |
| 6,632,815 B2 | 10/2003 | Zhu et al. |
| 6,670,364 B2 | 12/2003 | Laborde et al. |
| 6,686,368 B1 | 2/2004 | Zhu et al. |
| 6,720,317 B1 | 4/2004 | Zhu et al. |
| 6,747,002 B2 | 6/2004 | Cheung et al. |
| 6,767,909 B2 | 7/2004 | Joutsamo et al. |
| 6,831,175 B2 | 12/2004 | Li et al. |
| 6,953,857 B2 | 10/2005 | Nazare et al. |
| 7,011,938 B2 | 3/2006 | Macey |
| 7,015,227 B2 | 3/2006 | Darrow et al. |
| 7,015,233 B2 | 3/2006 | Gomtsyan et al. |
| 7,030,286 B2 | 4/2006 | Rottger et al. |
| 7,067,665 B2 | 6/2006 | Nazare et al. |
| 7,179,946 B2 | 2/2007 | Scholz et al. |
| 7,253,171 B2 | 8/2007 | Jimenez Mayorga et al. |
| 7,265,122 B2 | 9/2007 | Wu et al. |
| 7,285,565 B2 | 10/2007 | Zhu et al. |
| 7,320,989 B2 | 1/2008 | Anderson et al. |
| 7,326,795 B2 | 2/2008 | Sudhakar et al. |
| 7,335,792 B2 | 2/2008 | Mortimore et al. |
| 7,351,434 B2 | 4/2008 | Chern et al. |
| 7,375,126 B2 | 5/2008 | Gomtsyan et al. |
| 7,384,967 B2 | 6/2008 | Polisetti et al. |
| 7,482,488 B2 | 1/2009 | Reddy et al. |
| 7,541,373 B2 | 6/2009 | Polisetti et al. |
| 7,541,485 B2 | 6/2009 | Michalak et al. |
| 7,582,665 B2 | 9/2009 | Takemoto et al. |
| 7,612,114 B2 | 11/2009 | Hamaoka et al. |
| 7,642,272 B2 | 1/2010 | Shankar et al. |
| 7,671,063 B2 | 3/2010 | Baenteli et al. |
| 7,671,077 B2 | 3/2010 | Lin |
| 7,749,999 B2 | 7/2010 | Boman et al. |
| 7,786,125 B2 | 8/2010 | Lin |
| 7,790,883 B2 | 9/2010 | Butters et al. |
| 7,795,242 B2 | 9/2010 | Van Rhijn et al. |
| 7,803,804 B2 | 9/2010 | Collingwood et al. |
| 7,897,599 B2 | 3/2011 | Boman et al. |
| 7,897,628 B2 | 3/2011 | Polisetti et al. |
| 7,919,617 B2 | 4/2011 | Boman et al. |
| 7,928,111 B2 | 4/2011 | Tachdjian et al. |
| 7,960,412 B2 | 6/2011 | Hamaoka et al. |
| 8,026,256 B2 | 9/2011 | Gomtsyan et al. |
| 8,063,081 B2 | 11/2011 | Polisetti et al. |
| 8,071,762 B2 | 12/2011 | Gomtsyan et al. |
| 8,129,357 B2 | 3/2012 | Chern et al. |
| 8,188,290 B2 | 5/2012 | Bientinesi et al. |
| 8,283,356 B2 | 10/2012 | Baenteli et al. |
| 8,399,520 B2 | 3/2013 | Hamaoka et al. |
| 8,404,724 B2 | 3/2013 | Sinha et al. |
| 8,420,678 B2 | 4/2013 | Mahadevan et al. |
| 8,487,116 B2 | 7/2013 | Gomtsyan et al. |
| 8,603,751 B2 | 12/2013 | Steyn et al. |
| 8,633,186 B2 | 1/2014 | Tachdjian et al. |
| 8,703,749 B2 | 4/2014 | Testi et al. |
| 8,815,924 B2 | 8/2014 | Dorsch et al. |
| 8,846,351 B2 | 9/2014 | Quinlan et al. |
| 8,895,608 B2 | 11/2014 | Iadonato et al. |
| 8,933,130 B2 | 1/2015 | Lyttle et al. |
| 8,940,900 B2 | 1/2015 | Mookhtiar et al. |
| 8,962,663 B2 | 2/2015 | Mahadevan et al. |
| 8,993,622 B2 | 3/2015 | Wadell et al. |
| 9,115,122 B2 | 8/2015 | Shapiro et al. |
| RE45,670 E | 9/2015 | Polisetti et al. |
| 9,144,557 B2 | 9/2015 | Zhi et al. |
| 9,249,087 B2 | 2/2016 | Kozikowski et al. |
| 2002/0002183 A1 | 1/2002 | Zhu et al. |
| 2002/0072529 A1 | 6/2002 | Mittendorf et al. |
| 2002/0091116 A1 | 7/2002 | Zhu et al. |
| 2002/0127605 A1 | 9/2002 | Hamilton et al. |

(56) References Cited

U.S. PATENT DOCUMENTS

| | | |
|---|---|---|
| 2002/0198195 A1 | 12/2002 | Nazare et al. |
| 2003/0162993 A1 | 8/2003 | Mortimore et al. |
| 2003/0187026 A1 | 10/2003 | Li et al. |
| 2003/0199511 A1 | 10/2003 | Li et al. |
| 2004/0053927 A1 | 3/2004 | Darrow et al. |
| 2004/0059170 A1 | 3/2004 | Rottger et al. |
| 2004/0116399 A1 | 6/2004 | Zhu et al. |
| 2004/0122235 A1 | 6/2004 | Polisetti et al. |
| 2004/0142982 A1 | 7/2004 | Jimenez Mayorga et al. |
| 2004/0186102 A1 | 9/2004 | Wu et al. |
| 2004/0186148 A1 | 9/2004 | Shankar et al. |
| 2004/0192664 A1 | 9/2004 | Kunz et al. |
| 2004/0198997 A1 | 10/2004 | Scholz et al. |
| 2004/0254188 A1 | 12/2004 | Gomtsyan et al. |
| 2005/0010047 A1 | 1/2005 | Bonnert et al. |
| 2005/0038248 A1 | 2/2005 | Henderson et al. |
| 2005/0043351 A1 | 2/2005 | Gomtsyan et al. |
| 2005/0054850 A1 | 3/2005 | Wu et al. |
| 2005/0059800 A1 | 3/2005 | Sudhakar et al. |
| 2005/0107399 A1 | 5/2005 | Boman et al. |
| 2005/0154053 A1 | 7/2005 | Rhijn et al. |
| 2005/0165058 A1 | 7/2005 | Nazare et al. |
| 2005/0250820 A1 | 11/2005 | Chen |
| 2006/0014807 A1 | 1/2006 | Lin |
| 2006/0020039 A1 | 1/2006 | Zhu et al. |
| 2006/0035934 A1 | 2/2006 | Gomtsyan et al. |
| 2006/0074103 A1 | 4/2006 | Corte et al. |
| 2006/0116364 A1 | 6/2006 | Hamaoka et al. |
| 2006/0167317 A1 | 7/2006 | Reddy et al. |
| 2006/0173075 A1 | 8/2006 | Krauss et al. |
| 2006/0183783 A1 | 8/2006 | Polisetti et al. |
| 2006/0193797 A1 | 8/2006 | Zhang et al. |
| 2006/0247262 A1 | 11/2006 | Baenteli et al. |
| 2006/0264481 A1 | 11/2006 | Chen |
| 2007/0088172 A1 | 4/2007 | Michalak et al. |
| 2007/0111965 A1 | 5/2007 | Kipp et al. |
| 2007/0142352 A1 | 6/2007 | Bonnert et al. |
| 2007/0237840 A1 | 10/2007 | Chern et al. |
| 2007/0238763 A1 | 10/2007 | Jimenez Mayorga et al. |
| 2007/0282103 A1 | 12/2007 | Butters et al. |
| 2008/0004312 A1 | 1/2008 | Anderson et al. |
| 2008/0009088 A1 | 1/2008 | Lee |
| 2008/0119454 A1 | 5/2008 | Polisetti et al. |
| 2008/0119455 A1 | 5/2008 | Polisetti et al. |
| 2008/0153876 A1 | 6/2008 | Sinha et al. |
| 2008/0176816 A1 | 7/2008 | Chern et al. |
| 2008/0194557 A1 | 8/2008 | Barbosa et al. |
| 2008/0194803 A1 | 8/2008 | Sinclair et al. |
| 2008/0200458 A1 | 8/2008 | Barbosa et al. |
| 2008/0227799 A1 | 9/2008 | Liotta et al. |
| 2008/0227976 A1 | 9/2008 | Mortimore et al. |
| 2008/0261978 A1 | 10/2008 | Clark et al. |
| 2008/0262234 A1 | 10/2008 | Bientinesi et al. |
| 2008/0287676 A1 | 11/2008 | Gomtsyan et al. |
| 2008/0293711 A1 | 11/2008 | Clark et al. |
| 2008/0306053 A1 | 12/2008 | Tachdjian et al. |
| 2008/0306093 A1 | 12/2008 | Servant et al. |
| 2008/0312217 A1 | 12/2008 | Collingwood et al. |
| 2009/0043097 A1 | 2/2009 | Thomson et al. |
| 2009/0068197 A1 | 3/2009 | Steyn et al. |
| 2009/0163545 A1 | 6/2009 | Goldfarb |
| 2009/0176776 A1 | 7/2009 | Prevelige |
| 2009/0227790 A1 | 9/2009 | Lin |
| 2009/0325930 A1 | 12/2009 | Hamaoka et al. |
| 2010/0015218 A1 | 1/2010 | Jadhav et al. |
| 2010/0026778 A1 | 2/2010 | Hayashi |
| 2010/0093734 A1 | 4/2010 | Boman et al. |
| 2010/0093735 A1 | 4/2010 | Boman et al. |
| 2010/0105733 A1 | 4/2010 | Lyttle et al. |
| 2010/0152182 A1 | 6/2010 | Baenteli et al. |
| 2010/0217000 A1 | 8/2010 | Butters et al. |
| 2010/0267778 A1 | 10/2010 | Kusuda et al. |
| 2010/0273797 A1 | 10/2010 | Boman et al. |
| 2011/0077305 A1 | 3/2011 | Jackson |
| 2011/0105472 A1 | 5/2011 | Greul et al. |
| 2011/0144066 A1 | 6/2011 | Mahadevan et al. |
| 2011/0224155 A1 | 9/2011 | Tachdjian et al. |
| 2011/0294853 A1 | 12/2011 | Pelcman et al. |
| 2011/0301158 A1 | 12/2011 | Polisetti et al. |
| 2011/0319420 A1 | 12/2011 | Yang et al. |
| 2012/0004315 A1 | 1/2012 | Hamaoka et al. |
| 2012/0190845 A1 | 7/2012 | Gomtsyan et al. |
| 2012/0295904 A1 | 11/2012 | Zhi et al. |
| 2013/0022629 A1 | 1/2013 | Sharpe et al. |
| 2013/0039945 A1 | 2/2013 | Iadonato et al. |
| 2013/0096159 A1 | 4/2013 | Maloney et al. |
| 2013/0109658 A1 | 5/2013 | Testi et al. |
| 2013/0131140 A1 | 5/2013 | Nadler et al. |
| 2013/0183252 A1 | 7/2013 | Li et al. |
| 2013/0184317 A1 | 7/2013 | Mahadevan et al. |
| 2013/0210915 A1 | 8/2013 | Wadell et al. |
| 2013/0310379 A1 | 11/2013 | Albrecht et al. |
| 2013/0338369 A1 | 12/2013 | Heinrich et al. |
| 2014/0113012 A1 | 4/2014 | Schultz et al. |
| 2014/0163078 A1 | 6/2014 | Steyn et al. |
| 2014/0179743 A1 | 6/2014 | Shapiro et al. |
| 2014/0235623 A1 | 8/2014 | Tachdjian et al. |
| 2014/0243324 A1 | 8/2014 | Bissonnette et al. |
| 2014/0328756 A1 | 11/2014 | Radeke et al. |
| 2014/0336185 A1 | 11/2014 | Boehm et al. |
| 2015/0126563 A1 | 5/2015 | Mahadevan et al. |
| 2015/0160842 A1 | 6/2015 | Yabuki |
| 2015/0203493 A1 | 7/2015 | Guckian et al. |
| 2015/0252043 A1 | 9/2015 | Zhi et al. |
| 2016/0096800 A1 | 4/2016 | Walter et al. |
| 2016/0200639 A1 | 7/2016 | Hartwig et al. |
| 2016/0264540 A1 | 9/2016 | Wipf et al. |
| 2017/0001955 A1 | 1/2017 | Maloney et al. |

FOREIGN PATENT DOCUMENTS

| | | |
|---|---|---|
| AU | 2013254904 | 2/2014 |
| CA | 1327204 | 2/1994 |
| CA | 2268916 | 5/1998 |
| CA | 2470214 | 12/2002 |
| CN | 1743318 | 3/2006 |
| CN | 1754873 | 4/2006 |
| CN | 1878769 | 12/2006 |
| CN | 100343236 C | 10/2007 |
| CN | 101130526 | 2/2008 |
| CN | 101177385 | 5/2008 |
| CN | 101652136 | 2/2010 |
| CN | 102206172 | 10/2011 |
| CN | 104163794 | 11/2014 |
| DE | 19740785 | 8/1998 |
| EP | 0416609 | 3/1991 |
| EP | 2546229 | 1/2013 |
| JP | 2000212076 | 8/2000 |
| JP | 2009209090 | 9/2009 |
| MY | 139321 | 9/2009 |
| TW | I320409 B | 2/2010 |
| WO | WO-9008545 A1 | 8/1990 |
| WO | WO-1990/012008 | 10/1990 |
| WO | WO-9610559 | 4/1996 |
| WO | WO-1996/012956 | 5/1996 |
| WO | WO-9701275 | 1/1997 |
| WO | WO-9818461 | 5/1998 |
| WO | WO-9837287 | 8/1998 |
| WO | WO-9946236 | 9/1999 |
| WO | WO-1999043809 | 9/1999 |
| WO | WO-01/004159 | 1/2001 |
| WO | WO-2001019798 | 3/2001 |
| WO | WO-2002039987 | 5/2002 |
| WO | WO-2003007955 | 1/2003 |
| WO | WO-2004099127 | 11/2004 |
| WO | WO-2005000309 | 1/2005 |
| WO | WO-2005065074 | 7/2005 |
| WO | WO-2005103030 | 11/2005 |
| WO | WO-2006038594 | 4/2006 |
| WO | WO-2006078941 | 7/2006 |
| WO | WO-2007110649 | 10/2007 |
| WO | WO-2009/012242 | 1/2009 |
| WO | WO-2009118596 | 10/2009 |
| WO | WO-2010123139 | 10/2010 |

(56) References Cited

FOREIGN PATENT DOCUMENTS

| | | |
|---|---|---|
| WO | WO-2011/146618 | 11/2011 |
| WO | WO-2012016133 | 2/2012 |
| WO | WO-2013/050441 | 4/2013 |
| WO | WO-2013132006 | 9/2013 |
| WO | WO-2013/165969 | 11/2013 |
| WO | WO-2015134973 | 9/2015 |
| ZA | 9902029 B | 9/1999 |

OTHER PUBLICATIONS

Luci et al. Synthesis and structure-activity relationship studies of 4-((-2-hydroxy-3-methoxybenzyl)amino)benzenesulfonamide derivatives as potent and selective inhibitors of 12-lipoxygenase. J. Med. Chem. Jan. 23, 2014; 57(2): 495-506.*

Aharony et al., "Regulation of arachidonate-induced platelet aggregation by the lipoxygenase product, 12-hydroperoxyeicosatetraenoic acid," Biochim. Biophys. Acta 718, pp. 193-200 (1982).

Amagata et al., "Exploring Sponge-Derived Terpenoids for Their Potency and Selectivity against 12-Human, 15-Human, and 15-Soybean Lipoxygenases," J. Nat. Prod. 66, pp. 230-235 (2003).

Arai et al., "Platelets with 10% of the normal amount of glycoprotein VI have an impaired response to collagen that results in a mild bleeding tendency," British Journal of Haematology 89(1), pp. 124-130 (1995).

Asselin et al., "A collagen-like peptide stimulates tyrosine phosphorylation of syk and phospholipase Cgamma2 in platelets independent of the integrin alpha2beta1," Blood 89(4), pp. 1235-1242 (1997).

Berger et al., "Zileuton: Clinical Implications of 5-Lipoxygenase Inhibition in Severe Airway Disease," Int. J. Clin. Pract. 61, pp. 663-676 (2007).

Bergmeier and Stefanini, "Platelet ITAM signaling," Current Opinion in Hematology 20(5), pp. 445-450 (2013).

Bertoni et al., "Relationships between Rap 1b, affinity modulation of integrin $\alpha_{IIb}\beta_3$, and the actin cytoskeleton," The Journal of Biological Chemistry 277(28), pp. 25715-25721 (2002).

Blake et al., "Collagen stimulates tyrosine phosphorylation of phospholipase C-gamma2 but not phospholipase C-gamma1 in human platelets," FEBS Letters 353(2), pp. 212-216 (1994).

Bledzka et al., "Integrin alphaIIbbeta3: from discovery to efficacious therapeutic target," Circulation Research 112(8), pp. 1189-1200 (2013).

Bleich et al., "Resistance to type 1 diabetes induction in 12-lipoxygenase knockout mice," J. Clin. Invest. 103, pp. 1431-1436 (1999).

Brash, "A review of possible roles of the platelet 12-lipoxygenase," Circulation 72, pp. 702-707 (1985).

Brash, "Lipoxygenases: Occurrence, Functions, Catalysis and Acquisition of Substrate," J. Biol. Chem. 274, pp. 23679-23682 (1999).

Brass et al., "GTP-binding proteins and platelet activation," Progress in Hemostasis and Thrombosis 10, pp. 127-174 (1991).

Brem et al., "Interstitial chemotherapy with drug polymer implants for the treatment of recurrent gliomas," J. Neurosurg. 74, pp. 441-446 (1991).

Catalano and Procopio, "New aspects on the role of lipoxygenases in cancer progression," Histol. Histopathol. 20, pp. 969-975 (2005).

Chang et al., "Inhibition of platelet and neutrophil phospholipase $A_2$ by hydroxyeicosatetraenoic acids (HETES). A novel pharmacological mechanism for regulating free fatty acid release," Biochem. Pharmacol. 34, pp. 1571-1575 (1985).

Chen et al., "Activation of 12-Lipoxygenase in proinflammatory cytokine-mediated beta cell toxicity," Diabetologia 48, pp. 486-495 (2005).

Chen et al., "Purification and characterization of recombinant histidine-tagged human platelet 12-lipoxygenase expressed in a baculovirus/insect cell system," Eur. J. Biochem. 214, pp. 845-852 (1993).

Chrzanowska-Wodnicka et al., "Rap1b is required for normal platelet function and hemostasis in mice," The Journal of Clinical Investigation 115(3), pp. 680-687 (2005).

Cichewicz et al., "Redox inactivation of human 15-lipoxygenase by marine-derived meroditerpenes and synthetic chromanes: archetypes for a unique class of selective and recyclable inhibitors," J. Am. Chem. Soc. 126, pp. 14910-14920 (2004).

Coffey et al., "Platelet 12-lipoxygenase activation via glycoprotein VI: involvement of multiple signaling pathways in agonist control of H(P)ETE synthesis," Circulation Research 94(12), pp. 1598-1605 (2004).

Cyrus et al., "Disruption of the 12/15-lipoxygenase gene diminishes atherosclerosis in apo E-deficient mice," J. Clin. Invest. 103, pp. 1597-1604 (1999).

Deschamps et al., "Baicalein is a potent in vitro inhibitor against both reticulocyte 15-human and platelet 12-human lipoxygenases," Bioorg. Med. Chem. 14, pp. 4295-4301 (2006).

Deschamps et al., "Discovery of platelet-type 12-human lipoxygenase selective inhibitors by high-throughput screening of structurally diverse libraries," Bioorg. Med. Chem. 15, pp. 6900-6908 (2007).

Elalamy et al., "Heparin-induced thrombocytopenia: Laboratory diagnosis and management," Ann. Med. 32, pp. 60-67 (2000).

Ettmayer et al. "Lessons learned from marketed and investigational prodrugs," J. Med. Chem. 47, pp. 2393-2404 (2004).

Fukami and Salganicoff, "Human platelet storage organelles. A review," Thrombosis and Haemostasis 38(4), pp. 963-970 (1977).

Gan et al., "Defining the arachidonic acid binding site of human 15-lipoxygenase," J. Biol. Chem. 271, pp. 25412-25418 (1996).

Ghosh and Myers, "Inhibition of Arachidonate 5-Lipoxygenase Triggers Massive Apoptosis in Human Prostate Cancer Cells," Proc. Natl. Acad. Sci. U.S.A. 95, pp. 13182-13187 (1998).

Ghosh, "Inhibition of Arachidonate 5-Lipoxygenase Triggers Prostate Cancer Cell Death through Rapid Activation of $_c$-Jun N-Terminal Kinase," Biochem. Biophys. Res. Commun. 307, pp. 342-349 (2003).

Giannopoulos et al., "The 12-15-lipoxygenase is a modulator of Alzheimer's-related tau pathology in vivo," Aging Cell 12(6), pp. 1082-1090 (2013).

Gibbins et al., "Tyrosine phosphorylation of the Fc receptor gamma-chain in collagen-stimulated platelets," The Journal of Biological Chemistry 271(30), pp. 18095-18099 (1996).

Greinacher et al., "Heparin-induced thrombocytopenia," Hämostaseologie 30(1), pp. 17-18, 20-28 (2010).

Guo et al., "Identification of the orphan G protein-coupled receptor GPR31 as a receptor for 12-(S)-hydroxyeicosatetraenoic acid," The Journal of Biological Chemistry 286(39), pp. 33832-33840 (2011).

Guo et al., "Role of 12-lipoxygenase in decreasing P-cadherin and increasing angiotensin II type 1 receptor expression according to glomerular size in type 2 diabetic rats," Am. J. Physiol. Endocrinol. Metab. 300, pp. E708-E716 (2011).

Harats et al., "Overexpression of 15-lipoxygenase in vascular endothelium accelerates early atherosclerosis in LDL receptor-deficient mice," Arterioscler. Thromb. Vasc. Biol. 20, pp. 2100-2105 (2000).

Holmsen and Weiss, "Secretable storage pools in platelets," Annual Review of Medicine 30, pp. 119-134 (1979).

Honn et al., "A Lipoxygenase metabolite, 12-(S)-HETE, stimulates protein kinase C-mediated release of cathepsin B from malignant cells," Exp. Cell. Res. 214, pp. 120-130 (1994).

Hoobler et al., "Pseudoperoxidase investigations of hydroperoxides and inhibitors with human lipoxygenases," Bioorg. Med. Chern. 21, pp. 3894-3899 (2013).

Ikei et al., "Investigations of human platelet-type 12-Lipoxygenase: role of lipoxygenase products in platelet activation," J. Lipid Res. 53, pp. 2546-2559 (2012).

Inglese et al., "Quantitative High-Throughput Screening: A Titration-Based Approach That Efficiently Identifies Biological Activities in Large Chemical Libraries," Proc. Natl. Acad. Sci. U.S.A. 103, pp. 11473-11478 (2006).

International Search Report and Written Opinion for International Patent Application No. PCT/US14/60174 dated Dec. 31, 2014 (9 pages).

Israels et al., "Platelet storage pool deficiency: diagnosis in patients with prolonged bleeding times and normal platelet aggregation," British Journal of Haematology 75(1), pp. 118-121 (1990).

(56) References Cited

OTHER PUBLICATIONS

Jankun et al., "Synthetic curcuminoids modulate the arachidonic acid metabolism of human platelet 12-lipoxygenase and reduce sprout formation of human endothelial Cells," Molecular Cancer Therapeutics 5(5), pp. 1371-1382 (2006).
Kamitani et al., "The possible involvement of 15-lipoxygenase/leukocyte type 12-lipoxygenase in colorectal carcinogenesis," Adv. Exp. Med. Biol. 469, pp. 593-598 (1999).
Kandouz et al., "Platelet-type 12-lipoxygenase activates NF-kappaB in prostate cancer cells," Prostaglandins & Other Lipid Mediators 71(3-4), pp. 189-204 (2003).
Kasirer-Friede et al., "Platelet integrins and immunoreceptors," Immunological Reviews 218, pp. 247-264 (2007).
Katoh et al., "Platelet-derived 12-hydroxyeicosatetraenoic acid plays an important role in mediating canine coronary thrombosis by regulating platelet glycoprotein IIb/IIIa activation," Circulation 98(25) pp. 2891-2898 (1998).
Kayama et al., "Cardiac 12/15 lipoxygenase-induced inflammation is involved in heart failure," J. Exp. Med. 206, pp. 1565-1574 (2009).
Kenyon et al., "Discovery of Potent and Selective Inhibitors of Human Platelet-Type 12-Lipoxygenase," J. Med. Chem. 54, pp. 5485-5497 (2011).
Kenyon et al., "Novel human lipoxygenase inhibitors discovered using virtual screening with homology models," J. Med. Chem. 49, pp. 1356-1363 (2006).
Kinzig et al., "Murine epidermal lipoxygenase (*Aloxe*) encodes a 12-lipoxygenase isoform," FEBS Lett. 402, pp. 162-166 (1997).
Lee et al., "7-Fluoroindazoles as Potent and Selective Inhibitors of Factor Xa," J. Med. Chem. 51(2), pp. 282-297 (2008).
Luci et al., "Synthesis and structure-activity relationship studies of 4-((2-hydroxy-3-methoxybenzyl)amino)benzenesulfonamide derivatives as potent and selective inhibitors of 12-Lipoxygenase," Journal of Medicinal Chemistry 57(2), pp. 495-506 (2014).
Ma et al., "12-Lipoxygenase Products Reduce Insulin Secretion and β-cell Viability in Human Islets," J. Clin. Endocrinol. Metab. 95, pp. 887-893 (2010).
Madsen et al., "Optimization of Alkylidene Hydrazide Based Human Glucagon Receptor Antagonists. Discovery of the Highly Potent and Orally Available 3-Cyano-4-hydroxybenzoic Acid [1-(2,3,5,6-Tetramethylbenzyl)-1H-indol-4-ylmethylene]hydrazide," J. Med. Chem. 45, pp. 5755-5775 (2002).
Malterud and Rydland, "Inhibitors of 15-lipoxygenase from orange peel," J. Agric. Food Chem. 48, pp. 5576-5580. (2000).
Martinez-Clemente et al., "Disruption of the 12/15-lipoxygenase gene (*Alox15*) protects hyperlipidemic mice from nonalcoholic fatty liver disease," Hepatology 52, pp. 1980-1991 (2010).
McDuffie et al., "Nonobese diabetic (NOD) mice congenic for a targeted deletion of 12/15-Lipoxygenase are protected from autoimmune diabetes," Diabetes 57, pp. 199-209 (2008).
McMahon et al., "Transient heparin-induced platelet activation linked to generation of platelet 12-lipoxygenase. Findings from a randomised controlled trial," Thrombosis and Haemostasis 109(6), pp. 1099-1107 (2013).
McNicol and Israels, "Platelet dense granules: structure, function and implications for haemostasis," Thrombosis Research 95(1), pp. 1-18 (1999).
Moreau et al., "Modulation of lipoxygenase activity by bacterial hopanoids," J. Nat. Prod. 60, pp. 397-398 (1997).
Morgan et al., "Thrombin-activated human platelets acutely generate oxidized docosahexaenoic-acid-containing phospholipids via 12-lipoxygenase," The Biochemical Journal 431(1), pp. 141-148 (2010).
Moroi et al., "A patient with platelets deficient in glycoprotein VI that lack both collagen-induced aggregation and adhesion," The Journal of Clinical Investigation 84(5), pp. 1440-1445 (1989).
Nakano et al., "Synthesis and Biological Activities of Novel Antiallergic Agents with 5-Lipoxygenase Inhibiting Action," Bioorg. Med. Chem. 8, pp. 373-380 pp. (2000).

Nappez et al., "Changes in lipoxygenase activities in human erythroleukemia (HEL) cells during diosgenin-induced differentiation," Cancer Lett. 96, pp. 133-140 (1995).
Natarajan et al., "Increased 12-lipoxygenase expression in breast cancer tissues and cells. Regulation by epidermal growth factor," J. Clin. Endocrinol. Metab. 82, pp. 1790-1798 (1997).
Nie et al., "Eicosanoid regulation of angiogenesis: role of endothelial arachidonate 12-lipoxygenase," Blood 95, pp. 2304-2311 (2000).
Nie et al., "Mechanisms regulating tumor angiogenesis by 12-lipoxygenase in prostate cancer cells," The Journal of Biological Chemistry 281(27), pp. 18601-18609 (2006).
Nie et al., "Platelet-type 12-lipoxygenase in a human prostate carcinoma stimulates angiogenesis and tumor growth," Cancer Res. 58, 4047-4051 (1998).
Nyby et al., "Platelet lipoxygenase inhibitors attenuate thrombin- and thromboxane mimetic-induced intracellular calcium mobilization and platelet aggregation," J. Pharmacol. Exp. Ther. 278, pp. 503-509 (1996).
Ohri et al., "A Re(V)-catalyzed C—N bond-forming route to human lipoxygenase inhibitors," Org. Lett. 7, pp. 2501-2504 (2005).
Phillips and Agin, "Platelet membrane defects in Glanzmann's thrombasthenia. Evidence for decreased amounts of two major glycoproteins," The Journal of Clinical Investigation 60(3), pp. 535-545 (1977).
Poste et al., "Lipid Vesicles as Carriers for Introducing Biologically Active Materials into Cells," Methods in Cell Biology, Chapter 4, vol. 14, pp. 33-71 (1976).
Pratico et al., "12/15-Lipoxygenase is increased in Alzheimer's disease: *possible involvement in brain oxidative stress*," Am. J. Pathol. 164, pp. 1655-1662 (2004).
Pubchem, CID 70701358. Create Date: Feb. 22, 2013, pp. 1-8 (online), [retrieved on Dec. 11, 2014] Retrieved from the internet <https://pubchem.ncbi.nlm.nih.gov/compound/70701358>.
Pubchem, CID 70701426. Create Date: Feb. 22, 2013, pp. 1-10 [online], [retrieved on Dec. 10, 2014] Retrieved from the internet <https://pubchem.ncbi.nlm.nih.gov/compound/70701426#section=Top>.
Pubchem, CID 70701432. Create Date: Feb. 22, 2013, pp. 1-9 [online], [retrieved on Dec. 10, 2014] Retrieved from the internet <https://pubchem.ncbi.nlm.nih.gov/compound/70701432#section=2D-Structure>.
Pubchem, CID 70701440. Create Date: Feb. 22, 2013, pp. 1-8 [online], [retrieved on Dec. 11, 2014] Retrieved from the internet <https://pubchem.ncbi.nlm.nih.gov/compound/70701440>.
Rådmark and Samuelsson, "5-Lipoxygenase: Regulation and Possible Involvement in Atherosclerosis," Prostaglandins Other Lipid Mediat. 83, pp. 162-174 (2007).
Reilly et al., "PRT-060318, a novel Syk inhibitor, prevents heparin-induced thrombocytopenia and thrombosis in a transgenic mouse model," Blood 117(7), pp. 2241-2246 (2011).
Robinson et al., "Using enzyme assays to evaluate the structure and bioactivity of sponge-derived meroterpenes," J. Nat. Prod. 72, pp. 1857-1863 (2009).
Rosenfeld et al., "Human platelet Fc receptor for immunoglobulin G. Identification as a 40,000-molecular-weight membrane protein shared by monocytes," The Journal of Clinical Investigation 76(6), pp. 2317-2322 (1985).
Sailer et al., "Characterization of an acetyl-11-keto-Beta-boswellic acid and arachidonate-binding regulatory site of 5-lipoxygenase using photoaffinity labeling," Eur. J. Biochem. 256, pp. 364-368 (1998) English language abstract.
Samama et al., "Heparin-induced thrombocytopenia: interest and difficulties to identify the immunologic mechanism," Bull Acad. Natl. Med. 182, pp. 1517-1536 (1998).
Segraves et al., "Probing the activity differences of simple and complex brominated aryl compounds against 15-soybean, 15-human, and 12-human lipoxygenase," J. Med. Chem. 47, pp. 4060-4065 (2004).
Serhan et al., "Resolvins and Protectins in Inflammation Resolution," Chem. Rev. 111, pp. 5922-5943 (2011).
Solomon et al., "New insights from spectroscopy into the structure/function relationships of lipoxygenases," Chem. Biol. 4, pp. 795-808 (1997).

(56) References Cited

OTHER PUBLICATIONS

Soriano et al., "Synergistic effects of new chemopreventive agents and conventional cytotoxic agents against human lung cancer cell lines," Cancer Res. 59, pp. 6178-6184 (1999).
Stavniichuk et al., "Interplay of Sorbitol Pathway of Glucose Metabolism, 12/15-Lipoxygenase, and Mitogen-Activated Protein Kinases in the Pathogenesis of Diabetic Peripheral Neuropathy," Biochem. Pharmacol. 83, pp. 932-940 (2012).
Strehl et al., "Dual role of platelet protein kinase C in thrombus formation: stimulation of pro-aggregatory and suppression of procoagulant activity in platelets," The Journal of Biological Chemistry 282(10), pp. 7046-7055 (2007).
Sugiyama et al., "A novel platelet aggregating factor found in a patient with defective collagen-induced platelet aggregation and autoimmune thrombocytopenia," Blood 69(6), et al. 1712-1720 (1987).
Suzuki-Inoue et al., "A novel Syk-dependent mechanism of platelet activation by the C-type lectin receptor CLEC-2," Blood 107(2), pp. 542-549 (2006).
Suzuki-Inoue et al., "Novel platelet activation receptor CLEC-2: from discovery to prospects," Journal of Thrombosis and Haemostasis 9, Suppl. 1, pp. 44-55 (2011).
Takai, "Roles of Fc receptors in autoimmunity," Nature Reviews Immunology 2(8), pp. 580-592 (2002).
Tanaka et al., "Disruption of phospholipid and bile acid homeostasis in mice with nonalcoholic steatohepatitis," Hepatology 56, pp. 118-129 (2012).
Thomas et al., "Phospholipid-esterified eicosanoids are generated in agonist-activated human platelets and enhance tissue factor-dependent thrombin generation," The Journal of Biological Chemistry 285(10), pp. 6891-6903 (2010).
Timar et al., "Regulation of melanoma-cell motility by the lipoxygenase metabolite 12-(S)-HETE," Int. J. Cancer 55, pp. 1003-1010 (1993).
Tsuji et al., "A novel association of Fc receptor γ-Chain with glycoprotein VI and their co-expression as a collagen receptor in human platelets," The Journal of Biological Chemistry 272(38), pp. 23528-23531 (1997).
Van Leyen et al., "Baicalein and 12/15-lipoxygenase in the ischemic brain," Stroke 37, pp. 3014-3018 (2006).
Van Leyen et al., "Novel lipoxygenase inhibitors as neuroprotective reagents," J. Neurosci. Res. 86, pp. 904-909 (2008).
Vasquez-Martinez et al., "Structure-activity relationship studies of flavonoids as potent inhibitors of human platelet 12-hLO, reticulocyte 15-hL0-1, and prostate epithelial 15-hL0-2," Bioorg. Med. Chem. 15, pp. 7408-7425 (2007).
Wang et al., "Copper-catalyzed N-arylation of sulfonamides with aryl bromides under mild conditions," Tetrahedron Lett. 53, pp. 7-10 (2012).
Watanabe et al., "Mechanisms and consequences of agonist-induced talin recruitment to platelet integrin αIIbβ3," The Journal of Cell Biology 181(7), pp. 1211-1222 (2008).
Whitman et al., "Structure-activity relationship studies of nordihydroguaiaretic acid inhibitors toward soybean, 12-human, and 15-human lipoxygenase," J. Med. Chem. 45, pp. 2659-2661 (2002).
Yacoub et al., "Essential Role of Protein Kinase Cδ in Platelet Signaling, $α_{IIb}β_3$ Activation, and Thromboxane $A_2$ Release," The Journal of Biological Chemistry 281(40), pp. 30024-30035 (2006).
Yamamoto, "Mammalian lipoxygenases: Molecular Structures and functions," Biochim. Biophys. Acta. 1128, pp. 117-131 (1992).
Yanaga et al., "Syk interacts with tyrosine-phosphorylated proteins in human platelets activated by collagen and cross-linking of the Fcγ-llA receptor," The Biochemical Journal 311 (Pt. 2), pp. 471-478 (1995).
Yeung et al., "12-lipoxygenase activity plays an important role in PAR4 and GPVI-mediated platelet reactivity," Thrombosis and Haemostasis 110(3), pp. 569-581 (2013).
Yeung et al., "Platelet 12-LOX is essential for FcγRlla-mediated platelet activation," Blood 124(14), pp. 2271-2279 (2014) (DOI 10.1182/blood-2014-05-575878).
Yeung et al., "Protein Kinase C Regulation of 12-Lipoxygenase-Mediated Human Platelet Activation," Mol. Pharmacol. 81, pp. 420-430 (2012).
Zhi et al., "Cooperative integrin/ITAM signaling in platelets enhances thrombus formation in vitro and in vivo," Blood 121(10), pp. 1858-1867 (2013).
Pubchem, CID 70701358. Deposit Date: Feb. 22, 2013, pp. 1-6 (online), [Available Date: Feb. 20, 2014] Retrieved from the internet <https://pubchem.ncbi.nlm.nih.gov/substance/160844100>.
Pubchem, CID 70701426. Deposit Date: Feb. 22, 2013, pp. 1-6 [online], [Available Date: Jan. 10, 2014] Retrieved from the internet <https://pubchem.ncbi.nlm.nih.gov/substance/160844040>.
Pubchem, CID 70701432. Deposit Date: Feb. 22, 2013, pp. 1-6 [online], [Available Date: Feb. 20, 2014] Retrieved from the internet <https://pubchem.ncbi.nlm.nih.gov/substance/160844112>.
Pubchem, CID 70701440. Deposit Date: Feb. 22, 2013, pp. 1-6 [online], [Available Date: Feb. 20, 2014;) Retrieved from the internet <https://pubchem.ncbi.nlm.nih.gov/substance/160844040>.
Database Registry [Online] Chemical Abstracts Service, Columbus, Ohio, US; Mar. 14, 2006 (Mar. 14, 2006), XP002766775, Database accession No. 876723-83-0 (3-Methoxy-2-Pyrazinyl)-4-[[2-Hydroxy-3-(2-Propen-1-Yl)Phenyl]Methyl]Amino]N-Benzene Sulfonamide (1 page).
Database Registry [Online] Chemical Abstracts Service, Columbus, Ohio, US; Mar. 14, 2006 (Mar. 14, 2006), XP002766777, Database accession No. 876723-77-2 4-[[(2-Hydroxyphenyl)Methyl]Amino]N-(3-Methoxy-2-Pyrazinyl)-Benzenesulfonamide (1 page).
Database Registry [Online] Chemical Abstracts Service, Columbus, Ohio, US; Mar. 14, 2006 (Mar. 14, 2006), XP002766780, Database accession No. 876723-74-9 N-(2,6-Dimethoxy-4-Pyrimidinyl)-4-[[(2-Hydroxyphenyl)Methyl]Amino]-Benzenesulfonamide (1 page).
Database Registry [Online] Chemical Abstracts Service, Columbus, Ohio, US; Apr. 20, 2007 (Apr. 20, 2007), XP002766776, Database accession No. 931362-36-6 N-(2,6-Dimethoxy-4-Pyrimidinyl)-4-[[2-Hydroxy-3-(2-Propen-1-Yl)Phenyl]Methyl]Amino] Benzenesulfonamide (1 page).
Database Registry [Online] Chemical Abstracts Service, Columbus, Ohio, US; Feb. 24, 2005 (Feb. 24, 2005), XP002766781, Database accession No. 836664-06-3 N-(4,6-Dimethyl-2-Pyrimidinyl)-4-[[[2-Hydroxy-3-(2-Propen-1-Yl)Phenyl]Methyl]Amino]-Benzenesulfonamide (1 page).
Database Registry [Online] Chemical Abstracts Service, Columbus, Ohio, US; Jul. 26, 2002 (Jul. 26, 2002), XP002766778, Database accession No. 440335-64-8 N-(5-Ethyl-1,3,4-Thiadiazol-2-Yl)-4-[[(2-Hydroxyphenyl)Methyl]Amino]-Benzenesulfonamide (1 page).
Database Registry [Online] Chemical Abstracts Service, Columbus, Ohio, US; Dec. 6, 2004 (Dec. 6, 2004), XP002766779, Database accession No. 792944-90-2 N-(4,6-Dimethyl-2-Pyrimidinyl)-4-[[(2-Hydroxyphenyl)Methyl]Amino]-Benzenesulfonamide (1 page).
Supplementary European Search Report for European Patent Application No. 14 85 2765.8 dated Feb. 27, 2017 (12 pages).

\* cited by examiner

Scheme 1. Synthesis of analogs 1-83.

Figures 10A – 10E
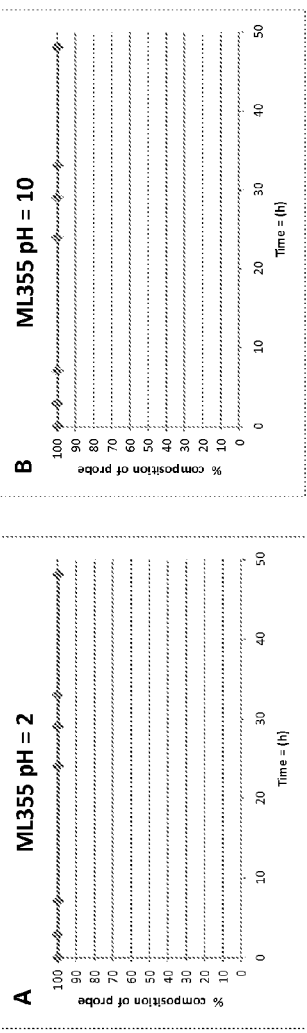
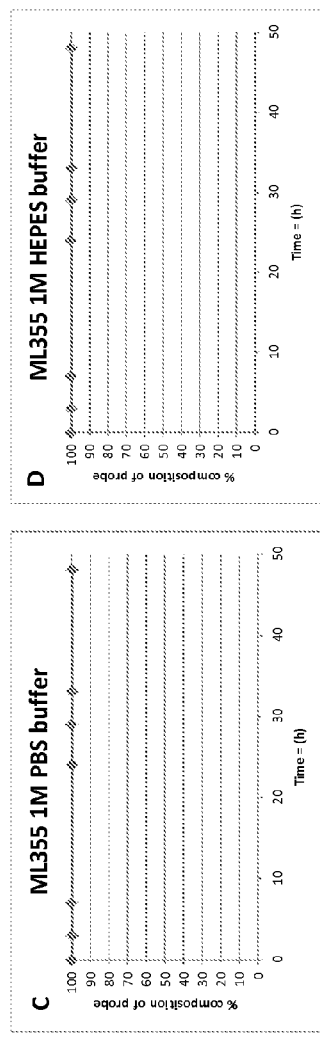
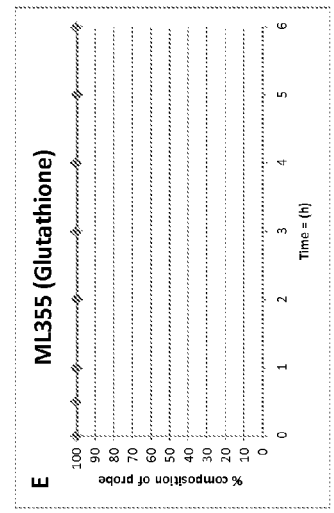

4-((2-HYDROXY-3-METHOXYBENZYL) AMINO)BENZENESULFONAMIDE DERIVATIVES AS POTENT AND SELECTIVE INHIBITORS OF 12-LIPOXYGENASE

CROSS-REFERENCE TO RELATED APPLICATIONS

This application is a National Stage Application of PCT Application No. PCT/US14/60174 filed Oct. 10, 2014, which claims the benefit of U.S. Provisional Application No. 61/889,396, filed on Oct. 10, 2013, and U.S. Provisional Application No. 61/987,129, filed on May 1, 2014, which are incorporated by reference.

STATEMENT CONCERNING GOVERNMENT RIGHTS IN FEDERALLY-SPONSORED RESEARCH

This invention was made with government support under the intramural research program of the National Center for Advancing Translational Sciences and the Molecular Libraries Initiative of the National Institutes of Health Roadmap for Medical Research grant no. U54MH084681, the National Institute of Health grant no. R01 GM56062, the Molecular Libraries Initiative of the National Institutes of Health Roadmap for Medical Research grant no. R03 MH081283, NIH grant no. S10-RR20939, the National Heart, Lung, and Blood Institute (NHLBI) grant no. HL114405, and the National Institute of General Medical Sciences (NIGMS) grant no. GM105671. The government has certain rights in the invention.

BACKGROUND OF THE INVENTION

Lipoxygenases are a class of non-heme iron-containing enzymes which regio- and stereospecifically oxidize polyunsaturated fatty acid substrates such as arachidonic acid (AA) and linoleic acid (LA). (Solomon, et al. *Chem. Biol.* 1997, 4, 795-808; Brash, *J. Biol. Chem.* 1999, 274, 23679-23682.) The position at which these cis, cis-1,4-pentadiene substrates are oxidized correspond to the requisite lipoxygenase, with the three major human lipoxygenases: 5-LOX, 12-LOX, and 15-LOX-1, oxidizing the C-5, C-12 and C-15 positions respectively. Lipoxygenases are involved in the first committed step in a cascade of metabolic pathways and the products of these enzymes (eicosanoids) are precursors of hormones such as leukotrienes and lipoxins, which mediate a wide array of cellular functions. (Serhan, et al. *Chem. Rev.* 2011, 111, 5922-5943.) Consequently, the lipoxygenase enzymes and their bioactive metabolites (e.g. hydroxyeicosatetraenoic aicd (HETE) and leukotriene $A_4$) have been implicated in a variety of inflammatory diseases and cancers.

Specifically, 5-LOX has been implicated in cancer and inflammatory diseases, such as asthma and remains the only lipoxygenase enzyme for which there is an FDA-approved inhibitor (Zilueton) on the market.

Reticulocyte 15-LOX-1 has a role in atherogenesis, neurodegenerative diseases, and neuronal damage associated from an acute ischemic stroke event.

12-LOX exists as three isozymes, platelet-type, leukocyte, and epidermal, but leukocyte 12-LOX is found in rat, mouse, pig and cow, but not in humans. (Yamamoto *Biochim. Biophys. Acta.* 1992, 1128, 117-131; Funk et al. *FEBS Lett.* 1997, 402, 162-166).

Skin Disease and Platelet Hemostatis: Further, 12-LOX has demonstrated a role in skin diseases and platelet hemostasis.

Transplants: 12-LOX inhibitors also have utility in transplantation/xenotransplantation scenarios, where, for example, islets can be treated ex vivo to improve survival prior to transplant.

Cancer: Platelet-type 12-(S)-LOX (12-LOX) has been found to be overexpressed in a variety of tumor tissues including prostate cancer, colorectal cancer, breast cancer and lung cancer. (Catalano et al. *Histol. Histopathol.* 2005, 20, 969-975; Nie, D et al. *Cancer Res.* 1998, 58, 4047-4051; Natarajan et al. *J. Clin. Endocrinol. Metab.* 1997, 82, 1790-1798; Kamitani et al. *Adv. Exp. Med. Biol.* 1999, 469, 593-598; Soriano et al. *Cancer Res.* 1999, 59, 6178-6184). Moreover, 12-HETE levels have been linked to increased cancer cell metastasis by facilitating tumor cell motility and angiogenesis. (Nappez et al. *Cancer Lett.* 1995, 96, 133-140; Timár et al. *Int. J. Cancer,* 1993, 55, 1003-1010; Honn et al. *Exp. Cell. Res.* 1994, 214, 120-130; Nie et al. *Blood* 2000, 95, 2304-2311).

Diabetes: Type 1 and Type 2 diabetes are serious disorders that can lead to major complications and reduced lifespan. There is an unmet medical need in identifying new ways to protect beta cells in these metabolic disorders. 12-LOX is expressed in human pancreatic islets, which is upregulated and activated by inflammatory cytokines leading to increased 12-LOX translocation. The resulting 12-HETE product leads to reduced insulin secretion, reduced metabolic activity and pancreatic β cell death through the amplification of the inflammatory response. (Chen et al. *Diabetologia* 2005, 48, 486-495). Both non-obese diabetic (NOD) 12-LOX and 12-LOX knock-out ("KO") mice showed significant resistance to the development of diabetes compared to the controls, showing 12-LOX is a regulator in this disease.

Diabetic Kidney Disease: Further, studies show that activation of the 12-LOX pathway plays a role in the development of diabetic kidney disease (diabetic nephropathy) by multiple pathogenic mechanisms, including decreased expression of glomerular P-cadherin. (Guo, Q. et al. *Am. J. Physiol. Endocrinol. Metab.* 2011, 300, E708-E716).

Diabetic Nerve Disease: It has also been shown that increased aldose reductase, the first enzyme of the sorbitol pathway, activity plays a key role in diabetes-associated 12/15-LOX activation in the peripheral nerve and spinal cord. (Stavniichuk, R. et al *Biochem Pharmacol.* 2012, 83, 932-940). Thus, inhibiting 12-LOX is attractive in treating diabetic nerve disease.

Diabetes and Cardiovascular Disease: A selective 12-LOX inhibitor would provide a new therapeutic approach to prevent and/or treat either form of diabetes (type I and type II). The development of 12-hLOX inhibitors provide a potent intracellular approach to decreasing the ability of platelets to form large clots in response to vessel injury or activation of the coagulation pathway. Thus, 12-hLOX inhibition has the ability to attenuate platelet-mediated clot formation caused by diabetes and/or cardiovascular disease and significantly decrease the occurrence of myocardial infarction, congestive heart failure, and stroke. Additionally, studies show that the gene Alox15 that encodes the proteins 12-LOX and 15-LOX are up-regulated in heart failure. Thus, inhibition of 12-LOX could be a treatment for heart failure. (Kayama, Y. et al. *J. Exp. Med.* 2009, 206, 1565-1574).

Thrombosis: 12-LOX and its product 12-HETE have been implicated in the modulation of hemostasis and thrombosis via their role in regulating platelet function (reactivity, clot formation, calcium mobilization). (Brash, A. R. *Circulation* 1985, 72, 702-707). Additionally, FcTRIIa is the receptor on the human platelet responsible for heparin induced thrombocytopenia (HIT). It has been found that 12-LOX is essential for FcTRIIa-induced PLC γ 2 activity leading to activation of calcium mobilization, Rap 1 and PKC activation, and subsequent activation of the integrin αIIbβ3, which demonstrates the role of 12-LOX inhibitors in treating HIT. (Yeung, J. et al. *Blood* 2014, (DOI 10.1182/blood-2014-05-575878)). Further, 12-LOX has demonstrated a role in skin diseases and platelet hemostasis.

Alzheimer's disease: 12-LOX and 15-LOX are widely expressed in the central nervous system and have been reported to be involved in neurobiology of Alzheimer's disease because it modulates amyloid beta and APP processing. It has also been found that 12-LOX and 15-LOX modulate endogenous tau metabolism, making it an attractive therapeutic for treating Alzheimer's and related diseases. (Giannopoulos, P. F., et al. *Aging Cell* 2013, 12, 1082-1090).

Non-Alcoholic steatohepatitis: It has been shown that disruption of the gene encoding for 12-LOX, Alox15, protected mice against hepatic steatosis, insulin resistance, and inflammation in experimental liver disease of metabolic origin. (Martinez-Clemente, M. et al. *Hepatology* 2010, 52, 1980-1991; see also Tanaka, N. et al. *Hepatology* 2012, 56, 118-129).

One difficulty in being able to clearly define the role of 12-LOX in these systems has been the lack of potent and selective 12-LOX small molecule inhibitors.

A previously reported 12-LOX inhibitor, an 8-Hydroxyquinoline based compound (ML127), exhibited excellent selectivity, >50-100 fold selectivity over related lipoxygenases and cyclooxygenase. In contrast to many of the previously reported inhibitors, kinetic experiments revealed that ML127 was a non-competitive and non-reductive inhibitor. Chiral HPLC separation of the probe molecule revealed a chiral preference for activity with the (−)-enantiomer being much more potent than the (+)-enantiomer (<0.5 µM vs. >25 µM, respectively). (Kenyon, V. et al. *J. Med. Chem.* 2011, 54, 5485-5497.) However, the chemical series was difficult to optimize further, given that subtle structural modifications led to diminished activity.

There exists a need for a potent, selective 12-LOX small molecule inhibitor that can be optimized without reducing activity to treat or prevent 12-LOX mediated diseases and disorders. The small molecule inhibitor should be soluble, have favorable ADME properties, and have good in vivo PK properties.

Platelets express three immunoreceptor tyrosine-based activation motif (ITAM) containing transmembrane receptors (glycoprotein VI (GPVI)/FcRy complex, C-type lectin-like receptor 2 (CLEC-2), and Low affinity immunoglobulin gamma Fc region receptor II-a (FcγRIIa)). Ligation of ITAM containing receptors on the surface of platelets leads to a shared downstream signaling pathway culminating in platelet activation. These receptors engage in various degrees of hemostasis and thrombosis; however, they have non-redundant (patho) physiological functions. FcγRIIa, a broadly expressed immunorecptor which is present on the surface of human but not mouse platelets is best known for its pathophysiological role in immune-mediated thrombocytopenia and thrombosis; a family of disorders including immune thrombocytopenia, thrombocytopenia associated with sepsis, and heparin-induced thrombocytopenia (HIT). Selectively inhibiting the FcγRIIa signaling pathway in platelets for prevention of immune-mediated thrombocytopenia and thrombosis has been a long sought approach for prevention of HIT (Reilly et al., *Blood* 2011, 117, 2241-2246).

Heparin is widely used in the clinic to treat thrombosis. However, more than 3-5% of patients taking heparin will develop an immune response to heparin and be at high risk for heparin-induced thrombocytopenia (HIT), which can lead to a life-threatening thrombotic event mediated by the immune system. The current therapeutic approach to treatment of HIT is the removal of heparin treatment and replacement with direct thrombin inhibitors (DTIs) which have an inherently high risk for serious bleeding and must be monitored in the clinic. Even with this potentially fatal complication, heparin remains the standard anticoagulant for prevention and treatment of thrombosis.

Therefore, there is also a need for novel therapeutic approaches that directly target the pathogenesis of HIT.

SUMMARY OF THE INVENTION

The present invention provides compounds and methods comprising compounds useful as 12-LOX inhibitors.

The invention provides compounds that are potent and selective inhibitors of 12-LOX. In addition, the present invention provides compositions comprising these compounds and methods of using these compounds as therapeutic agents in the treatment or prevention of 12-lipoxygenase mediated diseases and disorders. 12-LOX mediated diseases and disorders include those in which 12-LOX is a direct mediator of the diseases and disorders, as well as those in which the inhibition of 12-LOX, although perhaps not a direct mediator, results in therapeutic value in the treatment or prevention of the diseases and disorders. These diseases or disorders include, but are not limited to, type 1 diabetes, type 2 diabetes, diabetic kidney disease, diabetic nerve disease, cardiovascular disease, congestive heart failure, myocardial infarction, stroke, Alzheimer's disease, Non-Alcoholic steatohepatitis, platelet hemostasis, skin diseases, heparin induced thrombocytopenia, thrombosis, prostate cancer, colorectal cancer, breast cancer and lung cancer.

The invention provides a compound of Formula (I):

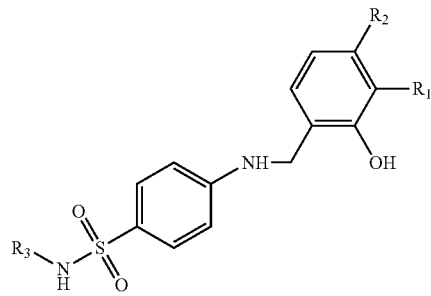

wherein $R_1$ and $R_2$ are independently selected from the group consisting of H, alkyl, alkenyl, alkynyl, F, Cl, Br, amine, nitrogen dioxide, indole, alkoxy, cycloalkyl, aryl, heterocycloalkyl, heteroaryl, each optionally substituted with one or more substituents selected from the group consisting of $C_1$-$C_6$ alkyl, $C_1$-$C_6$ alkenyl, $C_1$-$C_6$ alkynyl, F, Cl, Br, hydroxyl, amine, methoxy;

$R_3$ is selected from the group consisting of phenyl, cycloalkyl, heterocycloalkyl, aryl, heteroaryl, thiazole, benzothiazole, benzoxazole, imidazole, benzimidazole, thiophene, 1-naphthalene, 2-naphthalene, pyridine, quinoline, isoquinoline, 4N-boc-piperidine-3-phenyl, oxazole, benzothiophene, parathiazine, furan, pyran, chromene, benzofuran, pyrrole, pyrazole, pyrazine, pyrimidine, triazine, indole, purine, phthalazine; each optionally substituted with one or more substituents selected from the group consisting of $C_1$-$C_6$ alkyl, $C_1$-$C_6$ alkenyl, $C_1$-$C_6$ alkynyl, F, Cl, Br, hydroxyl, amine, alkoxy, phenyl, cycloalkyl, aryl, piperazine, piperidine, pyridine, morpholine, pyrrolidine, pyrazolidine, imidazolidine, and thiomorpholine;

or a pharmaceutically acceptable salt thereof, enantiomers thereof, a mixture of enantiomers thereof, or diastereomers thereof;

with the proviso that the compound is not

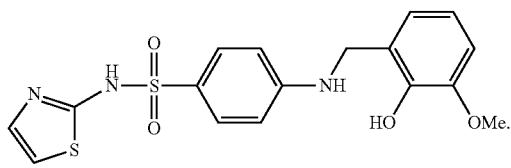 [SMILES: COc1cccc(CNc2ccc(S(=O)(=O)Nc3nccs3)cc2)c1O]

The invention also provides pharmaceutical compositions comprising a compound, salt, enantiomers, a mixture of enantiomers, or diastereomers of the invention and a pharmaceutically acceptable carrier.

The invention further provides a method for treating or preventing a 12-lipoxygenase mediated disease or disorder, comprising administering to a mammal thereof a therapeutically or prophylactically effective amount of a compound, salt thereof, enantiomers thereof, a mixture of enantiomers thereof, or diastereomers thereof of a compound of the present invention.

BRIEF DESCRIPTION OF THE DRAWINGS

FIG. 10. Stability of compound 35 (ML355) measured as percent composition of probe molecule in aqueous solution (contains 20% acetonitrile) at r.t. over the indicated time period in (A) pH 2 buffer (pH 7.4) (B) pH 10 buffer (C) PBS buffer (pH 7.4) (D) Lipoxygenase UV-Vis assay buffer (1M HEPES buffer, pH 7.3) (E) in the presence of 5 mM glutathione (reduced form).

(FIG. 12A) Representative tracings of platelets stimulated with 0.25, 0.5 and 1 µg/mL of anti-CD9. Inset: Western blots for 12-LOX, FcγRIIa, and GAPDH were performed with platelet lysate from hFcR/ALOX12$^{+/+}$ or hFcR/ALOX12$^{-/-}$ mice. The (FIG. 12B) lag time and (FIG. 12C) final aggregation was measured in hFcR/ALOX12$^{+/+}$ or hFcR/ALOX12$^{-/-}$ mice (n=3-6 per group). *P<0.05

(FIG. 15A) Immunoprecipitation of FcγRIIa at 15, 30, and 60 seconds post crosslinking and measured for phosphorylation via Western blot. (FIG. 15B) Platelets were lysed following FcγRIIa cross-linking in the presence of ML355 or DMSO were immunoblotted for active (pY323) and total Syk.

(FIG. 16A) A time course of PLCγ2 activation Western blot in which platelets stimulated with antibody crosslinking were stopped at 15, 30, 60, and 300 seconds. Samples of active PLCγ2 activation were analyzed for Y759 phosphorylation by Western blotting. All samples were normalized to total PLCγ2 and fold changes were quantified relative to the unstimulated condition. (FIG. 16B) Following crosslinking with IV.3 and GAM, calcium mobilization was measured by flow cytometry. Representative curves were quantitated in fold change of free calcium relative to the unstimulated condition over four minutes. Bar graphs represent the ratio of the calcium mobilization fold change. (FIG. 16C) Stimulated washed human platelets with or without 12-LOX inhibition were analyzed for PKC activity. A PKC substrate was blotted as a surrogate for PKC activation and Pleckstrin. Quantification of Pleckstrin phosphorylation is shown in the right panel. Data represents mean±S.E.M. *P<0.05; **P<0.01.

DETAILED DESCRIPTION OF THE INVENTION

Figures 1A, 1B, 1C, 1D:
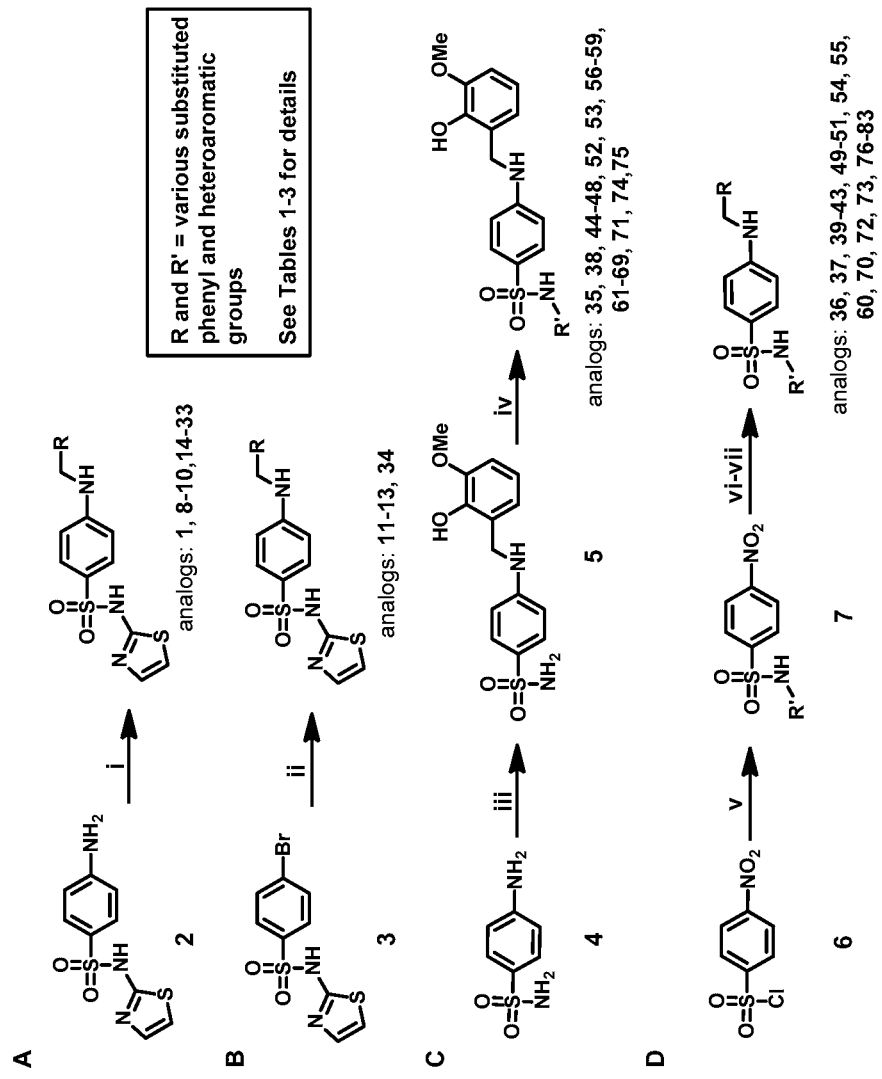
FIGS. 1A-1D. Show the reaction scheme for the synthesis of the analogs of the present invention.

It is understood that the present invention is not limited to the particular methodologies, etc. described herein, as these may vary. It is also to be understood that the terminology used herein is used for the purpose of describing particular embodiments only, and is not intended to limit the scope of the present invention.

In the description, the following terms are employed: LOX is lipoxygenase; 15-LOX-1 is human reticulocyte 15-lipoxygenase-1; 15-LOX-2 is human epithelial 15-lipoxygenase-2; 12-LOX is human platelet 12-lipoxygenase; COX is Cyclooxygenase; NDGA is nordihydroguaiaretic acid; AA is arachidonic acid; 12-HPETE is 12-(S)-hydroperoxyeicosatetraenoic acid; 12-HETE is 12-(S)-hydroxyeicosatetraenoic acid; LA is linoleic acid; $V_{max}$ is maximal velocity (mmol/min); $K_M$ is Henri-Michaelis-Menten Constant; [E] is total active enzyme concentration; $IC_{50}$ is inhibitor constant at 50% inhibition; HTS is high-throughput screening; qHTS is quantitative high-throughput screening; PAR-4 is protease-activated receptor-4; EtOH is ethanol; MeOH is methanol; EtOAc is ethyl acetate; AcOH is acetic acid; MW is microwave; Xantphos is 4,5-bis(diphenylphosphino)-9,9-dimethylxanthene; and SD is standard deviation.

For therapeutic use, "salts" of the compounds of the present invention will be physiologically acceptable, i.e., the salts will be derived from a physiologically acceptable acid or base. Salts of acids or bases, however, which are not physiologically acceptable may also find use in the preparation or purification of a physiologically acceptable compound. Thus, all salts, whether or not derived form a physiologically acceptable acid or base, are within the scope of the present invention.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "pharmaceutically acceptable carrier," as used herein, refers to any and all solvents, dispersion media, coatings, antibacterial and antifungal agent, isotonic and absorption delaying agents for pharmaceutical active substances as are well known in the art. Except insofar as any conventional media or agent is incompatible with the compound, its use in the therapeutic compositions is contemplated. Supplementary compounds can also be incorporated into the compositions.

The expression "therapeutically effective amount" refers to an amount of a compound disclosed herein, that is effective for preventing, ameliorating, treating or delaying the onset of a disease or condition. The expression "prophylactically effective amount" refers to an amount of a compound disclosed herein, that is effective for inhibiting the onset or progression of a disorder.

"Alkyl" is C1-C6 hydrocarbon containing normal, secondary, tertiary or cyclic carbon atoms. Examples include, but are not limited to, methyl, ethyl, propyl, isopropyl, tert-butyl, and the like.

"Alkenyl" is C2-C6 hydrocarbon containing normal, secondary, tertiary or cyclic carbon atoms with at least one site of unsaturation, i.e. a carbon-carbon, sp2 double bond. Examples include, but are not limited to, ethylene or vinyl (—CH═CH2), allyl (—CH2CH═CH2), cyclopentenyl (—C5H7), and 5-hexenyl (—CH2CH2CH2CH2CH═CH2), and the like.

"Alkynyl" is C2-C6 hydrocarbon containing normal, secondary, tertiary or cyclic carbon atoms with at least one site of unsaturation, i.e., a carbon-carbon, sp triple bond. Examples include, but are not limited to, acetylenic (—C≡—CH) and propargyl (—CH2C≡CH), and the like.

"Cycloalkyl" is a saturated, unsaturated or aromatic ring system containing from, for example, 3 to 8 carbon atoms, preferably 3 to 7 carbon atoms, and more preferably 3 to 6 carbon atoms. Examples include, but are not limited to, cyclopentenyl and cyclohexenyl. The cyclic alkyl groups may be unsubstituted or further substituted.

"Heterocycloalkyl" means a saturated, unsaturated or aromatic ring system including at least one N, O, S, or P. Heterocycle thus includes heteroaryl groups. Heterocycle as used herein includes, but is not limited to heterocycles described in PAQUETTE, PRINCIPLES OF MODERN HETEROCYCLIC CHEMISTRY (W. A. Benjamin, New York, 1968), particularly Chapters 1, 3, 4, 6, 7, and 9; THE CHEMISTRY OF HETEROCYCLIC COMPOUNDS, A SERIES OF MONOGRAPHS (John Wiley & Sons, New York, 1950 to present), in particular Volumes 13, 14, 16, 19, and 28; KATRITZKY ET AL., COMPREHENSIVE HETEROCYCLIC CHEMISTRY (Pergamon Press, 1996); and 82 J. AM. CHEM. SOC. 5566 (1960). Heterocycles include, but are not limited to pyridyl, dihydroypyridyl, tetrahydropyridyl (piperidyl), tbiazolyl, tetrahydrothiophenyl, sulfur oxidized tetrahydrotbiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydroturanyl, bis-tetrahydroruranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, beta-carbolinyl, phenanthridinyl, acridinyl, pyrimidinyl, phenanthrolinyl, phenazinyl, phenothiazinyl, rurazanyl, phenoxazinyl, isochromanyl, chromanyl, imidazolidinyl, imidazolinyl, pyrazolidinyl, pyrazolinyl, piperazinyl, indolinyl, isoindolinyl, quimiclidinyl, morpholinyl, oxazolidinyl, benzotriazolyl, benzisoxazolyl, oxindolyl, benzoxazolinyl, and isatinoyl.

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" means a monovalent aromatic radical of one or more carbon atoms and one or more atoms selected from N, O, S, or P, derived by the removal of one hydrogen atom from a single atom of a parent aromatic ring system. Heteroaryl groups may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). Heteroaryl bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The heteroaryl group may be bonded to the drug scaffold through a carbon, nitrogen, sulfur, phosphorus or other atom by a stable covalent bond. Heteroaryl groups include, but are not limited to, pyridyl, dihydropyridyl isomers, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

Unless defined otherwise, all technical and scientific terms used herein have the same meanings as commonly understood by one of ordinary skill in the art to which this invention belongs. Preferred methods and compositions are described, although any methods and compositions similar or equivalent to those described herein can be used in the practice or testing of the present invention.

In one aspect, the present invention includes a compound of Formula (I):

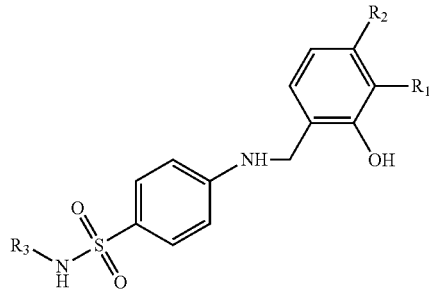

wherein $R_1$ and $R_2$ are independently selected from the group consisting of H, alkyl, alkenyl, alkynyl, F, Cl, Br, amine, nitrogen dioxide, indole, alkoxy, cycloalkyl, aryl, heterocycloalkyl, heteroaryl, each optionally substituted with one or more substituents selected from the group consisting of $C_1$-$C_6$ alkyl, $C_1$-$C_6$ alkenyl, $C_1$-$C_6$ alkynyl, F, Cl, Br, hydroxyl, amine, methoxy;

$R_3$ is selected from the group consisting of phenyl, cycloalkyl, heterocycloalkyl, aryl, heteroaryl, thiazole, benzothiazole, benzoxazole, imidazole, benzimidazole, thiophene, 1-naphthalene, 2-naphthalene, pyridine, quinoline, isoquinoline, 4N-boc-piperidine-3-phenyl, oxazole, benzothiophene, parathiazine, furan, pyran, chromene, benzofuran, pyrrole, pyrazole, pyrazine, pyrimidine, triazine, indole, purine, phthalazine; each optionally substituted with one or more substituents selected from the group consisting of $C_1$-$C_6$ alkyl, $C_1$-$C_6$ alkenyl, $C_1$-$C_6$ alkynyl, F, Cl, Br, hydroxyl, amine, alkoxy, phenyl, cycloalkyl, aryl, piperazine, piperidine, pyridine, morpholine, pyrrolidine, pyrazolidine, imidazolidine, and thiomorpholine;

or a pharmaceutically acceptable salt thereof, enantiomers thereof, a mixture of enantiomers thereof, or diastereomers thereof; with the proviso that the compound is not

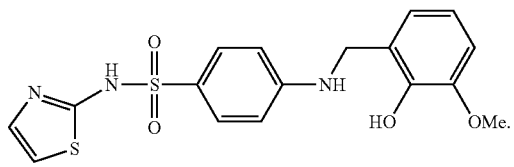

In one embodiment $R_1$ is selected from the group consisting of methoxy and Cl when $R_2$ is H; $R_2$ is selected from the group consisting of Br, and Cl when $R_1$ is H; and $R_3$ is selected from the group consisting of thiazole, 2-benzothiazole, 2-benzoxazole, 2-benzimidazole, 4-methyl-2-benzothiazole, thiophene, 4-methyl-2-thiazole, 5-methyl-2-thiazole, 4, 5-methyl-2-thiazole, phenyl, 1-naphthalene, 2-naphthalene, 1, 4-bi-phenyl, 3-piperazine-phenyl, 4-piperidine-phenyl, 4-piperazine-3-pyridine, 6-methyl-3-pyridine, 3-quinoline, 8-isoquinoline, 2-pyridine, 3-pyridine, 3-tertbutyl-phenyl, 6-methoxy-2-benzothiazole, 6-fluro-2-benzothiazole, 4-phenyl-2-thiazole, 3-morpholine-phenyl, 4N-boc-piperidine-3-phenyl, 3-piperidine-phenyl, 3-isopropyl-phenyl, and 4-bi-phenyl; or a pharmaceutically acceptable salt thereof, enantiomers thereof, a mixture of enantiomers thereof, or diastereomers thereof.

In any of the above embodiments of Formula (I), $R_1$ is methoxy and $R_2$ is H.

In any of the above embodiments of Formula (I), the compound is a pro-drug.

In one embodiment of Formula (I), $R_3$ is selected from the group consisting of 2-benzothiazole, 2-benzoxazole, 2-benzimidazole, 4-methyl-2-benzothiazole, 3-quinoline, 8-isoquinoline, phenyl, and 3-isopropyl-phenyl.

In one embodiment of Formula (I), $R_3$ is selected from the group consisting of 2-benzothiazole, 2-benzoxazole, 2-benzimidazole, 4-methyl-2-benzothiazole, thiophene, phenyl, 1-naphthalene, 2-naphthalene, 3-quinoline, 8-isoquinoline, 3-tertbutyl-phenyl, 6-methoxy-2-benzothiazole, 6-fluro-2-benzothiazole, 4-phenyl-2-thiazole, 4N-boc-piperidine-3-phenyl, and 3-isopropyl-phenyl.

In one embodiment of Formula (I), $R_3$ is selected from the group consisting of 2-benzothiazole, 2-benzoxazole, 2-benzimidazole, 4-methyl-2-benzothiazole, thiophene, phenyl, 1-naphthalene, 2-naphthalene, 3-quinoline, 8-isoquinoline, 3-tertbutyl-phenyl, 4N-boc-piperidine-3-phenyl, and 3-isopropyl-phenyl.

In one embodiment of Formula (I), $R_3$ is selected from the group consisting of 2-benzothiazole, 2-benzoxazole, 2-benzimidazole, and 3-isopropyl-phenyl.

In one embodiment of Formula (I), $R_3$ is selected from the group consisting of 2-benzothiazole, 2-benzoxazole, 2-benzimidazole, 4-methyl-2-benzothiazole, thiophene, phenyl, 6-methoxy-2-benzothiazole, 6-fluro-2-benzothiazole, and 4-phenyl-2-thiazole.

In one embodiment of Formula (I), $R_3$ is selected from the group consisting of 2-benzothiazole, 2-benzoxazole, 2-benzimidazole, 4-methyl-2-benzothiazole, thiophene, and phenyl.

In one embodiment of Formula (I), $R_3$ is selected from the group consisting of 2-benzothiazole, 2-benzoxazole, 2-benzimidazole, 4-methyl-2-benzothiazole, thiophene, phenyl, 1-naphthalene, 2-naphthalene, 3-quinoline, 8-isoquinoline, 2-pyridine, and 3-pyridine.

In one embodiment the compound of formula (I) is

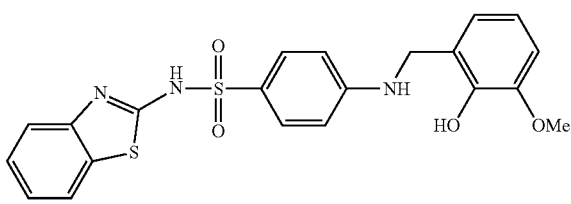

or a pharmaceutically acceptable salt thereof, enantiomers thereof, a mixture of enantiomers thereof, or diastereomers thereof. This is ML355 (compound 35).

In one embodiment the compound of formula (I) is

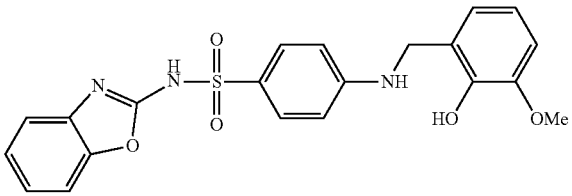 [SMILES: COc1cccc(CNc2ccc(S(=O)(=O)Nc3nc4ccccc4s3)cc2)c1O]

or a pharmaceutically acceptable salt thereof, enantiomers thereof, a mixture of enantiomers thereof, or diastereomers thereof.

In one embodiment the compound of formula (I) is

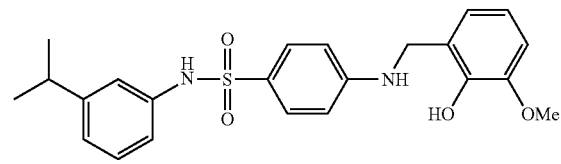 [SMILES: COc1cccc(CNc2ccc(S(=O)(=O)Nc3cccc(C(C)C)c3)cc2)c1O]

or a pharmaceutically acceptable salt thereof, enantiomers thereof, a mixture of enantiomers thereof, or diastereomers thereof.

In another aspect, the present invention includes a compound of Formula (II):

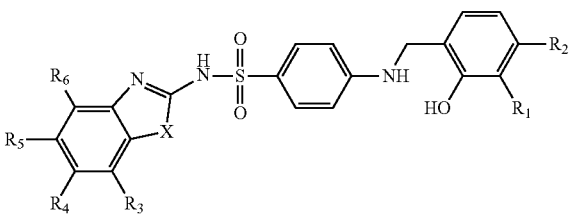

wherein X is selected from the group consisting of O, S, NH, and C;

wherein $R_1$ and $R_2$ are independently selected from the group consisting of H, halogen, hydroxyl, alkoxy, and alkyl;

wherein $R_3$ through $R_6$ are independently selected from the group consisting of H, halogen, alkoxy, and alkyl;

or a pharmaceutically acceptable salt thereof, enantiomers thereof, a mixture of enantiomers thereof, or diastereomers thereof.

In another aspect, the present invention includes a compound of Formula (III):

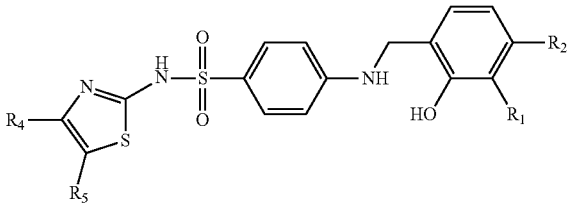

wherein $R_1$ and $R_2$ are independently selected from the group consisting of H, halogen, and alkoxy, and further wherein $R_1$ and $R_2$ are not both H;

wherein $R_4$ and $R_5$ are independently selected from the group consisting of H, alkyl, phenyl, and optionally substituted phenyl;

or a pharmaceutically acceptable salt thereof, enantiomers thereof, a mixture of enantiomers thereof, or diastereomers thereof;

with the proviso that the compound is not

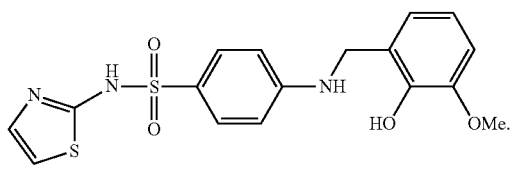 [SMILES: COc1cccc(CNc2ccc(S(=O)(=O)Nc3nccs3)cc2)c1O]

In one embodiment, $R_1$ is not a halogen.
In one embodiment, $R_1$ is not F.
In one embodiment, $R_1$ is not Br.
In one embodiment, when $R_1$ is H, $R_2$ is not methoxy.
In one embodiment, $R_5$ is not phenyl.
In one embodiment, when $R_4$ is H, $R_5$ is not phenyl.

In another aspect, the present invention includes a compound of Formula (IV):

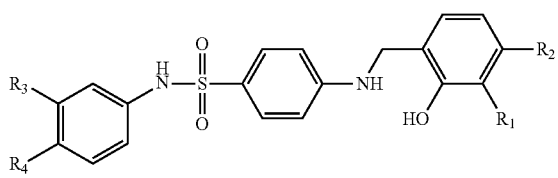

wherein $R_1$ and $R_2$ are independently selected from the group consisting of H, halogen, and alkoxy;

wherein $R_3$ and $R_4$ are independently selected from the group consisting of H, phenyl, optionally substituted phenyl, tert-butyl, isopropyl, and

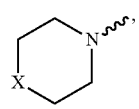

wherein X is selected from the group consisting of NH, O, and

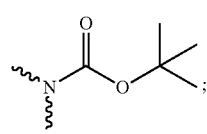

or a pharmaceutically acceptable salt thereof, enantiomers thereof, a mixture of enantiomers thereof, or diastereomers thereof.

In one embodiment, when $R_4$ is

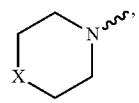

X is not NH.

In one embodiment, $R_3$ is not phenyl.
In one embodiment, when $R_4$ is H, $R_3$ is not phenyl.

In another aspect, the present invention includes a compound of Formula (V):

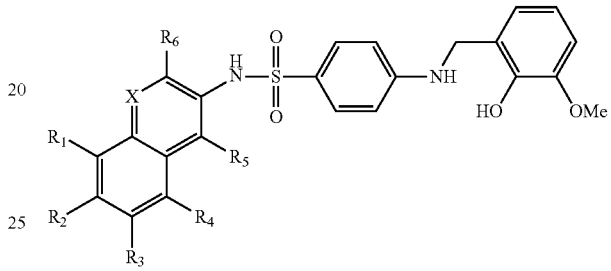

wherein X is selected from the group consisting of N, C, S, and O;

wherein $R_1$ through $R_6$ are independently selected from the group consisting of H, alkyl, and alkoxy;

or a pharmaceutically acceptable salt thereof, enantiomers thereof, a mixture of enantiomers thereof, or diastereomers thereof.

In one embodiment, X is C and $R_1$ through $R_6$ are H.
In one embodiment, X is N and $R_1$ through $R_6$ are H.

In another aspect, the present invention includes a compound of Formula (VI):

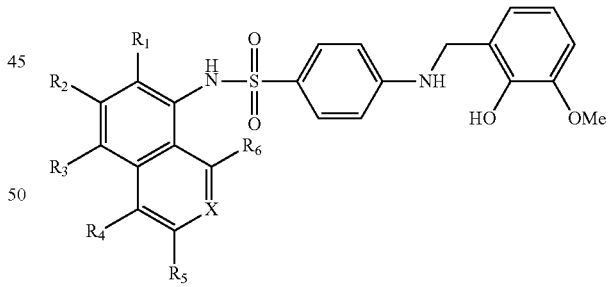

wherein X is selected from the group consisting of N, C, S, and O;

wherein $R_1$ through $R_6$ are independently selected from the group consisting of H, alkyl, and alkoxy;

or a pharmaceutically acceptable salt thereof, enantiomers thereof, a mixture of enantiomers thereof, or diastereomers thereof.

In one embodiment, X is C and $R_1$ through $R_6$ are H.
In one embodiment, X is N and $R_1$ through $R_6$ are H.

In another aspect, the present invention includes a compound of Formula (VII):

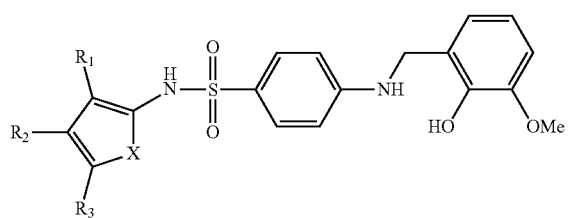

wherein X is selected from the group consisting of N, C, S, and O;

wherein $R_1$ through $R_3$ are independently selected from the group consisting of H, alkyl, and alkoxy;

or a pharmaceutically acceptable salt thereof, enantiomers thereof, a mixture of enantiomers thereof, or diastereomers thereof.

In one embodiment, X is S and $R_1$ through $R_3$ are H.

In any of the above embodiments, the compound or salt of Formulas (I)-(VII) includes each diastereomer, optical isomer, enantiomer and the racemic mixtures.

It is further understood that the above compounds and salts may form solvates, or exist in a substantially uncomplexed form, such as the anhydrous form. When the solvent incorporated in the solvate is water, the molecular complex is a hydrate. Pharmaceutically acceptable solvates include hydrates, alcoholates such as methanolates and ethanolates, acetonitrilates and the like. These compounds can also exist in polymorphic forms.

The present invention is further directed to a pharmaceutical composition comprising a pharmaceutically acceptable carrier and at least one compound of Formula (I)-(VII) described herein.

Routes of administration and dosages of effective amounts of the pharmaceutical compositions comprising the compounds are also disclosed. The compounds of the present invention can be administered in combination with other pharmaceutical agents in a variety of protocols for effective treatment of disease.

The pharmaceutical compositions of the inventions can be administered to any animal that can experience the beneficial effects of the compounds of the invention. Such animals include humans and non-humans such as pets and farm animals.

The pharmaceutical compositions of the present invention are administered to a subject in a manner known in the art. The dosage administered will be dependent upon the age, health, and weight of the recipient, kind of concurrent treatment, if any, frequency of treatment, and the nature of the effect desired.

In addition to the compounds disclosed herein, the pharmaceutical compositions of the present invention may further comprise at least one of any suitable auxiliaries including, but not limited to, diluents, binders, stabilizers, buffers, salts, lipophilic solvents, preservatives, adjuvants or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical excipients and additives useful in the present invention can also include, but are not limited to, proteins, peptides, amino acids, lipids, and carbohydrates (e.g., sugars, including monosaccharides, di-, tri-, terra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

The composition further can contain, but is not limited to pharmaceutically acceptable carriers such as coloring agents, emulsifying agents, suspending agents, ethanol, EDTA, citrate buffer, flavoring, and water.

The composition of the invention also can contain the preservatives methylparaben (also known as 4-hydroxybenzoic acid methyl ester, methyl p-hydroxybenzoate; or METHYL CHEMOSEPT), ethylparaben (also known as 4-hydroxybenzoic acid ethyl ester; ethyl p-hydroxybenzoate; or ETHYL PARASEPT), propylparaben (also known as 4-hydroxybenzoic acid propyl ester; propylp-hydroxybenzoate; NIPASOL; or PROPYL CHEMOSEPT) and/or butylparaben (also known as 4-hydroxybenzoic acid propyl ester; propyl p-hydroxybenzoate; or BUTYL CHEMOSEPT). In some embodiments, the composition contains methylparaben and/or propylparaben.

Emulsifiers of the invention include, but are not limited to ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, tetrahydrofurfuryl alcohol, polyethylene glycols and fatty acid esters of sorbitan, and mixtures thereof.

The pharmaceutical compositions comprising the compounds of the present invention can also include a buffer or a pH adjusting agent Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the pharmaceutical compositions of the invention can include polymeric excipients/additives such as polyvinylpyrrolidones, ficolls (a polymeric sugar), dextrates (e.g.; cyclodextrins, such as 2-hydroxypropyl-.beta.-cyclodextrin), polyethylene glycols, flavoring agents, anti-microbial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA or EGTA). These and additional known pharmaceutical excipients and/or additives suitable for use in the present invention are known in the art, e.g., as listed in REMINGTON: THE SCIENCE & PRACTICE OF PHARMACY ($19^{th}$ ed., Williams & Williams (1995)) and PHYSICIAN'S DESK REFERENCE ($52^{nd}$ ed., Medical Economics (1998)), the disclosures of which are expressly entirely incorporated herein by reference.

The present invention provides stable pharmaceutical compositions as well as preserved solutions and compositions containing a preservative, as well as multi-use preserved compositions suitable for pharmaceutical or veterinary use, comprising at least one compound disclosed herein in a pharmaceutically acceptable composition. Pharmaceutical compositions in accordance with the present invention may optionally contain at least one known preservative. Preservatives include, but are not limited to, phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein. Non-limiting examples include, no preservative, 0.1-2% m-cresol, 0.1-3% benzyl alcohol, 0.001-0.5% thimerosal, 0.001-2.0% pheno, 0.0005-1.0% alkylparaben (s), and the like.

Other excipients, e.g., isotonicity agents, buffers, antioxidants, preservative enhancers, can be optionally added to the diluent. An isotonicity agent such as glycerin, is commonly used at known concentrations. A physiologically tolerated buffer is preferably added to provide improved pH control. The pharmaceutical compositions can cover a wide range of pHs, such as from about pH 4 to about pH 10, specifically, a range from about pH 5 to about pH 9, and more specifically, a range of about 6.0 to about 8.0. In one aspect, the formulations of the present invention have pH between about 6.8 and about 7.8. Suitable buffers include phosphate buffers, sodium phosphate and phosphate buffered saline (PBS).

Other additives, such as a pharmaceutically acceptable solubilizers like Tween 20 (polyoxyethylene (20) sorbitan monolaurate), TWEEN 40 (polyoxyethylene (20) sorbitan monopahnitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, PLURONIC® polyls, other block copolymers, and chelators such as EDTA and EGTA can optionally be added to the pharmaceutical compositions to reduce aggregation. These additives are particularly useful if a pump or plastic container is used to administer the pharmaceutical composition. The presence of pharmaceutically acceptable surfactant mitigates the propensity for the composition to aggregate.

The composition of the invention also can contain the preservatives methylparaben (also known as 4-hydroxybenzoic acid methyl ester; methyl p-hydroxybenzoate; or METHYL CHEMOSEPT), ethylparaben (also known as 4-hydroxybenzoic acid ethyl ester; ethyl p-hydroxybenzoate; or ETHYL PARASEPT), propylparaben (also known as 4-hydroxybenzoic acid propyl ester; propyl p-hydroxybenzoate; NIPASOL; or PROPYL CHEMOSEPT) and/or butylparaben (also known as 4-hydroxybenzoic acid propyl ester, propyl p-hydroxybenzoate; or BUTYL CHEMOSEPT). In some embodiments, the composition contains methylparaben and/or propylparaben.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see Prescott, ed., METH. CELL BIOL. 14:33 (1976)). Liposomes, methods of making and methods of use are described in U.S. Pat. No. 4,089, 8091 (process for the preparation of liposomes), U.S. Pat. No. 4,233,871 (methods regarding biologically active materials in lipid vescicles), U.S. Pat. No. 4,438,052 (process for producing mixed miscelles), U.S. Pat. No. 4,485,054 (large multilamellar vescisles), U.S. Pat. No. 4,532,089 (giant-sized liposomes and methods thereof), U.S. Pat. No. 4,897, 269 (liposomal drag delivery system), U.S. Pat. No. 5,820, 880 (liposomal formulations), and so forth.

During any of the processes for preparation of the compounds of the present invention, it may be necessary and/or desirable to protect sensitive or reactive groups on any of the molecules concerned. This may be achieved by means of conventional protecting groups, such as those described in PROTECTIVE GROUPS IN ORGANIC CHEMISTRY (1973); and GREENE AND WUTS, PROTECTIVE GROUPS IN ORGANIC SYNTHESIS (1991). The protecting groups may be removed at a convenient subsequent stage using methods known from the art.

The compound of the invention can be solubilized or suspended in a preconcentrate (before dilutions with a diluent), added to the preconcentrate prior to dilution, added to the diluted preconcentrate, or added to a diluent prior to mixing with the preconcentrate. The compound of the invention can also be co-administered as part of an independent dosage form, for therapeutic effect. Optionally, the compound of the invention can be present in a first, solubilized amount, and a second, non-solubilized (suspended) amount The pharmaceutical formulation can also contain suitable pharmaceutically acceptable carriers comprising excipients and auxiliaries that facilitate processing of the active compounds into preparations that can be administered to animals, as described herein.

For oral administration in the form of a tablet or capsule, a compound may be combined with an oral, non-toxic pharmaceutically acceptable inert carrier such as ethanol, glycerol, water and the like. Moreover, when desired or necessary, suitable binders, lubricants, disintegrating agents, and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For oral administration, the composition also optionally contains a sweetener. Sweeteners include but are not limited to sucrose, fructose, sodium saccharin, sucralose (SPLENDA®), sorbitol, mannitol, aspartame, sodium cyclamate, and the like and combinations thereof.

The aqueous suspensions, emulsions and/or elixirs for oral administration of this invention can be combined with various sweetening agents, flavoring agents, such as, but not limited to orange or lemon flavors, coloring agents, such as dye stuffs, natural coloring agents or pigments, in addition to the diluents such as water, glycerin and various combinations, as described herein.

The pharmaceutical compositions of the present invention suitable for oral administration may be presented as discrete units such as capsules, dragees, cachets or tablets each containing a predetermined amount of the compound; as a powder or granules; as a solution or a suspension in an aqueous liquid or a non-aqueous liquid; or as an oil-in-water liquid emulsion or a water-in-oil emulsion, and as a bolus, etc.

A tablet may be made by compression or molding, optionally with one or more accessory ingredients. Compressed tablets may be prepared by compressing, in a suitable machine, the compound in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the compound therein.

In addition, the compositions comprising compounds may be incorporated into biodegradable polymers allowing for sustained release of the compound. The biodegradable polymers and their uses are described in detail in Brem et al., 74 J. NEUROSURG. 441-46 (1991). Suitable examples of sustained-release compositions include semipermeable matrices of solid hydrophobic polymers containing a compound of the present invention, which matrices are in the form of shaped articles, e.g., films, or microcapsules. Examples of sustained-release matrices include polyesters, hydrogels (including poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(−)-3-hydroxybutyric acid.

Pharmaceutical compositions suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The compositions may be presented in unit-dose or multi-dose containers, sealed ampules and vials, and may be stored in a freeze-dried (lyophilized) condition requiring only the addition of the sterile liquid carrier, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous, administration is desired. The pharmaceutical compositions may be administered parenterally via injection of a pharmaceutical composition comprising a compound dissolved in an inert liquid carrier. The term "parenteral," as used herein, includes, but is not limited to, subcutaneous injections, intravenous, intramuscular, intraperitoneal injections, or infusion techniques. Acceptable liquid carriers include, vegetable oils such as peanut oil, cotton seed oil, sesame oil and the like, as well as organic solvents such as solketal, glycerol formal and the like. The pharmaceutical compositions may be prepared by dissolving or suspending the compound in the liquid carrier such that the final formulation contains from about 0.005% to 30% by weight of a compound.

The composition of the invention can also include additional therapeutic agents such as, but not limited to hydrophilic drugs, hydrophobic drugs, hydrophilic macromolecules, cytokines, peptidomimetics, peptides, proteins, toxoids, sera, antibodies, vaccines, nucleosides, nucleotides, nucleoside analogs, genetic materials and/or combinations thereof.

The additional therapeutic agent can be solubilized or suspended in a preconcentrate (before dilutions with a diluent), added to the preconcentrate prior to dilution, added to the diluted preconcentrate, or added to a diluent prior to mixing with the preconcentrate. The additional therapeutic agent can also be co-administered as part of an independent dosage form, for therapeutic effect. Optionally, the additional therapeutic agent(s) can be present in a first, solubilized amount, and a second, non-solubilized (suspended) amount Such additional therapeutic agent(s) can be any agent(s) having therapeutic or other value when administered to an animal, particularly to a mammal, such as drags, nutrients, and diagnostic agents.

In addition to the compound and compositions of the invention, and additional pharmaceutically active agents, the pharmaceutical formulation can also contain suitable pharmaceutically acceptable carriers comprising excipients and auxiliaries that facilitate processing of the active compounds into preparations mat can be administered to animals, as described herein.

Pharmaceutical formulations useful in the present invention can contain a quantity of a compound(s) according to this invention in an amount effective to treat or prevent the condition, disorder or disease of the subject being treated.

The invention further relates to the administration of at least one compound disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarenal, intraretinal, intraspinal, intrasynovial, intrathoracic, intrauterine, intravesical, bolus, vaginal, rectal, buccal, sublingual, intranasal, iontophoretic means, or transdermal means.

It can be sometimes desirable to deliver the compounds of the present invention to the subject over prolonged periods of time, for periods of one week to one year from a single administration. Certain medical devices may be employed to provide a continuous intermittent or on demand dosing of a patient. The devices may be a pump of diffusion apparatus, or other device containing a reservoir of drug and optionally diagnostic or monitoring components to regulate the delivery of the drug. Various slow-release, depot or implant dosage forms can be utilized. A dosage form can contain a pharmaceutically acceptable non-toxic salt of a compound disclosed herein that has a low degree of solubility in body fluids, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, the compounds of the present invention or a relatively insoluble salt such as those just described, can be formulated in a gel, an aluminum monostearate gel with, e.g., sesame oil, suitable for injection. Salts include, but are not limited to, zinc salts, zinc tannate salts, pamoate salts, and the like. Another type of slow-release depot formulation for injection would contain the compound of salt dispersed or encapsulated in a slow degrading, non-toxic, non-antigenic polymer such as a polylactic acid/polyglycolic acid polymer, including the formulations as described in U.S. Pat. No. 3,773,919. The compounds or relatively insoluble salts thereof such as those described above can also be formulated in cholesterol matrix silastic pellets, particularly for use in animals. Additional slow-release, depot or implant formulations, e.g., gas or liquid liposomes are known in the literature. See, e.g., U.S. Pat. No. 5,770,222; SUSTAINED AND CONTROLLED RELEASE DRUG DELIVERY SYSTEMS (1978).

Other examples include provision of the compounds of the present invention to be administered by sustained release delivery system containing a biodegradable composition. The biodegradable composition may be composed of a biodegradable, water-coagulable, non-polymeric material and a biocompatible, non-toxic organic solvent that is miscible to dispersible in an aqueous medium. The delivery system may be implanted at an implant site causing the solvent to dissipate, disperse or leach from the composition into surrounding tissue fluid through a resulting microporous matrix.

The term "implant site" is meant to include a site, in or on which the non-polymeric composition is applied. Implantation or implant site can also include the incorporation of the pharmaceutical composition comprising at least one compound of the present invention with a solid device. The pharmaceutical composition can be incorporated into a coating on a stent that is implanted into a subject. Additionally, other solid or biodegradeable materials can be used as a substrate on which the pharmaceutical composition is applied. The coated material, comprising the pharmaceutical composition is then implanted, inserted or is adjacent to the subject or patient. The term "biodegradable" means that the non-polymeric material and/or matrix of the implant will degrade over time by the action of enzymes, by simple or enzymatically catalyzed hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, by a cell, a tissue, and the like.

Non-polymeric materials that can be used in the composition generally are those that are biocompatible, substantially insoluble in water and body fluids, and biodegradable and/or bioerodible. The non-polymeric material is capable of being at least partially solubilized in a water-soluble organic solvent. The non-polymeric materials are also capable of coagulating or solidifying to form a solid implant matrix. The non-polymeric material is combined with a compatible and suitable organic solvent to form a composition that has the desired consistency ranging from watery to viscous to a spreadable putty or paste.

Suitable organic solvents are those that are biocompatible, pharmaceutically-acceptable, and will at least partially dissolve the non-polymeric material. The organic solvent has a solubility in water ranging from miscible to dispersible. Optionally, a pore-forming agent can be included in the composition to generate additional pores in the implant matrix. The pore-forming agent can be any organic or inorganic, pharmaceutically-acceptable substance that is substantially soluble in water or body fluid, and will dissipate from the coagulating non-polymeric material and/or the solid matrix of the implant into surrounding body fluid at the implant site.

The compounds of the present invention are capable of providing a local or systemic biological, physiological or therapeutic effect in the body of an animal. In formulating some pharmaceutical compositions described herein, the compound is preferably soluble or dispersible in the non-polymeric composition to form a homogeneous mixture, and upon implantation, becomes incorporated into the implant matrix. As the solid matrix degrades over time, the compound is capable of being released from the matrix into the adjacent tissue fluid, and to the pertinent body tissue or organ, either adjacent to or distant from the implant site, preferably at a controlled rate. The release of the compound from the matrix may be varied by the solubility of the compound in an aqueous medium, the distribution of the compound within the matrix, the size, shape, porosity, and solubility and biodegradability of the solid matrix. See e.g., U.S. Pat. No. 5,888,533. The amounts and concentrations of ingredients in the composition administered to the patient will generally be effective to accomplish the task intended.

In other embodiments, the compounds of the present invention may be administered by bioactive agent delivery systems containing microparticles suspended in a polymer matrix. The microparticles may be microcapsules, microspheres or nanospheres currently known in the art. The microparticles should be capable of being entrained intact within a polymer that is or becomes a gel once inside a biological environment. The microparticles can be biodegradable or non-biodegradable. Many microencapsulation techniques used to incorporate a bioactive agent into a microparticle carrier are taught in the art. See e.g., U.S. Pat. Nos. 4,652,441; 5,100,669; 4,438,253; and 5,665,428.

A preferred polymeric matrix will be biodegradable and exhibit water solubility at low temperature and will undergo reversible thermal gelation at physiological mammalian body temperatures. The polymeric matrix is capable of releasing the substance entrained within its matrix over time and in a controlled manner. The polymers are gradually degraded by enzymatic or non-enzymatic hydrolysis in aqueous or physiological environments. See e.g., U.S. Pat. No. 6,287,588.

Methods of preparing various pharmaceutical compositions with a certain amount of active ingredients are known, or will be apparent in light of this disclosure, to those skilled in the art. Methods of preparing said pharmaceutical compositions can incorporate other suitable pharmaceutical excipients and their formulations as described in REMINGTON'S PHARMACEUTICAL SCIENCES, Martin, E. W., ed., Mack Publishing Company, 19th ed. (1995).

Methods of preparing the pharmaceutical preparations of the present invention are manufactured in a manner that is known, including conventional mixing, dissolving, or lyophilizing processes. Thus, liquid pharmaceutical preparations can be obtained by combining the active compounds with solid excipients, optionally grinding the resulting mixture and processing the mixture of granules, after adding suitable auxiliaries, if desired or necessary.

One of ordinary skill in the art will appreciate that a method of administering pharmaceutically effective amounts of the compositions of the invention to a patient in need thereof, can be determined empirically, or by standards currently recognized in the medical arts. The agents can be administered to a patient as pharmaceutical compositions in combination with one or more pharmaceutically acceptable excipients. It will be understood that, when administered to a human patient, the total daily usage of the agents of the compositions of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, gender and diet of the patient; the time of administration, route of administration, and rate of excretion of the agent; the duration of the treatment; drugs used in combination or coincidental with the specific agent; and like factors well known in the medical arts. It is well within the skill of the art to start doses of the agents at levels lower than those required to achieve the desired therapeutic effect and to gradually increase the dosages until the desired effect is achieved.

Dosaging can also be administered in a patient-specific manner to provide a predetermined concentration of the agents in the blood, as determined by techniques accepted and routine in the art.

In general, the compounds disclosed herein may be used alone or in concert with other therapeutic agents at appropriate dosages defined by routine testing in order to obtain optimal efficacy while minimizing any potential toxicity. The dosage regimen utilizing a compound of the present invention may be selected in accordance with a variety of factors including type, species, age, weight, sex, medical condition of the patient; the severity of the condition to be treated; the route of administration; the renal and hepatic function of the patient; and the particular compound employed. A physician or veterinarian of ordinary skill can readily determine and prescribe the effective amount of the drag required to prevent, counter, or arrest the progress of the condition.

Optimal precision in achieving concentrations of drug within the range that yields maximum efficacy with minimal toxicity may require a regimen based on the kinetics of the compound's availability to one or more target sites. Distribution, equilibrium, and elimination of a drug may be considered when determining the optimal concentration for a treatment regimen. The dosages of a compound disclosed herein may be adjusted when combined to achieve desired effects. On the other hand, dosages of these various therapeutic agents may be independently optimized and combined to achieve a synergistic result wherein the pathology is reduced more than it would be if either agent were used alone.

In particular, toxicity and therapeutic efficacy of a compound disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Compounds exhibiting large therapeutic indices are preferred except when cytotoxicity of the compound is the activity or therapeutic outcome that is desired. Although compounds that exhibit toxic side effects may be used, a delivery system can target such compounds to the site of affected tissue in order to minimize potential damage to uninfected cells and, thereby, reduce side effects. Generally, the compounds of the present invention may be administered in a manner that maximizes efficacy and minimizes toxicity.

Data obtained from cell culture assays and animal studies may be used in formulating a range of dosages for use in humans. The dosages of such compounds lies preferably within a range of circulating concentrations that include the $ED_{50}$ with little or no toxicity. The dosage may vary within this range depending upon the dosage form employed and the route of administration utilized. For any compound used in the methods of the present invention, the therapeutically effective dose may be estimated initially from cell culture assays. A dose may be formulated in animal models to achieve a circulating plasma concentration range that includes the $IC_{50}$ (the concentration of the test compound that achieves a half-maximal inhibition of symptoms) as determined in cell culture. Such information may be used to accurately determine useful doses in humans. Levels in plasma may be measured, by high performance liquid chromatography.

Moreover, the dosage administration of the pharmaceutical compositions of the present invention may be optimized using a pharmacokinetic/pharmacodynamic modeling system. One or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See U.S. Pat. No. 6,747,002, which is entirely expressly incorporated herein by reference.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount," as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i e, inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician. Thus, the present invention further provides combinations of two or more therapeutic agents wherein, (a) each therapeutic agent is administered in an independently therapeutically or prophylactically effective amount; (b) at least one therapeutic agent in the combination is administered in an amount that is sub-therapeutic or subprophylactic if administered alone, but is therapeutic or prophylactic when administered in combination with the second or additional therapeutic agents according to the invention; or (c) both therapeutic agents are administered in an amount that is subtherapeutic or subprophylactic if administered alone, but are therapeutic or prophylactic when administered together. Combinations of three or more therapeutic agents are analogously possible. Methods of combination therapy include co-administration of a single formulation containing all active agents; essentially contemporaneous administration of more than one formulation; and administration of two or more active agents separately formulated.

More specifically, the pharmaceutical compositions may be administered in a single daily dose, or the total daily dosage may be administered in divided doses of two, three, or four times daily. Doses maybe administered for one week, one month, or over the course of several months, 3, 6, 9 or 12 months, or intervals known in the art and determined to be clinically relevant. Doses may be continued throughout the life of the patient, or discontinues when clinical judgment warrants. The daily dosage of the compositions may be varied over a wide range from about 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg). Additionally, the dosages may be about 0.5-10 mg/kg per day, about 1.0-5.0 mg/kg per day, 5.0-10 mg/kg per day, or equivalent doses as determine by a practitioner, to achieve a serum concentration that is clinically relevant.

In the case of injections, it is usually convenient to give by an intravenous route in an amount of about 0.01-30 mg, about 0.1-20 mg or about 0.1-10 mg per day to adults (at about 60 kg). Intravenous doses may include a bolus or a slow dosing. In the case of other animals, the dose calculated for 60 kg may be administered as well.

As a non-limiting example, treatment of humans or animals can be provided as a one-time or periodic dosage of a compound of the present invention 0.0001 to about 1,000 mg per patient, per day. The range may more particularly be from about 0.001 mg/kg to 10 mg/kg of body weight per day, about 0.1-100 mg, about 1.0-50 mg or about 1.0-20 mg per day for adults (at about 60 kg). Additionally, the dosages may be about 0.5-10 mg/kg per day, about 1.0-5.0 mg/kg per day, 5.0-10 mg/kg per day, or equivalent doses as determine by a practitioner, to achieve a serum concentration that is clinically relevant.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

The invention further provides a method for treating or preventing a 12-lipoxygenase mediated disease or disorder. The method comprises administering to a mammal a therapeutically or prophylactically effective amount of a compound of the present invention.

The 12-lipoxygenase mediated disease or disorder to be treated or prevented is typically a disease or disorder wherein the production of 12-hydroperoxyeicosatetraenoic acid (12(S)—HPETE) and/or 12-hydroxyeicosatetraenoic acid (12(S)-HETE) is implicated in the development or progression of the disease or disorder. 12-LOX mediated diseases and disorders includes those where 12-LOX is a direct mediator of the diseases and disorders, as well as those where the inhibition of 12-LOX results in therapeutic value in the treatment or prevention of the diseases and disorders.

In one embodiment, the invention provides a method of treating or preventing a 12-lipoxygenase mediated disease or disorder, comprising administering to a mammal thereof a therapeutically or prophylactically effective amount of any of compounds of Formula (I)-(VII), or a salt, enantiomers, a mixture of enantiomers, or diastereomer thereof.

In one embodiment, the 12-lipoxygenase is human the 12-lipoxygenase.

In one embodiment, the 12-lipoxygenase mediated disease or disorder is selected from the group consisting of type 1 diabetes, type 2 diabetes, diabetic kidney disease, diabetic nerve disease, cardiovascular disease, Alzheimer's disease, Non-Alcoholic steatohepatitis, platelet hemostasis, skin diseases, heparin induced thrombocytopenia, thrombosis, and cancer.

In one embodiment, the cancer is selected from the group consisting of prostate cancer, colorectal cancer, breast cancer, and lung cancer.

In one embodiment, the cardiovascular disease is selected from the group consisting of congestive heart failure, myocardial infarction and stroke.

In one embodiment, the invention provides a method of treating or preventing type 1 and/or type 2, comprising administering to a mammal thereof a therapeutically or prophylactically effective amount of any of compounds of Formula (I)-(VII), or a salt, enantiomers, a mixture of enantiomers, or diastereomer thereof.

In one embodiment, the invention provides a method of treating or preventing thrombosis, comprising administering to a mammal thereof a therapeutically or prophylactically effective amount of any of compounds of Formula (I)-(VII), a salt, enantiomers, a mixture of enantiomers, or diastereomer thereof.

In one embodiment, the invention provides a method for reducing PAR4-AP induced platelet aggregation, comprising administering to a mammal thereof a therapeutically or prophylactically effective amount of any of compounds of Formula (I)-(VII), a salt, enantiomers, a mixture of enantiomers, or diastereomer thereof.

In one embodiment, the invention provides a method for reducing PAR4-AP induced calcium mobilization, comprising administering to a mammal thereof a therapeutically or prophylactically effective amount of any of compounds of Formula (I)-(VII), a salt, enantiomers, a mixture of enantiomers, or diastereomer thereof.

In one embodiment, 12-LOX inhibitors have utility in transplantation/xenotransplantation scenarios, for example, where islets are treated ex vivo to improve survival prior to transplant.

The invention is based, in part, on the surprising discovery that platelet 12(S)-lipoxygenase (12-LOX), a highly expressed oxylipin producing enzyme in the human platelet, is an essential component of FcγRIIa-mediated platelet activation. For example, FIG. 11 shows how 12-LOX modulates FcγRIIa-mediated platelet aggregation. Without wishing to be bound by theory, platelets are essential in maintaining hemostasis following inflammation or injury to the vasculature. Activation of the FcγRIIa receptor leads to immune-mediated platelet activation, which can result in thrombotic complications leading to myocardial infarction and stroke. Inhibiting FcγRIIa-mediated activation in platelets has been shown to limit thrombosis and is the principle target for prevention of immune-mediated platelet activation. However, 12-LOX was not known in the art to be implicated in the pathogenesis of FcγRIIa-mediated thrombosis until the inventors' discovery. Accordingly, the technology disclosed herein aims to exploit this surprising discovery and provide novel methods for treating or preventing a disease or disorder in which a FcγRIIa-mediated pathway is involved. Such a disease or disorder can be an immune-mediated thrombocytopenia and thrombosis disorder. In some aspects of the invention, disclosed herein are novel methods for inhibiting platelet activation and preventing or treating thrombosis.

One aspect of the invention relates to a method of inhibiting or decreasing platelet activation, the method comprising contacting a platelet with a 12-lipoxygenase inhibitor. In some embodiments, the platelet activation is immune-mediated. In some embodiments, the immune-mediated platelet activation is resulting from the activation of a FcγRIIa receptor.

A compound or agent is considered a 12-LOX inhibitor if it decreases the function or activity of 12-LOX by at least 10%, at least 20%, at least 30%, at least 40%, at least 50%, at least 60%, at least 70%, at least 80%, at least 90%, or at least 95%. A 12-LOX inhibitor can be an organic compound, an inorganic compound, a biological compound (e.g., proteins or fragments thereof, antibodies or fragments thereof, nucleic acids, nucleic acid analogs, saccharides, or peptides), or any combination thereof. A 12-LOX inhibitor can also be synthetic or naturally occurring. Non-limiting examples of 12-LOX inhibitors include ETYA (CAS No.: 1191-85-1), baicalein (CAS No.: 491-67-8), 15(S)-HETrE (CAS No.: 13222-49-6), caffeic acid (CAS No.: 331-39-5), CDC (CAS No.: 132465-11-3), esculetin (CAS No.: 305-01-1), ethyl 3,4-dihydroxybenzylidenecyanoacetate (CAS No.: 132464-92-7), ETI (CAS No.: 13488-22-7), ferulic acid (CAS No.: 1135-24-6), Gossypol (CAS No.: 303-45-7), 2-TEDC (CAS No.: 132465-10-2), Hinokitiol (CAS No.: 499-44-5), 8,11,14-eicosatriynoic acid (CAS No.: 34262-64-1), daphnodorin A, ML355, and a combination thereof. The chemical structure of ML355 is disclosed in Luci et al. (J Med Chem. 2014, 57, 495-506), the content of which is incorporated by reference in its entirety.

12-LOX inhibitors are also disclosed, for example, in US20130096159, WO1990012008, U.S. Pat. No. 6,217,875, 4,605,669, 4,623,661, CA1327204, US20070111965, U.S. Pat. No. 4,897,422, US20060193797, U.S. Pat. No. 5,120,752, 5,112,848, 5,574,062, EPO416609, U.S. Pat. No. 4,822,811, EPO456760, U.S. Pat. No. 4,761,403, the content of each of which is incorporated by reference for its teachings of 12-LOX inhibitors.

In some embodiments, a 12-LOX inhibitor used for the methods disclosed herein can be a combination of 12-LOX inhibitors. In some of these embodiments, the mixing ratios of the 12-LOX inhibitors are optimized to provide maximum therapeutic effects.

At least some of the 12-LOX inhibitors (e.g., ML355) have been found to show low toxicity and good clearance from the body (Luci et al., *J Med Chem.* 2014, 57, 495-506), demonstrating the therapeutic values of the methods disclosed herein.

In some embodiments, the 12-LOX inhibitor contacts the platelet in vitro. For example, the platelets can be obtained from a subject and then cultured in a container (e.g., 96-well plate or petri dish). The in vitro contacting can be used for applications such as evaluation of the efficacy of the 12-LOX inhibitor.

In some embodiments, the 12-LOX inhibitor contacts the platelet in vivo. In these embodiments, the in vivo contacting can be in a subject taking heparin. The subject might be in need of treating or preventing an immune-mediated thrombocytopenia and thrombosis disorder.

Platelet activation can be assessed or measured by a variety of methods. For example, platelet activation can be quantified by factors such as change in shape and a tendency to aggregate. Shape change of platelets can be assessed by flow cytometry or electron microscopy. Platelet aggregation can be measured in a platelet aggregometer. Platelet activation can also be quantified by measuring the blood or urine levels of relevant platelet metabolic products or biomarkers (e.g., the alpha granule components, beta thromboglobulin and platelet factor 4, thromboxane $B_2$, or the soluble form of the adhesion molecule P-selectin). Some methods for measuring platelet activation are disclosed in U.S. Pat. No. 7,011,938, WO1996012956, and U.S. Pat. No. 6,391,568, the content of each of which is incorporated by reference in its entirety.

As 12-LOX inhibitors can inhibit or decrease immune-mediated platelet activation, another aspect of the invention relates to a method of treating or preventing an immune-mediated thrombocytopenia and thrombosis disorder, the method comprising administering to a subject in need thereof an effective amount of a 12-lipoxygenase inhibitor. Examples of immune-mediated thrombocytopenia and thrombosis disorders include, but are not limited to, heparin-induced thrombocytopenia (HIT); anti-phospholipid syndrome; sepsis syndrome; thrombosis associated with therapeutic or diagnostic monoclonal antibodies; and thrombotic thrombocytopenic purpura.

In some embodiments, an immune-mediated thrombocytopenia and thrombosis disorder can be triggered in the subject by the use of one or more heparin or derivatives thereof. In these embodiments, the immune-mediated thrombocytopenia and thrombosis disorder is heparin-induced thrombocytopenia (HIT).

HIT is a disorder resulting from the administration of heparin therapy, and is the development of a low platelet count (e.g., <100,000 platelets per milliliter in the blood). As used herein, the terms "HIT" and "heparin-induced thrombocytopenia and thrombosis (HITT)" are used interchangeably. Paradoxically, anticoagulant medication and thrombocytopenia manifest not as bleeding, but rather as and life-threatening thrombosis. The thrombotic events are multifocal, involving for example, veins, arteries and the microvasculature. In some HIT cases, thrombi form in macrovascular beds with overt clinical symptoms, such as DVT/PE, myocardial infarction, stroke, or limb ischemia. In other cases the thrombi are in the microvasculature, with effects that are overt clinically (e.g., adrenal thrombosis followed by hemorrhage, skin necrosis) or remain subclinical.

It was found that HIT occurred in 1% to 3% of patients who received unfractionated heparin, and in 0.1% of patients who received low-molecular-weight heparin. Currently there is no standard diagnostic method for HIT. Some diagnostic methods for HIT are disclosed, for example, in WO2001004159 and WO2013165969, the content of each of which is incorporated by reference in its entirety. Clinical scoring systems have also been developed to predict the probability of HIT onset in a variety of situations (Elalamy I, et al., Ann. Med. 2000, 32, 60-67. Samama M, et al., Bull Acad Natl Med. 1998, 182, 1517-1533). For example, in one clinical scoring system, scores are given to factors such as platelet count evolution, development of thrombosis, and other causes of thrombocytopenia.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect.

Dosage regimens of a 12-LOX inhibitor can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It can be advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of a 12-LOX inhibitor at levels lower than that required in order to achieve the desired therapeutic effect and gradually increase the dosage until the desired effect is achieved.

A physician or veterinarian having ordinary skill in the art can also readily determine when to initiate administering a pharmaceutical composition comprising a 12-LOX inhibitor. It should be noted that the timing for administration generally depends on diagnostic results. For example, the pharmaceutical composition comprising a 12-LOX inhibitor can be administered when one or more symptoms of HIT have occurred (e.g., a drop in platelet count).

The method disclosed herein can be used in combination with other methods or therapies for treating an immune-mediated thrombocytopenia and thrombosis disorder (e.g., HIT). For example, one therapeutic approach to treating HIT is the removal of heparin treatment and replacement with direct thrombin inhibitors (e.g., danaparoid, argatroban, or lepirudin). It should be noted that simple withdrawal of heparin does not end the immune-mediated thrombocytopenia and thrombosis disorder. In another example, a Factor Xa inhibitor (e.g., fondaparinux) can be used for HIT treatment. Other therapies include, but are not limited to, thrombolytic therapy (e.g., streptokinase or urokinase), thromboembolectomy, plasmapheresis, high-dose IV IgG, and GPIIb/IIIa inhibitors.

Yet another aspect of the invention relates to a method of treating or preventing a thrombotic event, myocardial infarction, or stroke, the method comprising administering to a subject in need thereof an effective amount of a 12-LOX inhibitor. Immune-mediated platelet activation can lead to thrombi formation, which can clot arteries and result in stroke, myocardial infarction, organ infarction, limb gangrene, or other serious complications.

In some aspects of all the embodiments, the subject is a mammal. In some aspects of all the embodiments, the subject is a human.

In some aspects of all the embodiments, the subject can be one who exhibits one or more risk factors for an immune-mediated thrombocytopenia and thrombosis disorder. In some aspects of all the embodiments, the subject is receiving heparin therapy. In some aspects of all the embodiments, the subject undergoes orthopedic surgery. It is known in the art that orthopedic surgery patients are at higher risk for developing HIT than are patients who receive heparin for other medical reasons.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology described herein is further illustrated by the following examples which in no way should be construed as being further limiting.

The description below provides the composition of matter and method of use around a 4-((2-hydroxy-3-methoxybenzyl)amino)benzenesulfonamide chemotype. The novel chemotypes for 12-LO inhibition disclosed herein are soluble, have favorable ADME properties, and good in vivo PK properties.

The synthesis of compound 1 involved a reductive amination with 4-aminobenzesulfonmide and 2-hydroxy-3-methoxybezaldehyde. A step-wise approach involving preformation of the imine was required with 4-amino-N-(thiazol-2-yl)benzenesulfonamide (2) and the requisite benzaldehyde overnight at 100° C. Subsequent reduction of the imine with sodium borohydride provided the desired compounds 1, 8-10 and 14-33 (Scheme 1, Method A). While this route worked for a majority of the analogs, some analogs (11-13 & 34) required an alternative route in which a Buchwald-Hartwig type coupling was utilized with the commercially available 4-bromo-N-(thiazol-2-yl)benzenesulfonamide (3) and 2-methoxy substituted benzyl amines to provide the desired products in a yields of 25-40% (Scheme 1, Method B). For modifications of the thiazole portion of the molecule we wanted to introduce diversity in the final step of the synthesis (Scheme 1, Method C). Therefore, reaction of commercially available 4-aminobenzenesulfonamide (4) with 2-hydroxy-3-methoxybenzaldehyde in ethanol at reflux for 18 h, followed by treatment with sodium borohydride provided compound 5 in 95% yield. The resulting sulfonamide derivative was then subjected to Cu-catalyzed N-arylation conditions using the appropriate heteroaryl bromides to afford compounds 35, 38, 44-48, 52, 53, 56-59, 61-69, 71, 74, and 75 in good yields. (Wang, X. et al. *Tetrahedron Lett.* 2012, 53, 7-10.) Despite the general versatility of this method, there was a few isolated cases where the Cu-catalyzed reaction failed to produce the desired product (e.g. compounds 77-83), or the heteroaryl bromides were not readily available. For these compounds a less direct route was developed by heating 4-nitrobenzene-1-sulfonyl chloride (6) and the required heteroaryl amines to 100° C. for 1.5 to 8 hours depending on the reactivity of the amine to give the 4-nitrophenyl-sulfonamide derivatives 7 (Scheme 1, Method D). Reduction of the nitro group was achieved using the H-Cube® Pro flow reactor with 10% Pd on carbon at 50° C. and a pressure of 50 bar. Alternatively, for less soluble compounds which were not amendable to flow chemistry, a Zn/AcOH reduction was performed at 60° C. in methanol. Once the desired aniline was in hand a reductive amination was carried out with the corresponding benzyl amine derivative to provide compounds 36, 37, 39-43, 49-51, 54, 55, 60, 70, 72, 73, and 76-83. The specific conditions for each step in Scheme 1 as shown in FIG. 1 are as follows: (i) RCHO (1.5 equiv), EtOH, 3-18 h, 100° C., NaBH$_4$ (3.0 equiv), 0.5-0.6 h; (ii) RCH$_2$NH$_2$ (1.2 equiv), Xantphos (0.06 equiv), Pd$_2$dba$_3$ (0.02 equiv), NaOtBu (2.5 equiv), 1,4-dioxane, MW, 30 min, 100° C. (iii) 2-hydroxy-3-methoxybenzaldehyde (1.2 equiv), EtOH, 6 h, 100° C., NaBH$_4$ (1.5 equiv), 30 min, 92%. (iv) R'Br (1.2 equiv), K$_2$CO$_3$ (2.5 equiv), 80° C., 6-8 h. (v) R'NH$_2$, pyridine, 100° C., 1.5-18 h. (vi) 10% Pd/C, MeOH/EtOAc, 50 bar, 50° C. or zinc (4.0 equiv), AcOH (4.0 equiv), methanol, 60° C., 30 min-2 h. (vii) 2-hydroxy-R-benzaldehyde (1.2 equiv), EtOH, 18 h, 100° C., NaBH$_4$ (3.0 equiv).

General Synthetic Procedures. (Scheme 1, Method A): 4-amino-N-(thiazol-2-yl)benzene sulfonamide (0.39 mmol) (2), and required benzaldehyde (0.67 mmol) were combined in ethanol (2 mL) in a sealed tube and heated to 100° C. for 4-18 h. The solid was allowed to cool to room temperature and sodium borohydride (0.80 mmol) was added and stirred for 30 min, during which time the reaction turned clear and then cloudy. The resulting solids were filtered, washed with ethanol, and purified using a prep-HPLC (gradient 10-100% acetonitrile w/0.1% TFA in water w/0.1% TFA) to give the desired product.

(Scheme 1, Method B) A solution of 4-bromo-N-(thiazol-2-yl)benzene sulfonamide (0.31 mmol) (3) in dioxane (1 mL) was added to a mixture of sodium tert-butoxide (0.78 mmol), 4,5-bis(diphenylphosphino)-9,9-dimethylxanthene (Xantphos) (0.02 mmol) and tris(dibenzylidellenetone)dipalladium(0) (Pd$_2$dba$_3$) (6.27 µmol) in dioxane (1 mL). The resulting mixture was degassed with argon for 15 min. then the requisite benzylamine (0.38 mmol) was added, the vessel was sealed and heated to 100° C. for 30 min in Biotage® microwave reactor. The reaction mixture was cooled to room temperature and filtered through celite. Silicycle® silica bound thiol was added and stirred overnight, again filtered through a pad of celite, concentrated, and purified by prep-HPLC (gradient 10-100% acetonitrile w/0.1% TFA in water w/0.1% TFA) to give the desired product.

(Scheme 1, Method C) 4-aminobenzenesulfonamide (4) (1.00 g, 5.81 mmol), 2-hydroxy-3-methoxybenzaldehyde (1.00 g, 7.00 mmol) in EtOH (29 mL) was heated to reflux for 4 h until reaction is an orange turbid mixture. The reaction mixture was cooled to room temperature before sodium borohydride (0.33 g, 8.71 mmol) was added and stirred for an additional 30 min. A white solid forms after 30 min and is collected by filtration and washed with copious amounts of ethanol, dried under vacuum and used as is in subsequent reactions. $^1$H NMR (400 MHz, DMSO-d$_6$) δ 7.60-7.27 (m, 2H), 6.75-6.40 (m, 4H), 6.06 (t, J=7.63 Hz, 1H), 4.18 (s, 2H), and 3.65 (s, 3H); $^{13}$C NMR (101 MHz, DMSO) δ 40.37, 55.32, 108.91, 109.42, 109.55, 111.29, 111.40, 121.05, 125.05, 127.49, 129.92, 150.17, 152.36, and 156.94; LC-MS retention time (Method 1): 2.876 min. General procedure: (Step iv) 4-(2-hydroxy-3-methoxybenzylamino)benzenesulfonamide (5) (0.58 mmol), arylbromide (0.70 mmol), K$_2$CO$_3$ (1.45 mmol), N,N'-dimethylethylenediamine (0.29 mmol), and copper(I)iodide (0.03 mmol) in 1,4-dioxane (1.5 mL) were place under N$_2$ and sealed in a 5 ml sealed tube. The reaction was heated to 70° C. for 6 to 8 h and monitored by LC/MS analysis. Upon completion the heterogeneous mixture was cooled to room temperature, filtered, and washed with dioxane. The solution was passed through a thiol cartridge (metal scavenging), diluted with AcOEt and washed with NH$_4$Cl (2×), water, and brine. The crude material was purified using a prep-HPLC (gradient 10-100% acetonitrile w/0.1% TFA in water w/0.1% TFA) to give the desired product.

(Scheme 1, Method D: Example) N-(benzo[d]thiazol-2-yl)-4-nitrobenzenesulfonamide (7): (Step V) To a stirred solution of benzo[d]thiazol-2-amine (0.50 g, 3.35 mmol) in pyridine (1.60 mL, 20.08 mmol) was added 4-nitrobenzene sulfonyl chloride (6) (0.82 g, 3.68 mmol) in three equal parts. The reaction mixture was heated for 75 min at 100° C., cooled to room temperature, after which time a yellow precipitate formed. The reaction mixture was allowed to sit at room temperature for 2 h then the yellow solid was collected by filtration, washed with ethanol, and dried under reduced pressure overnight to give 1.10 of the desired product. $^1$H NMR (400 MHz, DMSO-d$_6$) δ 8.90 (ddt, J=0.75, 1.63, and 5.59 Hz, 1H), 8.54, 8.41-8.28 (m, 1H), 8.13-7.96 (m, 2H), 7.82 (dq, J=0.80, and 7.96 Hz, 1H), 7.45-7.34 (m, 1H), 7.31-7.19 (m, 1H); LC-MS retention time (Method 1): 3.272 min; HRMS: m/z (M+H)$^+$=(Calculated for $C_{13}H_{10}N_3O_4S_2$, 336.0107). found 336.0107.

4-amino-N-(benzo[d]thiazol-2-yl)benzenesulfonamide (Step VI) N-(benzo[d]thiazol-2-yl)-4-nitrobenzenesulfonamide (0.20 g, 0.60 mmol), zinc (0.16 g, 2.39 mmol), acetic acid (0.14 mL, 2.39 mmol) was dissolved in MeOH (3 mL), and the mixture heated to 60° C. for 2 h. The heterogeneous mixture was filtered through a pad of celite washed with hot methanol, concentrated and purified using prep-HPLC (gradient 10-100% acetonitrile w/0.1% NH$_4$OH in water w/0.1% NH$_4$OH) to give the desired product. Alternate nitro reduction: N-(benzo[d]thiazol-2-yl)-4-nitrobenzenesulfonamide was dissolved in MeOH/EtOAc/THF (1:1:1) to give a 0.05 M solution passed through the H-Cube Pro® flow reactor using a 10% Pd/C, 70 mm CatCart® at 50 bar and 50° C. for two cycles at 0.9 mL/min. The solution was concentrated to give a pale yellow solid in a quantitative yield. $^1$H NMR (400 MHz, DMSO-d$_6$) δ 7.49-7.34 (m, 3H), 7.18 (ddd, J=0.56, 1.21, and 8.00 Hz, 1H), 7.03 (ddd, J=1.33, 7.24, and 7.97 Hz, 1H), 6.83 (ddd, J=1.20, 7.25, and 7.68 Hz, 1H), 6.51-6.38 (m, 2H), 5.42 (s, 2H); LC-MS retention time (Method 2): 3.933 min; HRMS: m/z (M+H)$^+$=(Calculated for $C_{13}H_{12}N_3O_2S_2$, 306.0365). found 306.0360.

N-(benzo[d]thiazol-2-yl)-4-((2-hydroxy-3-methoxybenzyl)amino)benzenesulfonamide (Step VII, representative example) (35, ML355): 4-amino-N-(benzo[d]thiazol-2-yl)benzenesulfonamide (0.10 g, 0.33 mmol), 2-hydroxy-3-methoxybenzaldehyde (0.075 g, 0.491 mmol) were heated in EtOH (1.5 mL) at 90° C. for 18 h. The reaction mixture was allowed to cool to room temperature before the addition of NaBH$_4$ (0.04 g, 0.98 mmol), and stirred for an additional 6 h. After this time, the reaction mixture was quenched with methanol and water then stirred for 20 min, the solids were filtered through celite, the filtrate collected, and concentrated under reduced pressure to provide a yellow solid. The crude material was purified using a prep-HPLC (gradient 10-100% acetonitrile w/0.1% TFA in water w/0.1% TFA) to give the desired product. $^1$H NMR (400 MHz, DMSO-d$_6$) δ 12.86 (s, 1H), 8.73 (d, J=0.5 Hz, 1H), 7.75 (ddd, J=0.6, 1.2, and 7.9 Hz, 1H), 7.54-7.46 (m, 2H), 7.40-7.31 (m, 1H), 7.28-7.16 (m, 2H), 6.93-6.79 (m, 2H), 6.78-6.55 (m, 4H), 4.23 (d, J=5.8 Hz, 2H) and 3.78 (s, 3H); $^{13}$C NMR (DMSO-d$_6$) δ ppm 152.4, 147.7, 144.3, 128.2, 125.7, 122.9, 120.4, 119.0, 111.4, 110.9, 56.2 and 40.6; LC-MS retention time (Method 1): 2.260 min; HRMS: m/z (M+H)$^+$=(Calculated for $C_{21}H_{19}N_3O_4S_2$, 441.0817). found 441.0819.

General Methods for Chemistry. All air or moisture sensitive reactions were performed under positive pressure of nitrogen with oven-dried glassware. Chemical reagents and anhydrous solvents were obtained from commercial sources and used as-is. Preparative purification was performed on a Waters semi-preparative HPLC. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis for purity was determined by two different methods denoted as Final QC Methods 1 and 2. Method 1: Analysis was performed on an Agilent 1290 Infinity Series HPLC. UHPLC Long Gradient Equivalent 4% to 100% acetonitrile (0.05% trifluoroacetic acid) in water over 3.5 minutes run time of 4 minutes with a flow rate of 0.8 mL/min. A Phenomenex Kinetex 1.7 micron C18 column (2.1×100 mm) was used at a temperature of 50° C. Method 2: analysis was performed on an Agilent 1260 with a 7 minute gradient of 4% to 100% acetonitrile (containing 0.025% trifluoroacetic acid) in water (containing 0.05% trifluoroacetic acid) over 8 minute run time at a flow rate of 1 mL/min. A Phenomenex Luna C18 column (3 micron, 3×75 mm) was used at a temperature of 50° C. Purity determination was performed using an Agilent Diode Array Detector for both Method 1 and Method 2. Mass determination was performed using an Agilent 6130 mass spectrometer with electrospray ionization in the positive mode. All of the analogs for assay have purity greater than 95% based on both analytical methods. $^1$H and $^{13}$C NMR spectra were recorded on a Varian 400 (100) MHz spectrometer. High resolution mass spectrometry was recorded on Agilent 6210 Time-of-Flight LC/MS system.

Description of Embodiments of the Present Invention

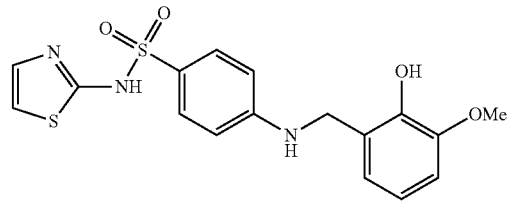 [SMILES: COc1cccc(CNc2ccc(S(=O)(=O)Nc3nccs3)cc2)c1O]

4-(2-hydroxy-3-methoxybenzylamino)-N-(thiazol-2-yl)benzenesulfonamide (1)

Method A: using 2-hydroxy-3-methoxybenzaldehyde; $^1$H NMR (400 MHz, DMSO-d$_6$) δ 8.67 (s, 1H), 7.44-7.33 (m, 2H), 7.00 (d, J=4.20 Hz, 1H), 6.85-6.62 (m, 3H), 6.60-6.45 (m, 4H), 4.19 (d, J=5.91 Hz, 2H), and 3.77 (s, 3H); LC-MS retention time (Method 2): 4.394 min; HRMS: m/z (M+H)$^+$=(Calculated for $C_{17}H_{18}N_3O_4S_2$ 392.0733). found, 392.0726.

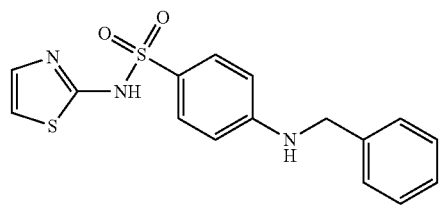 [SMILES: O=S(=O)(Nc1nccs1)c1ccc(NCc2ccccc2)cc1]

4-(benzylamino)-N-(thiazol-2-yl)benzene sulfonamide TFA (8)

Method A: using benzaldehyde; $^1$H NMR (400 MHz, DMSO-d$_6$) δ 12.39 (s, 1H), 7.48-7.39 (m, 2H), 7.35-7.13 (m, 6H), 6.99 (t, J=6.00 Hz, 1H), 6.71 (d, J=4.60 Hz, 1H), 6.62-6.54 (m, 2H), and 4.29 (d, J=5.61 Hz, 2H); LC-MS retention time (Method 2): 4.780 min; HRMS: m/z (M+H)$^+$=(Calculated for $C_{16}H_{16}N_3O_2S_2$ 346.0678). found, 346.0672.

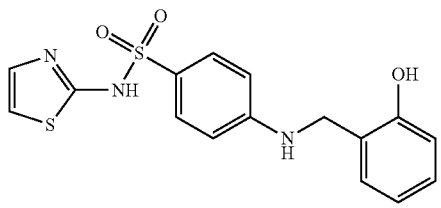 [SMILES: O=S(=O)(Nc1nccs1)c1ccc(NCc2ccccc2O)cc1]

4-(2-hydroxybenzylamino)-N-(thiazol-2-yl)benzene sulfonamide (9)

Method A: using 2-hydroxybenzyaldehyde; $^1$H NMR (400 MHz, DMSO-d$_6$) δ 9.49 (s, 1H), 7.44-7.35 (m, 2H), 7.13 (dd, J=1.65, and 7.55 Hz, 1H), 7.03 (ddd, J=1.75, 7.32, and 8.01 Hz, 1H), 6.92-6.67 (m, 4H), 6.52-6.41 (m, 2H), 6.38-6.29 (m, 2H), and 4.17 (d, J=5.68 Hz, 2H); LC-MS retention time (Method 2): 4.213 min; HRMS: m/z (M+H)$^+$=(Calculated for C$_{16}$H$_{16}$N$_3$O$_3$S$_2$362.0628). found, 362.0620.

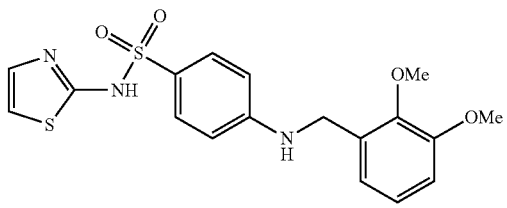

4-(2,3-dimethoxybenzylamino)-N-(thiazol-2-yl)benzene sulfonamide (12)

Method B: using 2,3-dimethoxyphenyl)methanamine; $^1$H NMR (400 MHz, DMSO-d$_6$) δ 7.46 (d, J=8.78 Hz, 2H), 7.18 (d, J=4.63 Hz, 1H), 7.06-6.90 (m, 2H), 6.87-6.79 (m, 2H), 6.73 (d, J=4.58 Hz, 1H), 6.59 (d, J=8.84 Hz, 2H), 4.28 (d, J=5.90 Hz, 2H), and 3.78 (d, J=13.99 Hz, 6H); LC-MS retention time (Method 2): 4.756 min; HRMS: m/z (M+H)$^+$=(Calculated for C$_{18}$H$_{20}$N$_3$O$_4$S$_2$ 406.0890). found, 406.0885.

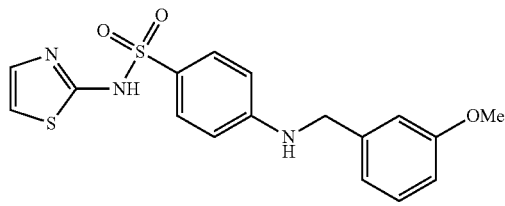 [SMILES: COc1cccc(CNc2ccc(S(=O)(=O)Nc3nccs3)cc2)c1]

4-(3-methoxybenzylamino)-N-(thiazol-2-yl)benzene sulfonamide (10)

Method B: using (3-dimethoxyphenyl)methanamine; $^1$H NMR (400 MHz, DMSO-d$_6$) δ 7.48-7.41 (m, 2H), 7.27-7.19 (m, 1H), 7.18 (d, J=4.63 Hz, 1H), 6.99 (t, J=6.06 Hz, 1H), 6.93-6.85 (m, 2H), 6.79 (dd, J=1.10, and 2.48 Hz, 1H), 6.73 (d, J=4.60 Hz, 1H), 6.63-6.55 (m, 2H), 4.27 (d, J=5.92 Hz, 2H), and 3.72 (s, 3H); LC-MS retention time (Method 2): 4.777 min; HRMS: m/z (M+Na)$^+$=(Calculated for C$_{17}$H$_{17}$N$_3$NaO$_3$S$_2$, 398.0604). found, 398.0584.

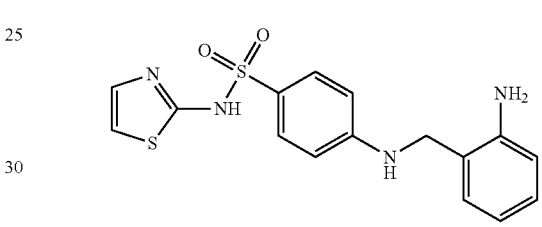

4-(2-aminobenzylamino)-N-(thiazol-2-yl)benzene sulfonamide (13)

Method A: using tert-butyl (2-formylphenyl)carbamate and removing the subsequent carbamate with 4 M HCl in dioxane over 30 min. $^1$H NMR (400 MHz, DMSO-d$_6$) δ 7.54-7.37 (m, 3H), 7.24-7.06 (m, 3H), 6.96 (d, J=7.86 Hz, 1H), 6.86 (h, J=7.06 Hz, 1H), 6.74 (d, J=4.61 Hz, 1H), 6.65-6.50 (m, 3H), and 4.23 (s, 2H); LC-MS retention time (Method 1): 1.863 min; HRMS: m/z (M+H)$^+$=(Calculated for C$_{16}$H$_{17}$N$_4$O$_2$S$_2$361.0787). found, 361.0784.

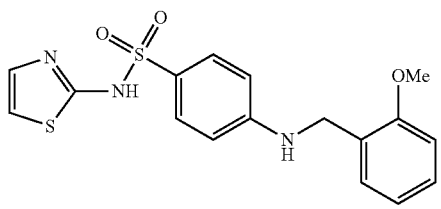

4-(2-methoxybenzylamino)-N-(thiazol-2-yl)benzene sulfonamide TFA (11)

Method B: using 2-dimethoxyphenyl)methanamine; $^1$H NMR (400 MHz, DMSO-d$_6$) δ 12.39 (s, 1H), 7.48-7.39 (m, 2H), 7.26-7.12 (m, 3H), 6.98 (dd, J=1.03, and 8.26 Hz, 1H), 6.90-6.76 (m, 2H), 6.71 (d, J=4.63 Hz, 1H), 6.59-6.50 (m, 2H), 4.23 (d, J=5.89 Hz, 2H), and 3.81 (s, 3H); LC-MS retention time (Method 2): 4.888 min; HRMS: m/z (M+H)$^+$=(Calculated for C$_{17}$H$_{18}$N$_3$O$_3$S$_2$, 376.0784) found, 376.0765.

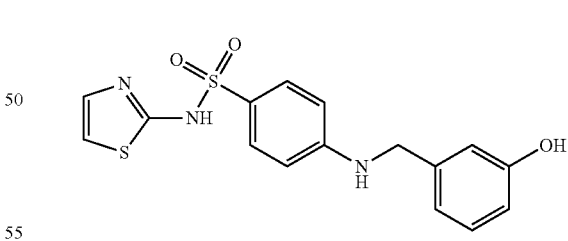

4-(3-hydroxybenzylamino)-N-(thiazol-2-yl)benzene sulfonamide (14)

Method A: using 3-hydroxybenzaldehyde; $^1$H NMR (400 MHz, DMSO-d$_6$) δ 9.31 (s, 1H), 7.51-7.37 (m, 2H), 7.18 (d, J=4.62 Hz, 1H), 7.10 (t, J=7.77 Hz, 1H), 6.97 (t, J=5.90 Hz, 1H), 6.79-6.68 (m, 3H), 6.66-6.49 (m, 3H), and 4.31-4.14 (m, 2H); LC-MS retention time (Method 1): 1.775 min; HRMS: m/z (M+H)$^+$=(Calculated for C$_{16}$H$_{16}$N$_3$O$_3$S$_2$362.0628). found, 362.0614.

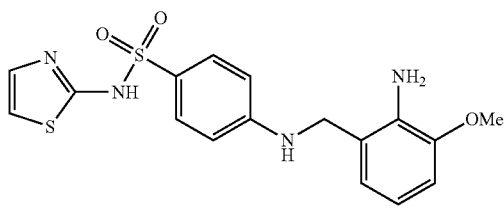 [SMILES: COc1cccc(CNc2ccc(S(=O)(=O)Nc3nccs3)cc2)c1N]

4-(2-amino-3-methoxybenzylamino)-N-(thiazol-2-yl)benzenesulfonamide TFA (15)

Method A: using 3-methoxy-2-nitrobenzaldehyde; A heterogeneous solution of 4-(3-methoxy-2-nitrobenzylamino)-N-(thiazol-2-yl)benzenesulfonamide (0.075 g, 0.178 mmol) in MeOH (1.8 mL), AcOH (0.102 mL, 1.784 mmol) and zinc (0.023 g, 0.357 mmol) were stirred for 30 min, filtered through celite, and washed with MeOH. The filtrate was concentrated and purified using a prep-HPLC (gradient 10-100% acetonitrile w/0.1% TFA in water w/0.1% TFA) to give the desired product; $^1$H NMR (400 MHz, DMSO-d$_6$) δ 7.44 (d, J=8.78 Hz, 2H), 7.17 (d, J=4.61 Hz, 1H), 6.78 (dd, J=1.23, and 7.81 Hz, 1H), 6.75-6.67 (m, 3H), 6.56 (d, J=8.82 Hz, 2H), 4.16 (s, 2H), and 3.77 (s, 3H); LC-MS retention time (Method 1): 2.775 min; HRMS: m/z (M+H)$^+$=(Calculated for C$_{17}$H$_{19}$N$_4$O$_3$S$_2$391.0893). found, 391.0874.

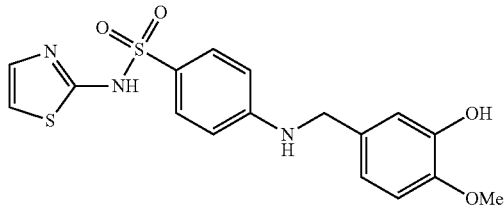 [SMILES: COc1ccc(CNc2ccc(S(=O)(=O)Nc3nccs3)cc2)cc1O]

4-(3-hydroxy-4-methoxybenzylamino)-N-(thiazol-2-yl)benzenesulfonamide (16)

Method A: using 3-hydroxy-4-methoxybenzaldehyde; $^1$H NMR (400 MHz, DMSO-d$_6$) δ 8.86 (s, 1H), 7.52-7.32 (m, 2H), 7.15 (d, J=4.61 Hz, 1H), 6.95-6.74 (m, 2H), 6.77-6.62 (m, 4H), 6.62-6.49 (m, 2H), 4.13 (d, J=5.92 Hz, 2H), and 3.70 (s, 3H); LC-MS retention time (Method 2): 4.123 min; HRMS: m/z (M+H)$^+$=(Calculated for C$_{17}$H$_{18}$N$_3$O$_4$S$_2$, 392.0733). found, 392.0719.

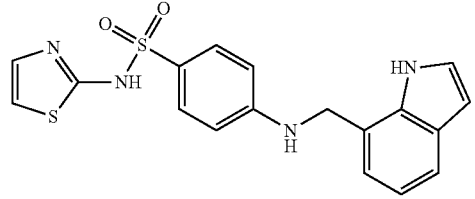 [SMILES: O=S(=O)(Nc1nccs1)c1ccc(NCc2cccc3cc[nH]c23)cc1]

4-((1H-indol-7-yl)methylamino)-N-(thiazol-2-yl)benzenesulfonamide (17)

Method A: using 1H-indole-7-carbaldehyde; $^1$H NMR (400 MHz, DMSO-d$_6$) δ 7.51-7.38 (m, 4H), 7.36-7.31 (m, 1H), 7.16 (t, J=4.53 Hz, 1H), 6.95-6.85 (m, 2H), 6.70 (d, J=4.62 Hz, 1H), 6.67-6.57 (m, 2H), 6.44 (dd, J=1.83, and 3.08 Hz, 1H), and 4.53 (d, J=5.67 Hz, 2H); LC-MS retention time (Method 2): 4.899 min; HRMS: m/z (M+H)$^+$=(Calculated for C$_{18}$H$_{17}$N$_4$O$_2$S$_2$385.0787). found, 385.0774.

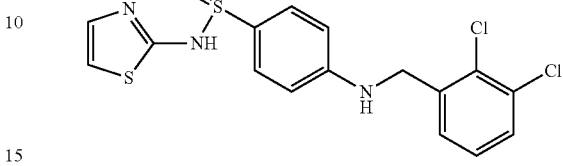

4-(2,3-dichlorobenzylamino)-N-(thiazol-2-yl)benzenesulfonamide (18)

Method A: using 2,3-dichlorobenzaldehyde; LC-MS retention time (Method 2): 5.786 min; HRMS: m/z (M+H)$^+$=(Calculated for C$_{16}$H$_{14}$Cl$_2$N$_3$O$_2$S$_2$413.9899). found, 413.9907.

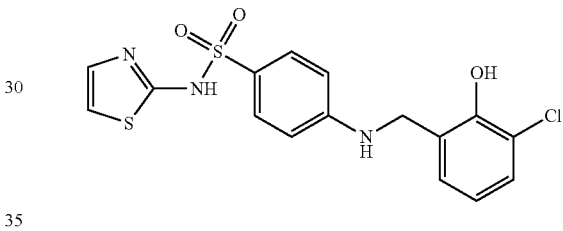

4-(3-chloro-2-hydroxybenzylamino)-N-(thiazol-2-yl)benzenesulfonamide (19)

Method A: using 3-chloro-2-hydroxybenzaldehyde; $^1$H NMR (400 MHz, DMSO-d$_6$) δ 7.48-7.35 (m, 2H), 7.21 (dd, J=1.63, and 7.94 Hz, 1H), 7.13-7.02 (m, 1H), 6.87 (d, J=3.82 Hz, 1H), 6.76 (t, J=7.77 Hz, 1H), 6.51-6.43 (m, 2H), 6.35 (d, J=3.82 Hz, 1H), and 4.25 (s, 2H); LC-MS retention time (Method 1): 2.076 min; HRMS: m/z (M+Na)$^+$=(Calculated for C$_{16}$H$_{14}$ClN$_3$NaO$_3$S$_2$419.0085) found, 419.0047.

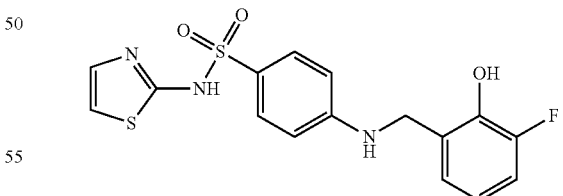

4-(3-fluoro-2-hydroxybenzylamino)-N-(thiazol-2-yl)benzenesulfonamide (20)

Method A: using 3-fluoro-2-hydroxybenzaldehyde; $^1$H NMR (400 MHz, DMSO-d$_6$) δ 9.63 (s, 1H), 7.49-7.33 (m, 2H), 7.08-6.93 (m, 2H), 6.91-6.80 (m, 1H), 6.72 (t, J=7.94 Hz, 1H), 6.51-6.38 (m, 3H), 6.34 (d, J=3.80 Hz, 1H), and 4.23 (d, J=3.52 Hz, 2H); LC-MS retention time (Method 1):

2.076 min; HRMS: m/z (M+H)$^+$=(Calculated for C$_{16}$H$_{15}$FN$_3$O$_3$S$_2$, 380.0533). found, 380.0521.

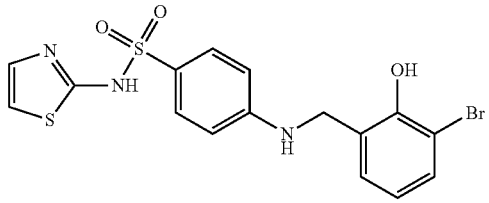 [SMILES: O=S(=O)(Nc1nccs1)c1ccc(NCc2cccc(Br)c2O)cc1]

4-(3-bromo-2-hydroxybenzylamino)-N-(thiazol-2-yl) benzenesulfonamide, (21)

Method A: using 3-bromo-2-hydroxybenzaldehyde; $^1$H NMR (400 MHz, DMSO-d$_6$) δ 9.64 (s, 1H), 8.16-8.02 (m, 1H), 7.86 (d, J=8.75 Hz, 2H), 7.79 (dd, J=1.59, and 7.90 Hz, 1H), 7.58 (d, J=4.61 Hz, 1H), 7.52 (dd, J=1.56, and 7.59 Hz, 1H), 7.28 (s, 1H), 7.14 (t, J=7.78 Hz, 1H), 6.96 (d, J=8.89 Hz, 2H), and 4.69 (d, J=5.79 Hz, 2H); LC-MS retention time (Method 2): 4.777 min; HRMS: m/z (M+H)$^+$=(Calculated for C$_{16}$H$_{15}$BrN$_3$O$_3$S$_2$441.9712). found, 441.9705.

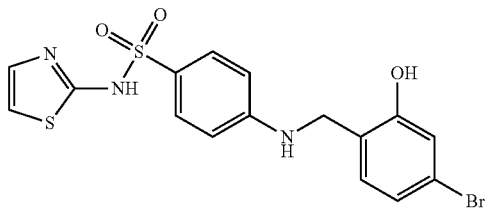 [SMILES: O=S(=O)(Nc1nccs1)c1ccc(NCc2ccc(Br)cc2O)cc1]

4-(4-bromo-2-hydroxybenzylamino)-N-(thiazol-2-yl) benzenesulfonamide (22)

Method A: using 4-bromo-2-hydroxybenzaldehyde; $^1$H NMR (400 MHz, DMSO-d$_6$) δ 10.06 (s, 1H), 7.47-7.34 (m, 2H), 7.03 (d, J=8.13 Hz, 1H), 6.99-6.92 (m, 2H), 6.88 (dd, J=1.97, and 8.10 Hz, 1H), 6.65-6.31 (m, 4H), and 4.12 (d, J=5.91 Hz, 2H); LC-MS retention time (Method 1): 2.938 min; HRMS: m/z (M+H)$^+$=(Calculated for C$_{16}$H$_{15}$BrN$_3$O$_3$S$_2$, 441.9712). found, 441.9704.

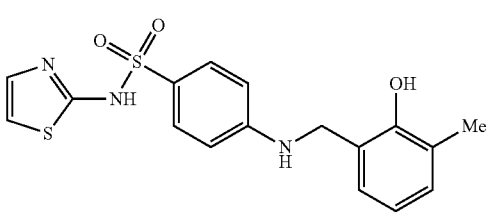 [SMILES: Cc1cccc(CNc2ccc(S(=O)(=O)Nc3nccs3)cc2)c1O]

4-(2-hydroxy-3-methylbenzylamino)-N-(thiazol-2-yl)benzenesulfonamide (23)

Method A: using 2-hydroxy-3-methylbenzaldehyde; $^1$H NMR (400 MHz, DMSO-d$_6$) δ 8.25 (s, 1H), 7.34-7.21 (m, 2H), 7.00 (d, J=4.62 Hz, 1H), 6.84-6.75 (m, 2H), 6.64-6.48 (m, 3H), 6.44-6.31 (m, 2H), 4.08 (d, J=5.76 Hz, 2H), and 2.01 (s, 3H); LC-MS retention time (Method 1): 2.083 min; HRMS: m/z (M+H)$^+$=(Calculated for C$_{17}$H$_{18}$N$_3$O$_3$S$_2$, 376.0784). found, 376.0779.

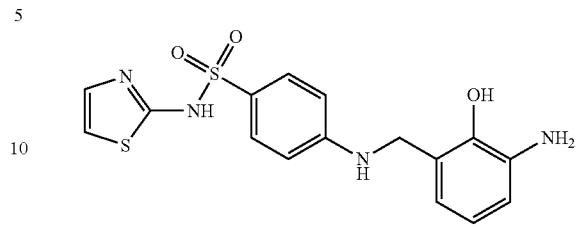

4-(3-amino-2-hydroxybenzylamino)-N-(thiazol-2-yl) benzenesulfonamide (24)

Method A: using 2-hydroxy-3-nitrobenzaldehyde and reducing the nitro-group with zinc and acetic acid conditions (see compound 15 for details). $^1$H NMR (400 MHz, DMSO-d$_6$) δ 7.49-7.39 (m, 2H), 7.17 (d, J=4.65 Hz, 1H), 6.92 (t, J=8.63 Hz, 2H), 6.85-6.69 (m, 3H), 6.60-6.50 (m, 2H), and 4.28 (s, 2H); LC-MS retention time (Method 1): 2.263 min; HRMS: m/z (M+H)$^+$=(Calculated for C$_{16}$H$_{17}$N$_4$O$_3$S$_2$, 377.0737). found, 377.0730.

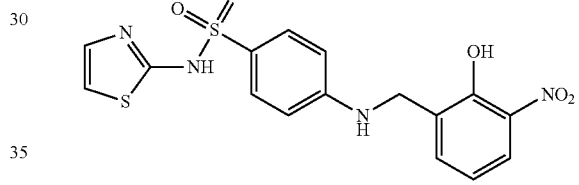

4-(2-hydroxy-3-nitrobenzylamino)-N-(thiazol-2-yl) benzenesulfonamide (25)

Method 1A: using 2-hydroxy-3-nitrobenzaldehyde; $^1$H NMR (400 MHz, DMSO-d$_6$) δ 7.88 (dd, J=1.65, and 8.43 Hz, 1H), 7.58-7.24 (m, 3H), 7.17 (d, J=4.66 Hz, 1H), 7.05-6.88 (m, 2H), 6.72 (d, J=4.61 Hz, 1H), 6.67-6.34 (m, 2H), and 4.33 (d, J=4.46 Hz, 2H); LC-MS retention time (Method 2): 4.742 min; HRMS: m/z (M+H)$^+$=(Calculated for C$_{16}$H$_{15}$N$_4$O$_5$S$_2$407.0478). found, 407.0465.

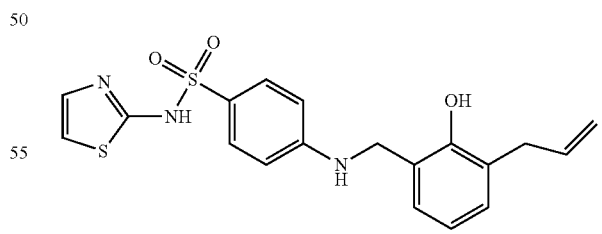

4-(3-allyl-2-hydroxybenzylamino)-N-(thiazol-2-yl) benzenesulfonamide TFA (26)

Method A: using 3-allyl-2-hydroxybenzaldehyde; $^1$H NMR (400 MHz, DMSO-d$_6$) δ 12.41 (s, 1H), 8.47 (s, 1H), 7.49-7.38 (m, 2H), 7.17 (d, J=4.61 Hz, 1H), 6.96 (ddd, J=1.73, 7.52, and 22.52 Hz, 2H), 6.80-6.65 (m, 3H), 6.61-

6.50 (m, 2H), 5.93 (ddt, J=6.63, 10.04, and 16.79 Hz, 1H), 5.08-4.95 (m, 2H), 4.25 (s, 2H), and 3.34 (dt, J=1.44, and 6.58 Hz, 2H); LC-MS retention time (Method 1): 3.155 min; HRMS: m/z (M+H)$^+$=(Calculated for $C_{19}H_{20}N_3O_3S_2$ 402.0941). found, 402.0926.

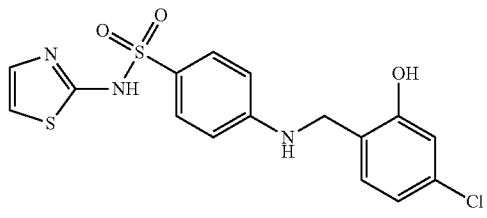 [SMILES: O=S(=O)(Nc1nccs1)c1ccc(NCc2ccc(Cl)cc2O)cc1]

4-(4-chloro-2-hydroxybenzylamino)-N-(thiazol-2-yl)benzenesulfonamide (27)

Method A: using 4-chloro-2-hydroxybenzaldehyde; $^1$H NMR (400 MHz, DMSO-d$_6$) δ 7.38 (d, J=8.6 Hz, 2H), 7.07 (d, J=8.2 Hz, 1H), 6.92-6.61 (m, 3H), 6.49-6.20 (m, 4H), and 4.12 (s, 2H); LC-MS retention time (Method 2): 4.700 min; HRMS: m/z (M+H)$^+$=(Calculated for $C_{16}H_{15}ClN_3O_3S_2$ 396.0238). found, 396.0220.

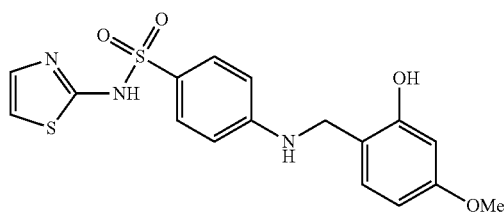 [SMILES: COc1ccc(CNc2ccc(S(=O)(=O)Nc3nccs3)cc2)c(O)c1]

4-(2-hydroxy-4-methoxybenzylamino)-N-(thiazol-2-yl)benzenesulfonamide (28)

Method A: using 2-hydroxy-4-methoxybenzaldehyde; $^1$H NMR (400 MHz, DMSO-d$_6$) δ 9.51 (s, 1H), 7.41-7.32 (m, 2H), 7.00 (d, J=8.37 Hz, 1H), 6.87-6.80 (m, 1H), 6.49-6.39 (m, 2H), 6.36 (d, J=2.47 Hz, 1H), 6.34-6.26 (m, 2H), 6.21 (t, J=5.86 Hz, 1H), 4.07 (d, J=5.77 Hz, 2H), and 3.63 (s, 3H); LC-MS retention time (Method 1): 3.155 min; HRMS: m/z (M+H)$^+$=(Calculated for $C_{17}H_{18}N_3O_4S_2$ 392.0733). found, 392.0715.

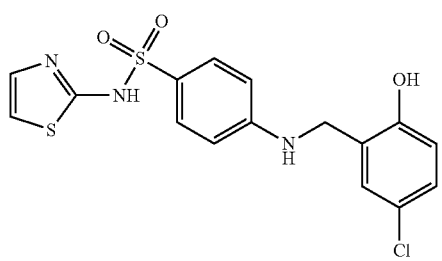 [SMILES: O=S(=O)(Nc1nccs1)c1ccc(NCc2cc(Cl)ccc2O)cc1]

4-(5-chloro-2-hydroxybenzylamino)-N-(thiazol-2-yl)benzenesulfonamide (29)

Method A: using 5-chloro-2-hydroxybenzaldehyde; $^1$H NMR (400 MHz, DMSO-d$_6$) δ 10.00 (s, 1H), 7.48-7.37 (m, 2H), 7.13-7.00 (m, 3H), 6.89-6.76 (m, 2H), 6.64 (d, J=4.44 Hz, 1H), 6.58-6.48 (m, 2H), and 4.17 (d, J=5.97 Hz, 2H); LC-MS retention time (Method 2): 4.610 min; HRMS: m/z (M+H)$^+$=(Calculated for $C_{16}H_{15}ClN_3O_3S_2$ 396.0238). found, 396.0233.

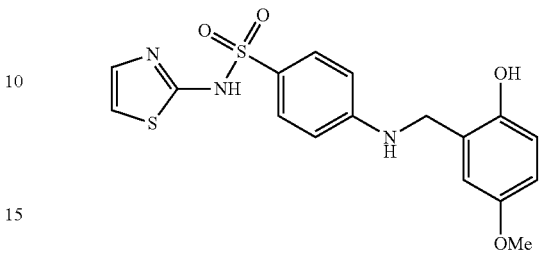

4-(2-hydroxy-5-methoxybenzylamino)-N-(thiazol-2-yl)benzenesulfonamide (30)

Method A: using 2-hydroxy-5-methoxybenzaldehyde; $^1$H NMR (400 MHz, DMSO-d$_6$) δ 9.12 (s, 1H), 7.47-7.38 (m, 2H), 7.08 (d, J=4.44 Hz, 1H), 6.77-6.65 (m, 3H), 6.65-6.48 (m, 4H), 4.15 (d, J=5.91 Hz, 2H), and 3.56 (s, 3H); LC-MS retention time (Method 2): 4.137 min; HRMS: m/z (M+H)$^+$=(Calculated for $C_{17}H_{18}N_3O_4S_2$ 392.0733). found, 392.0725.

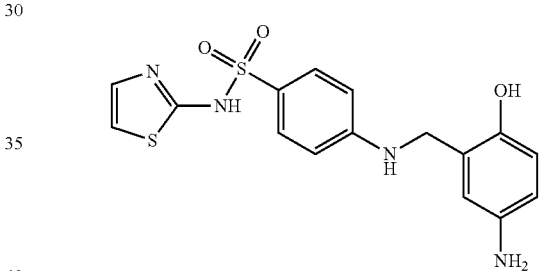

4-(5-amino-2-hydroxybenzylamino)-N-(thiazol-2-yl)benzenesulfonamide (31)

Method A: using 2-hydroxy-5-nitrobenzylaldehyde and reducing the nitro-group with zinc and acetic acid conditions (see compound 15 for details). $^1$H NMR (400 MHz, DMSO-d$_6$) δ 9.92 (s, 1H), 7.46 (d, J=8.83 Hz, 2H), 7.18 (d, J=4.64 Hz, 1H), 7.04-6.92 (m, 2H), 6.86 (d, J=8.23 Hz, 1H), 6.73 (d, J=4.66 Hz, 1H), 6.53 (d, J=8.83 Hz, 2H), and 4.22 (d, J=5.77 Hz, 2H); LC-MS retention time (Method 1): 2.165 min; HRMS: m/z (M+H)$^+$=(Calculated for $C_{16}H_{17}N_4O_3S_2$ 377.0737). found, 377.0719.

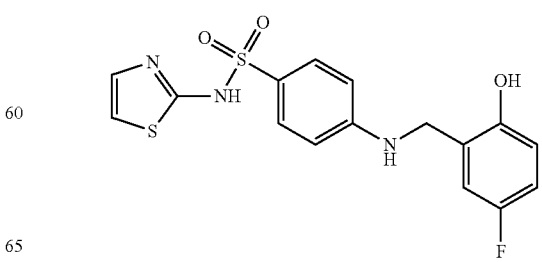

4-(5-fluoro-2-hydroxybenzylamino)-N-(thiazol-2-yl)benzenesulfonamide (32)

Method A: using 5-fluoro-2-hydroxybenzaldehyde; $^1$H NMR (400 MHz, DMSO-d$_6$) δ 9.63-9.54 (m, 1H), 7.44-7.33 (m, 2H), 6.92-6.73 (m, 4H), 6.51-6.36 (m, 3H), 6.36-6.29 (m, 1H), and 4.14 (d, J=6.00 Hz, 2H); LC-MS retention time (Method 1): 3.017 min; HRMS: m/z (M+H)$^+$=(Calculated for C$_{16}$H$_{15}$FN$_3$O$_3$S$_2$, 380.0533). found, 380.0526.

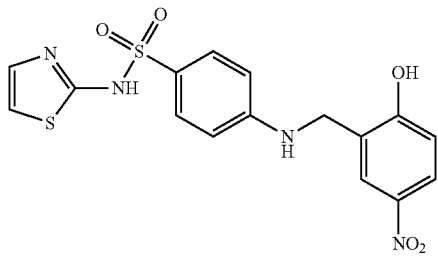 [SMILES: O=[N+]([O-])c1ccc(O)c(CNc2ccc(S(=O)(=O)Nc3nccs3)cc2)c1]

4-(2-hydroxy-5-nitrobenzylamino)-N-(thiazol-2-yl)benzenesulfonamide (33)

Method A: using 2-hydroxy-5-nitrobenzylaldehyde; $^1$H NMR (400 MHz, DMSO-d$_6$) δ ppm 7.92-7.76 (m, 2H), 7.41 (d, J=9.0 Hz, 2H), 6.97 (d, J=4.3 Hz, 1H), 6.56-6.40 (m, 4H), 5.74 (s, 1H), and 4.10 (s, 2H); LC-MS retention time (Method 2): 4.273 min; HRMS: m/z (M+H)$^+$=(Calculated for C$_{16}$H$_{15}$N$_4$O$_5$S$_2$, 407.0478). found, 407.0470.

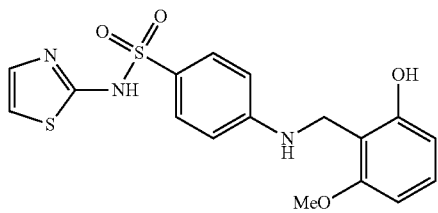 [SMILES: COc1cccc(O)c1CNc1ccc(S(=O)(=O)Nc2nccs2)cc1]

4-(2-hydroxy-6-methoxybenzylamino)-N-(thiazol-2-yl)benzenesulfonamide (34)

Method B: using 2-hydroxy-6-methoxybenzaldehyde; $^1$H NMR (400 MHz, DMSO-d$_6$) δ 9.59 (s, 1H), 7.74-7.54 (m, 1H), 7.42 (d, J=8.79 Hz, 2H), 7.24-7.05 (m, 1H), 6.68 (d, J=8.87 Hz, 2H), 6.46 (ddd, J=0.93, 7.08, and 8.22 Hz, 2H), 6.22 (d, J=5.51 Hz, 1H), 4.12 (d, J=5.21 Hz, 2H), and 3.74 (s, 3H); LC-MS retention time (Method 1): 2.960 min; HRMS: m/z (M+H)$^+$=(Calculated for C$_{17}$H$_{18}$N$_3$O$_4$S$_2$, 392.0733). found, 392.0716.

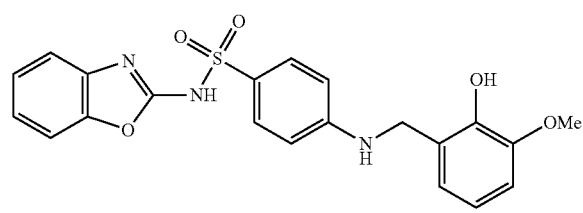 [SMILES: COc1cccc(CNc2ccc(S(=O)(=O)Nc3nc4ccccc4o3)cc2)c1O]

N-(benzo[d]oxazol-2-yl)-4-((2-hydroxy-3-methoxybenzyl)amino)benzenesulfonamide (36)

Method C: using 2-bromobenzoxazole; $^1$H NMR (600 MHz, DMSO-d$_6$) δ 12.40 (s, 1H), 8.71 (s, 1H), 7.55 (dd, J=2.60, and 9.29 Hz, 2H), 7.43 (d, J=7.93 Hz, 1H), 7.31-7.25 (m, 1H), 7.26-7.20 (m, 1H), 7.16 (td, J=1.42, and 7.82 Hz, 1H), 6.86 (t, J=5.64 Hz, 1H), 6.81 (dd, J=1.72, and 7.88 Hz, 1H), 6.75-6.69 (m, 1H), 6.66 (t, J=7.85 Hz, 1H), 6.61-6.54 (m, 2H), 4.21 (d, J=5.58 Hz, 2H), and 3.76 (d, J=2.79 Hz, 3H); $^{13}$C NMR (151 MHz, DMSO-d$_6$) δ 156.01, 152.37, 147.74, 144.28, 128.27, 125.73, 125.45, 123.67, 120.40, 119.06, 112.19, 111.31, 110.88, 110.59, 56.23, and 41.15; LC-MS retention time (Method 2): 4.848 min; HRMS: m/z (M+H)$^+$=(Calculated for C$_{21}$H$_{20}$N$_3$O$_5$S, 426.1118). found, 426.1098.

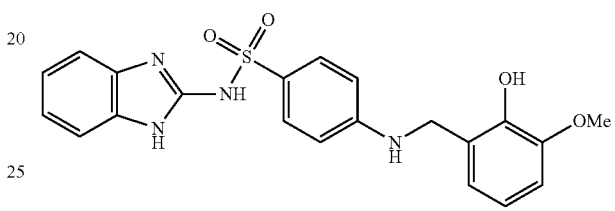

N-(1H-benzo[d]imidazol-2-yl)-4-((2-hydroxy-3-methoxybenzyl)amino)benzenesulfonamide (37)

Method D: using 2-aminobenzimidazole and 2-hydroxy-3-methoxybenzaldehyde; $^1$H NMR (600 MHz, DMSO-d$_6$) δ 11.68 (s, 2H), 7.56-7.49 (m, 2H), 7.22 (dt, J=3.37, and 5.83 Hz, 2H), 7.06 (dt, J=3.34, and 5.73 Hz, 2H), 6.79 (dd, J=1.71, and 7.99 Hz, 1H), 6.71 (dd, J=1.59, and 7.73 Hz, 1H), 6.65 (t, J=7.83 Hz, 1H), 6.58-6.50 (m, 2H), 4.19 (s, 2H), and 3.75 (s, 3H). $^{13}$C NMR (151 MHz, DMSO-d$_6$) δ 151.47, 150.22, 147.72, 144.26, 130.61, 129.89, 127.61, 125.79, 122.59, 120.44, 119.05, 111.46, 111.09, 110.86, 56.23, and 41.32; LC-MS retention time (Method 2): 4.454 min; HRMS: m/z (M+H)$^+$ (Calculated for C$_{21}$H$_{20}$N$_4$O$_4$S, 424.1205). found 424.1202.

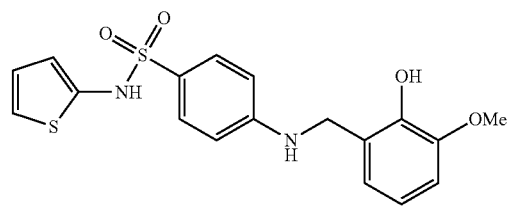 [SMILES: COc1cccc(CNc2ccc(S(=O)(=O)Nc3cccs3)cc2)c1O]

4-(2-hydroxy-3-methoxybenzylamino)-N-(thiophen-2-yl)benzenesulfonamide (38)

Method C: using 2-bromothiophene; $^1$H NMR (400 MHz, DMSO-d$_6$) δ 8.73 (s, 1H), 7.38-7.28 (m, 1H), 7.05-6.98 (m, 1H), 6.91 (t, J=6.1 Hz, 1H), 6.83 (dd, J=2.0, and 7.8 Hz, 1H), 6.78-6.64 (m, 3H), 6.61-6.52 (m, 2H), 6.51-6.43 (m, 1H), 4.25 (s, 2H), and 3.80 (s, 3H); LC-MS retention time (Method 1): 2.435 min; HRMS: m/z (M+H)$^+$ (Calculated for C$_{18}$H$_{19}$N$_2$O$_4$S$_2$, 391.0781). found 391.0773.

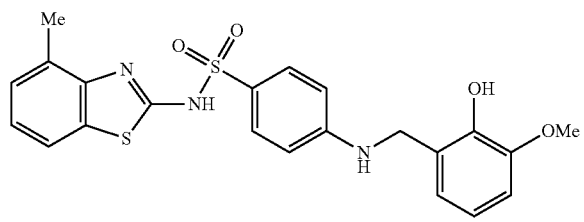 [SMILES: COc1cccc(CNc2ccc(S(=O)(=O)Nc3nc4c(C)cccc4s3)cc2)c1O]

4-((2-hydroxy-3-methoxybenzyl)amino)-N-(4-methylbenzo[d]thiazol-2-yl)benzenesulfonamide TFA (39)

Method D: using 2-amino-4-methylbenzthiazole and 2-hydroxy-3-methoxybenzaldehyde; $^1$H NMR (400 MHz, DMSO-$d_6$) δ 12.76 (s, 1H), 8.71 (s, 1H), 7.58-7.45 (m, 3H), 7.18-7.05 (m, 2H), 6.81 (dd, J=1.73, and 7.89 Hz, 1H), 6.76-6.54 (m, 4H), 4.21 (s, 2H), 3.76 (s, 3H), and 2.34 (s, 3H); LC-MS retention time (Method 2): 5.522 min; HRMS: m/z (M+H)$^+$ (Calculated for $C_{22}H_{22}N_3O_4S_2$, 456.1046). found 456.1037.

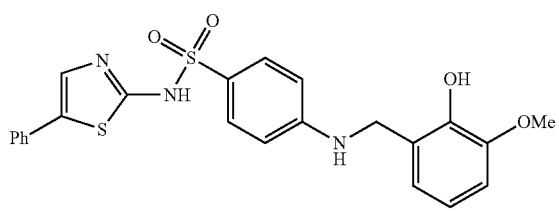

4-((2-hydroxy-3-methoxybenzyl)amino)-N-(5-phenylthiazol-2-yl)benzenesulfonamide TFA (42)

Method D: using 2-amino-5-phenylthiazole and 2-hydroxy-3-methoxybenzaldehyde; $^1$H NMR (400 MHz, DMSO-$d_6$) δ 12.59 (s, 1H), 8.70 (s, 1H), 7.68 (s, 1H), 7.56-7.25 (m, 8H), 6.87-6.78 (m, 2H), 6.79-6.62 (m, 2H), 6.61-6.53 (m, 2H), 4.21 (d, J=5.8 Hz, 2H), and 3.76 (s, 3H); LC-MS retention time (Method 2): 5.417 min; HRMS: m/z (M+H)$^+$ (Calculated for $C_{23}H_{22}N_3O_4S_2$, 468.1046). found 468.1028.

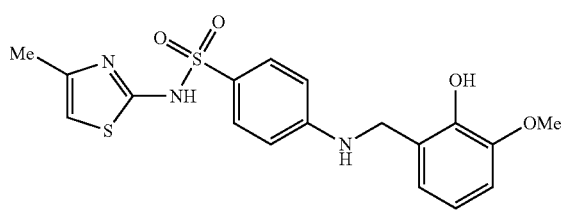 [SMILES: COc1cccc(CNc2ccc(S(=O)(=O)Nc3nc(C)cs3)cc2)c1O]

4-(2-hydroxy-3-methoxybenzylamino)-N-(4-methylthiazol-2-yl)benzenesulfonamide TFA (40)

Method C: using 2-bromo-4-methylthiazole; $^1$H NMR (400 MHz, DMSO-$d_6$) δ 12.31 (s, 1H), 8.70 (s, 1H), 7.48-7.32 (m, 3H), 6.89-6.72 (m, 6H), 6.61-6.47 (m, 3H), 6.27 (s, 1H), 4.20 (d, J=5.90 Hz, 2H), 3.76 (s, 3H), and 1.95 (s, 3H); LC-MS retention time (Method 1): 1.962 min; HRMS: m/z (M+H)$^+$ (Calculated for $C_{18}H_{20}N_3O_4S_2$, 406.0890). found 406.0875.

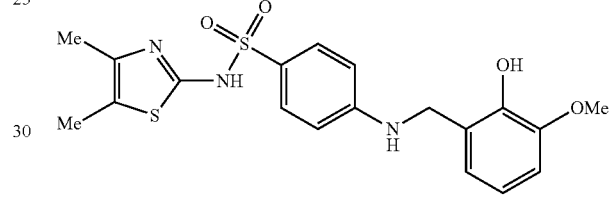

N-(4,5-dimethylthiazol-2-yl)-4-(2-hydroxy-3-methoxybenzylarnino)benzenesulfonamide TFA (43)

Method C: using 2-bromo-4,5-dimethylthiazole; $^1$H NMR (400 MHz, DMSO-$d_6$) δ 12.25 (s, 1H), 8.94 (d, J=0.71 Hz, 1H), 7.73-7.45 (m, 2H), 7.13-6.80 (m, 4H), 6.83-6.62 (m, 2H), 4.53-4.25 (m, 2H), 3.98 (d, J=0.60 Hz, 3H), ad 2.35-1.95 (m, 6H); LC-MS retention time (Method 2): 4.859 min; HRMS: m/z (M+H)$^+$ (Calculated for $C_{19}H_{21}N_3O_4S_2$, 420.1046). found 420.1037.

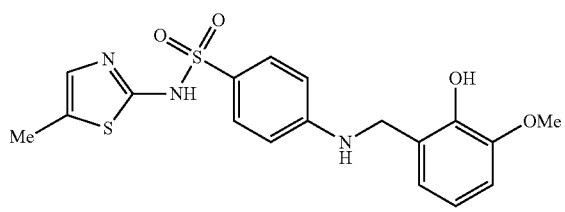 [SMILES: COc1cccc(CNc2ccc(S(=O)(=O)Nc3ncc(C)s3)cc2)c1O]

4-(2-hydroxy-3-methoxybenzylamino)-N-(5-methylthiazol-2-yl)benzenesulfonamide TFA (41)

Method D: using 2-amino-5-methylthiazole and 2-hydroxy-3-methoxybenzaldehyde; $^1$H NMR (400 MHz, DMSO-$d_6$) δ 12.05 (s, 1H), 8.73 (s, 1H), 7.46-7.38 (m, 2H), 6.91-6.63 (m, 5H), 6.59-6.51 (m, 2H), 4.20 (d, J=5.86 Hz, 2H), 3.77 (s, 3H), and 2.13 (d, J=1.39 Hz, 3H); LC-MS retention time (Method 1): 3.182 min; HRMS: m/z (M+H)$^+$ (Calculated for $C_{18}H_{20}N_3O_4S_2$, 406.0890). found 406.0889.

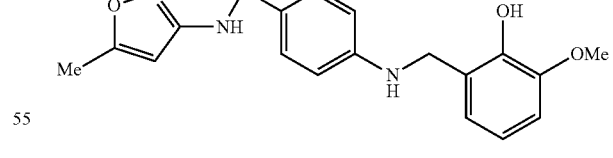

4-(2-hydroxy-3-methoxybenzylamino)-N-(5-methylisoxazol-3-yl)benzenesulfonamide TFA (44)

Method D: using 3-amino-5-methylisoxazole and 2-hydroxy-3-methoxybenzaldehyde; $^1$H NMR (400 MHz, DMSO-$d_6$) δ 10.91 (d, J=1.25 Hz, 1H), 8.76 (d, J=3.84 Hz, 1H), 7.77-7.55 (m, 1H), 7.52-7.28 (m, 2H), 7.02 (t, J=5.41 Hz, 1H), 6.77-6.64 (m, 2H), 6.63-6.51 (m, 2H), 6.11-6.02 (m, 1H), 4.27-4.14 (m, 2H), 3.77 (d, J=1.18 Hz, 3H), and 2.26 (s, 3H); LC-MS retention time (Method 2): 4.804 min; HRMS: m/z (M+H)⁺ (Calculated for C₁₈H₂₀N₃O₅S, 390.1118). found 390.1109.

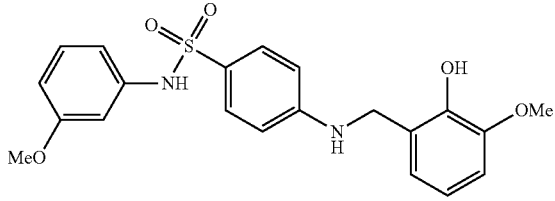 [SMILES: COc1cccc(NS(=O)(=O)c2ccc(NCc3cccc(OC)c3O)cc2)c1]

4-((2-hydroxy-3-methoxybenzyl)amino)-N-(3-methoxyphenyl)benzenesulfonamide (45)

Method C: using 1-bromo-3-methoxybenzene; ¹H NMR (400 MHz, DMSO-d₆) δ 9.87 (s, 1H), 8.73 (d, J=0.5 Hz, 1H), 7.48-7.36 (m, 2H), 7.13-7.03 (m, 1H), 6.95-6.80 (m, 2H), 6.77-6.47 (m, 7H), 4.20 (d, J=5.8 Hz, 2H), 3.78 (s, 3H), and 3.64 (s, 3H); LC-MS retention time (Method 2): 5.437 min; HRMS: m/z (M+H)⁺ (Calculated for C₂₁H₂₃N₂O₅S, 415.1322). found 415.1302.

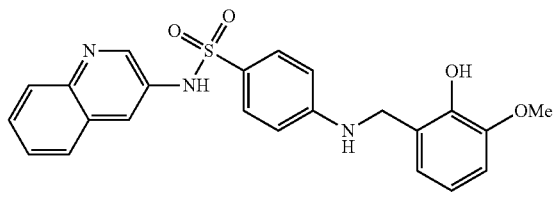 [SMILES: COc1cccc(CNc2ccc(S(=O)(=O)Nc3cnc4ccccc4c3)cc2)c1O]

4-(2-hydroxy-3-methoxybenzylamino)-N-(quinolin-3-yl)benzenesulfonamide TFA (46)

Method C: using 3-bromoquinoline; ¹H NMR (400 MHz, DMSO-d₆) δ 9.99 (d, J=1.27 Hz, 1H), 8.20 (dd, J=0.78, and 2.71 Hz, 1H), 7.60-7.33 (m, 3H), 7.17 (dddd, J=1.31, 6.90, 8.19, and 31.70 Hz, 3H), 7.09-7.04 (m, 2H), 6.41 (dd, J=1.94, 7.69 Hz, 1H), 6.30-6.20 (m, 2H), 6.17-6.10 (m, 2H), 3.76 (s, 2H), and 3.36 (s, 3H); LC-MS retention time (Method 1): 2.304 min; HRMS: m/z (M+H)⁺ (Calculated for C₂₃H₂₂N₃O₄S, 436.1326). found 436.1316.

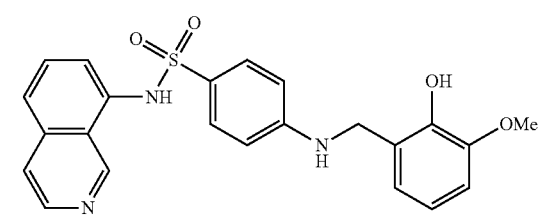 [SMILES: COc1cccc(CNc2ccc(S(=O)(=O)Nc3cccc4ccncc34)cc2)c1O]

4-(2-hydroxy-3-methoxybenzylamino)-N-(isoquinolin-8-yl)benzenesulfonamide (47)

Method C: using 8-bromoisoquinoline; ¹H NMR (400 MHz, DMSO-d₆) δ 10.34-10.24 (s, 1H), 9.56 (s, 1H), 8.74 (s, 1H), 8.54 (d, J=5.95 Hz, 1H), 8.02 (d, J=5.96 Hz, 1H), 7.91-7.73 (m, 2H), 7.44-7.29 (m, 3H), 6.85 (t, J=4.80 Hz, 1H), 6.76-6.62 (m, 2H), 6.61-6.44 (m, 2H), 4.19 (s, 2H), and 3.79 (s, 3H); LC-MS retention time (Method 1): 1.914 min; HRMS: m/z (M+Na)⁺ (Calculated for C₂₃H₂₁NaN₃O₄S, 458.1145) found 458.1129.

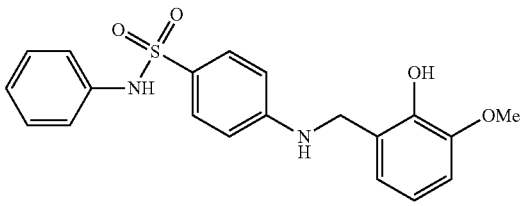

4-(2-hydroxy-3-methoxybenzylamino)-N-phenyl-benzenesulfonamide TFA (48)

Method C: using bromobenzene; ¹H NMR (400 MHz, DMSO-d₆) δ 9.85 (s, 1H), 8.73 (d, J=2.23 Hz, 1H), 7.42-7.34 (m, 2H), 7.21-7.12 (m, 2H), 7.06-6.99 (m, 2H), 6.98-6.91 (m, 1H), 6.82 (dd, J=1.86, and 7.72 Hz, 1H), 6.74-6.64 (m, 2H), 6.57-6.49 (m, 2H), 4.31-3.99 (m, 2H), and 3.76 (s, 3H); LC-MS retention time (Method 1): 2.750 min; HRMS: m/z (M+H)⁺ (Calculated for C₂₀H₂₁N₂O₄S, 385.1217). found 385.1223.

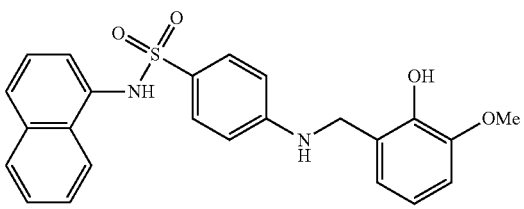 [SMILES: COc1cccc(CNc2ccc(S(=O)(=O)Nc3cccc4ccccc34)cc2)c1O]

4-((2-hydroxy-3-methoxybenzyl)amino)-N-(naphthalen-1-yl)benzenesulfonamide (49)

Method D: using naphthalen-1-amine and 2-hydroxy-3-methoxybenzaldehyde; ¹H NMR (400 MHz, DMSO-d₆) δ 9.74 (s, 1H), 8.73 (s, 1H), 8.06 (ddd, J=0.74, 1.48, and 8.45 Hz, 1H), 7.89-7.82 (m, 1H), 7.72 (d, J=8.15 Hz, 1H), 7.54-7.27 (m, 5H), 7.15 (dd, J=1.05, and 7.45 Hz, 1H), 6.85 (q, J=4.87 Hz, 2H), 6.75-6.66 (m, 2H), 6.57-6.47 (m, 2H), 4.19 (d, J=5.65 Hz, 2H), and 3.79 (s, 3H); LC-MS retention time (Method 1): 2.744 min; HRMS: m/z (M+H)⁺ (Calculated for C₂₄H₂₃N₂O₄S, 435.1373). found 435.1392.

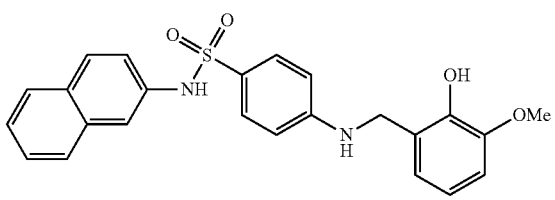 [SMILES: COc1cccc(CNc2ccc(S(=O)(=O)Nc3ccc4ccccc4c3)cc2)c1O]

4-((2-hydroxy-3-methoxybenzyl)amino)-N-(naphthalen-2-yl)benzenesulfonamide (50)

Method D: using naphthalen-2-amine and 2-hydroxy-3-methoxybenzaldehyde; ¹H NMR (400 MHz, DMSO-d₆) δ

10.11 (d, J=1.4 Hz, 1H), 8.71 (s, 1H), 7.81-7.67 (m, 3H), 7.54-7.30 (m, 5H), 7.27 (dt, J=1.9, and 8.8 Hz, 1H), 6.94-6.76 (m, 2H), 6.76-6.61 (m, 2H), 6.53 (dd, J=8.8, 1.7 Hz, 2H), 4.16 (s, 2H), and 3.77 (s, 3H); LC-MS retention time (Method 1): 3.281 min; HRMS: m/z (M+H)$^+$ (Calculated for C$_{24}$H$_{23}$N$_2$O$_4$S, 435.1373). found 435.1373.

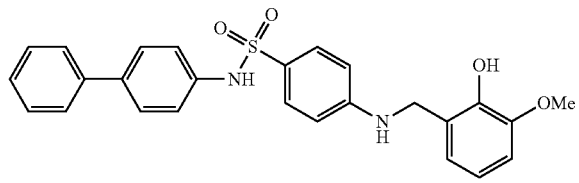 [SMILES: COc1cccc(CNc2ccc(S(=O)(=O)Nc3ccc(-c4ccccc4)cc3)cc2)c1O]

N-([1,1'-biphenyl]-4-yl)-4-((2-hydroxy-3-methoxybenzyl)amino)benzenesulfonamide (51)

Method D: using biphenyl-4-amine and 2-hydroxy-3-methoxybenzaldehyde; $^1$H NMR (400 MHz, DMSO-d$_6$) δ 9.99 (s, 1H), 8.72 (s, 1H), 7.60-7.35 (m, 8H), 7.34-7.24 (m, 1H), 7.18-7.09 (m, 2H), 6.90 (t, J=5.9, Hz, 1H), 6.82 (dd, J=1.7, and 7.8 Hz, 1H), 6.76-6.62 (m, 2H), 6.61-6.52 (m, 2H), 4.19 (d, J=5.8 Hz, 2H), and 3.77 (s, 3H); LC-MS retention time (Method 2): 6.433 min; HRMS: m/z (M+H)$^+$ (Calculated for C$_{26}$H$_{25}$N$_2$O$_4$S, 461.1530). found 461.1529.

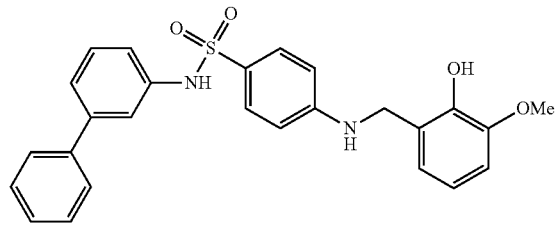 [SMILES: COc1cccc(CNc2ccc(S(=O)(=O)Nc3cccc(-c4ccccc4)c3)cc2)c1O]

N-([1,1'-biphenyl]-3-yl)-4-((2-hydroxy-3-methoxybenzyl)amino)benzenesulfonamide (52)

Method C: using 3-bromo-1,1'-biphenyl; $^1$H NMR (400 MHz, DMSO-d$_6$) δ 9.98 (s, 1H), 8.72 (s, 1H), 7.55-7.19 (m, 11H), 7.06 (ddd, J=1.5, 2.2, and 7.6 Hz, 1H), 6.96-6.73 (m, 2H), 6.75-6.49 (m, 4H), 4.20 (d, J=5.8 Hz, 2H), and 3.78 (s, 3H); LC-MS retention time (Method 2): 6.131 min; HRMS: m/z (M+H)$^+$ (Calculated for C$_{26}$H$_{25}$N$_2$O$_4$S, 461.1530). found 461.1521.

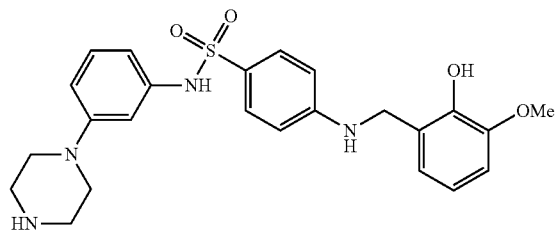 [SMILES: COc1cccc(CNc2ccc(S(=O)(=O)Nc3cccc(N4CCNCC4)c3)cc2)c1O]

4-((2-hydroxy-3-methoxybenzyl)amino)-N-(3-(piperazin-1-yl)phenyl)benzenesulfonamide (53)

Method 1C: using tert-butyl 4-(3-bromophenyl)piperazine-1-carboxylate and the Boc group was removed after the reductive amination with 4 M HCl in dioxanes over a 30 min period. $^1$H NMR (400 MHz, DMSO-d$_6$) δ 9.80 (s, 1H), 8.75 (s, 1H), 7.47-7.38 (m, 2H), 7.05 (t, J=8.12 Hz, 1H), 6.95-6.81 (m, 2H), 6.77-6.65 (m, 3H), 6.64-6.51 (m, 4H), 4.20 (d, J=5.58 Hz, 2H), 3.79 (s, 3H), 3.21 (s, 8H), and 0.88-0.76 (m, 1H); LC-MS retention time (Method 1): 1.660 min; HRMS: m/z (M+H)$^+$ (Calculated for C$_{24}$H$_{29}$N$_4$O$_4$S, 469.1904). found 469.1897.

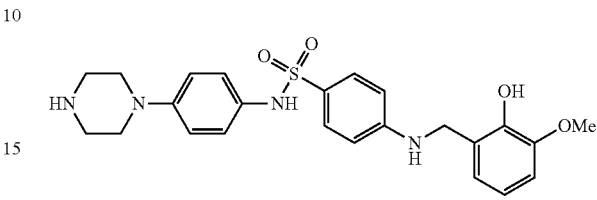

4-(2-hydroxy-3-methoxybenzylamino)-N-(4-(piperazin-1-yl)phenyl)benzenesulfonamide (54)

Method D: using tert-butyl 4-(4-aminophenyl)piperidine-1-carboxylate and 2-hydroxy-3-methoxybenzaldehyde. The Boc group was removed after the reductive amination with 4 M HCl/dioxanes for 1 h at rt. $^1$H NMR (400 MHz, DMSO-d$_6$) δ 9.50 (s, 1H), 8.74 (d, J=0.47 Hz, 1H), 7.39-7.30 (m, 2H), 6.98-6.79 (m, 6H), 6.78-6.65 (m, 2H), 6.59-6.50 (m, 2H), 4.20 (d, J=5.63 Hz, 2H), 3.79 (s, 3H), and 3.19 (s, 8H); LC-MS retention time (Method 1): 1.648 min; HRMS: m/z (M+H)$^+$ (Calculated for C$_{24}$H$_{29}$N$_4$O$_4$S, 469.1904). found 469.1900.

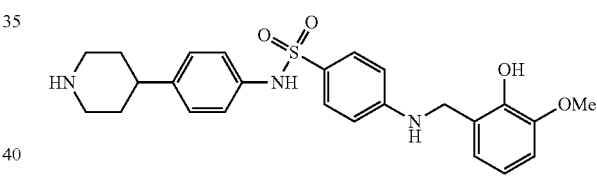

4-((2-hydroxy-3-methoxybenzyl)amino)-N-(4-(piperidin-4-yl)phenyl)benzenesulfonamide (55)

Method D: using tert-butyl 4-(4-aminophenyl)piperidine-1-carboxylate and 2-hydroxy-3-methoxybenzaldehyde. The Boc group was removed after the reductive amination with 4 M HCl in dioxane for 1 h at rt. $^1$H NMR (400 MHz, DMSO-d$_6$) δ 10.03 (s, 1H), 8.92 (d, J=0.5 Hz, 1H), 7.63-7.56 (m, 2H), 7.32-7.15 (m, 6H), 6.95-6.82 (m, 2H), 6.78-6.68 (m, 2H), 4.37 (d, J=5.7 Hz, 2H), 3.96 (s, 3H), 3.57-3.42 (m, 4H), 3.14-3.01 (m, 4H), and 2.90 (d, J=11.4 Hz, 1H); LC-MS retention time (Method 1): 1.710 min; HRMS: m/z (M+H)$^+$ (Calculated for C$_{25}$H$_{30}$N$_3$O$_4$S, 468.1952). found 468.1935.

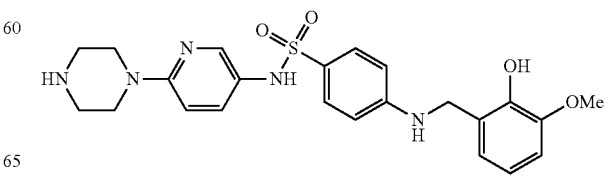

4-(2-hydroxy-3-methoxybenzylamino)-N-(6-(piperazin-1-yl)pyridin-3-yl)benzenesulfonamide (56)

Method C: using tert-butyl 4-(5-bromopyridin-2-yl)piperazine-1-carboxylate, and the Boc group was removed after the reductive amination with 4 M HCl/dioxanes over a 1 h. $^1$H NMR (400 MHz, DMSO-d$_6$) δ 9.57 (s, 1H), 9.12 (d, J=7.21 Hz, 2H), 7.74 (d, J=2.65 Hz, 1H), 7.31 (dd, J=4.87, and 7.36 Hz, 2H), 7.07 (s, 1H), 6.89-6.80 (m, 2H), 6.76-6.59 (m, 2H), 6.60-6.51 (m, 2H), 4.19 (s, 2H), 3.77 (s, 3H), 3.75-3.53 (m, 4H), and 3.17-3.07 (m, 4H); LC-MS retention time (Method 1): 1.993 min; HRMS: m/z (M+H)$^+$ (Calculated for C$_{23}$H$_{28}$N$_5$O$_4$S, 470.1857). found 470.1848.

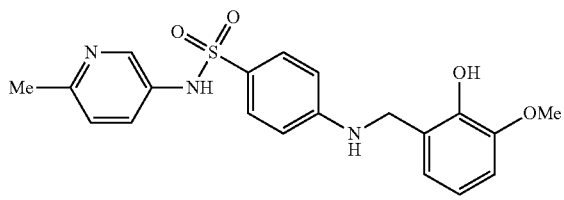 [SMILES: COc1cccc(CNc2ccc(S(=O)(=O)Nc3ccc(C)nc3)cc2)c1O]

4-(2-hydroxy-3-methoxybenzylamino)-N-(6-methylpyridin-3-yl)benzenesulfonamide (57)

Method C: using 5-bromo-2-methylpyridine; $^1$H NMR (400 MHz, DMSO-d$_6$) δ 10.10 (s, 1H), 8.61 (s, 1H), 8.02 (dd, J=0.68, 2.63 Hz, 1H), 7.47-7.39 (m, 1H), 7.32-7.23 (m, 2H), 7.18 (d, J=8.47 Hz, 1H), 6.70 (dd, J=1.92, and 7.68 Hz, 1H), 6.63-6.50 (m, 2H), 6.48-6.40 (m, 2H), 4.06 (s, 2H), 3.64 (s, 3H), and 2.28 (s, 3H); LC-MS retention time (Method 1): 1.840 min; HRMS: m/z (M+H)$^+$ (Calculated for C$_{20}$H$_{22}$N$_3$O$_4$S, 400.1326). found 400.1315.

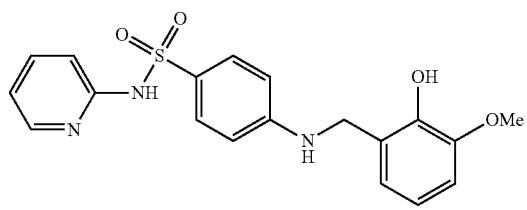 [SMILES: COc1cccc(CNc2ccc(S(=O)(=O)Nc3ccccn3)cc2)c1O]

4-(2-hydroxy-3-methoxybenzylamino)-N-(pyridin-2-yl)benzenesulfonamide (58)

Method C: using 2-bromopyridine; $^1$H NMR (400 MHz, DMSO-d$_6$) δ 8.71 (d, J=0.54 Hz, 1H), 8.11-7.96 (m, 1H), 7.65-7.58 (m, 1H), 7.52 (d, J=8.70 Hz, 2H), 7.09-6.98 (m, 1H), 6.92-6.79 (m, 3H), 6.76-6.63 (m, 2H), 6.58-6.50 (m, 2H), 4.19 (d, J=5.83 Hz, 2H), and 3.77 (s, 3H); LC-MS retention time (Method 2): 4.540 min; HRMS: m/z (M+H)$^+$ (Calculated for C$_{19}$H$_{20}$N$_3$O$_4$S, 386.1169). found 386.1158.

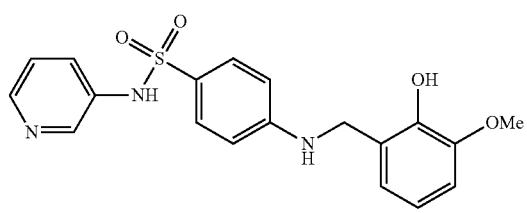 [SMILES: COc1cccc(CNc2ccc(S(=O)(=O)Nc3cccnc3)cc2)c1O]

4-(2-hydroxy-3-methoxybenzylamino)-N-(pyridin-3-yl)benzenesulfonamide (59)

Method C: using 3-bromopyridine; $^1$H NMR (400 MHz, DMSO-d$_6$) δ 10.30 (s, 1H), 8.73 (s, 1H), 8.31-8.21 (m, 2H), 7.57 (ddd, J=1.38, 2.63, and 8.37 Hz, 1H), 7.46-7.32 (m, 3H), 6.83 (dd, J=1.92, and 7.71 Hz, 1H), 6.75-6.62 (m, 2H), 6.61-6.51 (m, 2H), 4.19 (s, 2H), 3.77 (s, 3H); LC-MS retention time (Method 1): 1.804 min; HRMS: m/z (M+H)$^+$ (Calculated for C$_{19}$H$_{20}$N$_3$O$_4$S, 386.1169). found 386.1166.

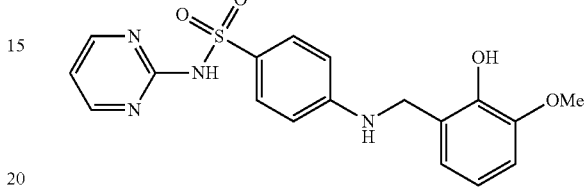

4-(2-hydroxy-3-methoxybenzylamino)-N-(pyrimidin-2-yl)benzenesulfonamide TFA (60)

Method C: using 2-bromopyrimidine; $^1$H NMR (400 MHz, DMSO-d$_6$) δ 11.25 (s, 1H), 8.77 (s, 1H), 8.48 (d, J=4.83 Hz, 2H), 7.72-7.50 (m, 2H), 6.99 (dt, J=5.43, and 15.84 Hz, 2H), 6.85 (dd, J=1.69, and 7.85 Hz, 1H), 6.77-6.66 (m, 2H), 6.62-6.56 (m, 2H), 4.23 (d, J=5.65 Hz, 2H), and 3.79 (s, 3H); LC-MS retention time (Method 2): 4.266 min; HRMS: m/z (M+H)$^+$ (Calculated for C$_{18}$H$_{19}$N$_4$O$_4$S, 387.1122). found 387.1115.

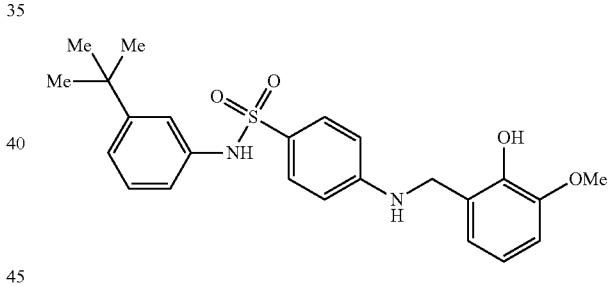

N-(3-(tert-butyl)phenyl)-4-((2-hydroxy-3-methoxybenzyl)amino)benzenesulfonamide, TFA (61)

Method C: using 1-bromo-3-(tert-butyl)benzene; $^1$H NMR (400 MHz, DMSO-d$_6$) δ 9.71 (s, 1H), 8.71 (s, 1H), 7.42-7.32 (m, 2H), 7.14-6.93 (m, 3H), 6.93-6.78 (m, 3H), 6.73-6.60 (m, 2H), 6.58-6.47 (m, 2H), 4.18 (s, 2H), 3.76 (s, 3H), and 1.14 (s, 9H); LC-MS retention time (Method 2): 6.184 min; HRMS: m/z (M+H)$^+$ (Calculated for C$_{24}$H$_{29}$N$_2$O$_4$S, 441.0843). found 441.1844.

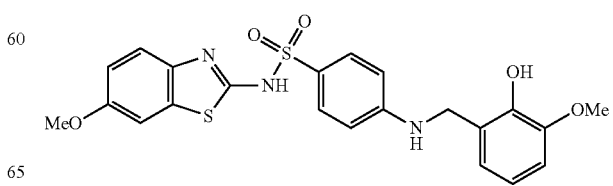

4-((2-hydroxy-3-methoxybenzyl)amino)-N-(6-methoxybenzo[d]thiazol-2-yl)benzenesulfonamide, TFA (62)

Method C: using 2-bromo-6-methoxybenzo[d]thiazole; $^1$H NMR (400 MHz, DMSO-$d_6$) δ 12.70 (s, 1H), 8.71 (d, J=0.47 Hz, 1H), 7.51-7.41 (m, 2H), 7.38 (d, J=2.54 Hz, 1H), 7.14 (d, J=8.76 Hz, 1H), 6.96-6.78 (m, 3H), 6.76-6.62 (m, 2H), 6.61-6.53 (m, 2H), 4.21 (d, J=5.89 Hz, 2H), 3.75 (s, 3H), and 3.73 (s, 3H); LC-MS retention time (Method 2): 5.278 min; HRMS: m/z (M+H)$^+$ (Calculated for $C_{22}H_{22}N_3O_5S_2$, 472.0995). found 472.0998.

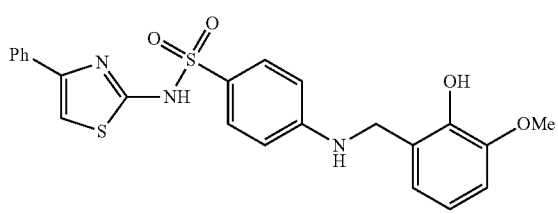 [SMILES: COc1cccc(CNc2ccc(S(=O)(=O)Nc3nc(-c4ccccc4)cs3)cc2)c1O]

4-((2-hydroxy-3-methoxybenzyl)amino)-N-(4-phenylthiazol-2-yl)benzenesulfonamide, TFA (63)

Method C: using 2-bromo-4-phenylthiazole; $^1$H NMR (400 MHz, DMSO-$d_6$) δ 8.72 (s, 1H), 7.67 (d, J=7.47 Hz, 2H), 7.53-7.24 (m, 6H), 7.08 (d, J=19.97 Hz, 1H), 6.92-6.45 (m, 6H), 4.21 (d, J=5.55 Hz, 2H), and 3.77 (s, 3H); LC-MS retention time (Method 2): 5.200 min; HRMS: m/z (M+H)$^+$ (Calculated for $C_{23}H_{22}N_3O_4S$, 468.1046). found 468.1066.

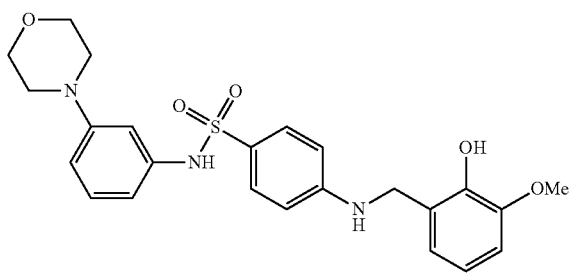 [SMILES: COc1cccc(CNc2ccc(S(=O)(=O)Nc3cccc(N4CCOCC4)c3)cc2)c1O]

4-((2-hydroxy-3-methoxybenzyl)amino)-N-(3-morpholinophenyl)benzenesulfonamide, TFA (64)

Method C: using 4-(3-bromophenyl)morpholine; $^1$H NMR (400 MHz, DMSO-$d_6$) δ 9.70 (s, 1H), 8.72 (s, 1H), 7.46-7.34 (m, 2H), 7.00 (t, J=8.09 Hz, 1H), 6.82 (dd, J=1.86, and 7.75 Hz, 2H), 6.76-6.43 (m, 7H), 4.19 (s, 2H), 3.77 (s, 3H), 3.71-3.59 (m, 4H), and 2.98-2.86 (m, 4H); LC-MS retention time (Method 2): 4.961 min; HRMS: m/z (M+H)$^+$ (Calculated for $C_{24}H_{28}N_3O_5S$, 470.1744). found 470.1753.

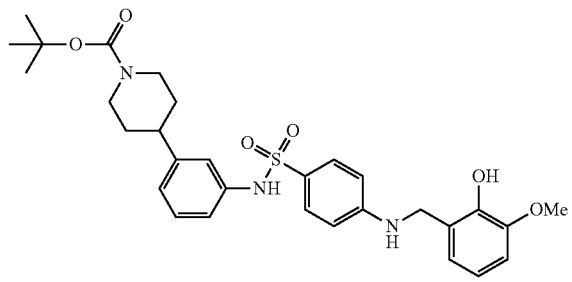 [SMILES: COc1cccc(CNc2ccc(S(=O)(=O)Nc3cccc(C4CCN(C(=O)OC(C)(C)C)CC4)c3)cc2)c1O]

tert-butyl 4-(3-(4-((2-hydroxy-3-methoxybenzyl)amino)phenylsulfonamido)phenyl)piperidine-1-carboxylate (65)

Method C: using tert-butyl-4-(3-bromophenyl)piperidine-1-carboxylate; $^1$H NMR (400 MHz, DMSO-$d_6$) δ 8.71 (s, 1H), 7.46-7.28 (m, 2H), 7.08 (t, J=7.74 Hz, 1H), 6.94-6.75 (m, 6H), 6.75-6.59 (m, 2H), 6.59-6.44 (m, 2H), 4.18 (d, J=5.82 Hz, 2H), 4.00 (d, J=12.83 Hz, 2H), 3.76 (s, 3H), 2.59-2.50 (m, 1H), 1.62 (d, J=12.87 Hz, 2H), 1.39 (s, 9H), and 1.31 (m, 4H); LC-MS retention time (Method 2): 6.322 min; HRMS: m/z (M+H)$^+$ (Calculated for $C_{30}H_{38}N_3O_6S$, 568.2476). found 568.2461.

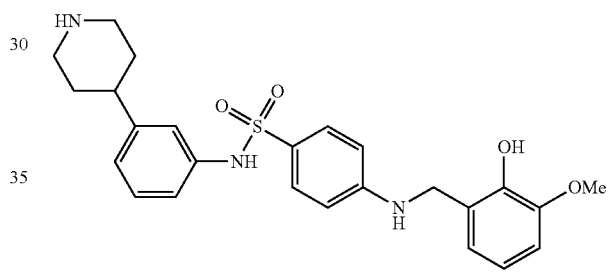

4-((2-hydroxy-3-methoxybenzyl)amino)-N-(3-(piperidin-4-yl)phenyl)benzenesulfonamide, TFA (66)

Method 1C: using tert-butyl-4-(3-bromophenyl)piperidine-1-carboxylate the Boc group was removed after the reductive amination with 4 M HCl/dioxanes over a 30 min period. $^1$H NMR (400 MHz, DMSO-$d_6$) δ 8.73 (s, 1H), 7.53-7.24 (m, 2H), 7.12 (t, J=7.85 Hz, 1H), 6.99 (t, J=1.96 Hz, 1H), 6.93-6.77 (m, 4H), 6.73-6.61 (m, 2H), 6.57-6.48 (m, 2H), 4.33-4.01 (m, 2H), 3.77 (s, 3H), 3.33 (s, 1H), 2.95 (t, J=12.62 Hz, 2H), 2.83-2.55 (m, 1H), and 1.94-1.43 (m, 4H); LC-MS retention time (Method 2): 4.079 min; HRMS: m/z (M+H)$^+$ (Calculated for $C_{25}H_{30}N_4O_4S$, 468.1952). found 468.1948.

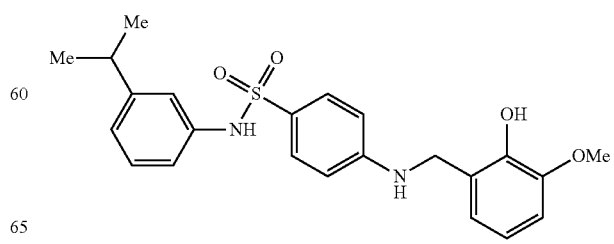

4-((2-hydroxy-3-methoxybenzyl)amino)-N-(3-isopropylphenyl)benzenesulfonamide, TFA (67)

Method C: using 1-bromo-3-isopropylbenzene; $^1$H NMR (400 MHz, DMSO-$d_6$) δ 9.73 (s, 1H), 8.70 (s, 1H), 7.42-7.32 (m, 2H), 7.07 (t, J=7.77 Hz, 1H), 6.98-6.75 (m, 4H), 6.73-6.61 (m, 2H), 6.58-6.45 (m, 2H), 4.18 (s, 2H), 3.76 (d, J=0.87 Hz, 3H), 2.72 (h, J=6.82 Hz, 1H), and 1.07 (dd, J=0.91, and 6.94 Hz, 6H); LC-MS retention time (Method 2): 6.040 min; HRMS: m/z (M+H)$^+$ (Calculated for $C_{23}H_{27}N_2O_4S$, 427.1686). found 427.1680.

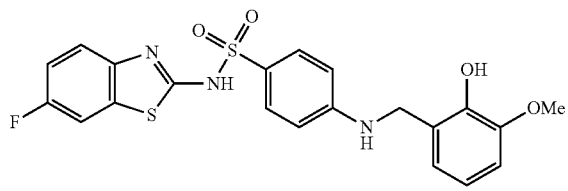 [SMILES: COc1cccc(CNc2ccc(S(=O)(=O)Nc3nc4ccc(F)cc4s3)cc2)c1O]

N-(6-fluorobenzo[d]thiazol-2-yl)-4-((2-hydroxy-3-methoxybenzyl)amino) benzenesulfonamide, TFA (68)

Method C: using 2-bromo-6-fluorobenzo[d]thiazole; $^1$H NMR (400 MHz, DMSO-$d_6$) δ 8.72 (s, 1H), 7.69 (dd, J=2.43, and 8.51 Hz, 1H), 7.54-7.39 (m, 2H), 7.19 (qd, J=3.40, 8.25, and 8.85 Hz, 3H), 6.88 (t, J=5.68 Hz, 1H), 6.81 (dd, J=1.71, and 7.87 Hz, 1H), 6.74-6.63 (m, 2H), 6.60-6.54 (m, 2H), 4.21 (d, J=5.90 Hz, 2H), and 3.76 (s, 3H); LC-MS retention time (Method 2): 5.164 min; HRMS: m/z (M+H)$^+$ (Calculated for $C_{21}H_{19}FN_3O_4S_2$, 460.0796). found 460.0797.

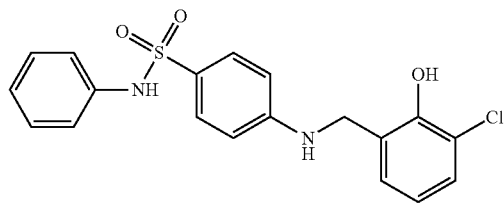 [SMILES: O=S(=O)(Nc1ccccc1)c1ccc(NCc2cccc(Cl)c2O)cc1]

4-(3-chloro-2-hydroxybenzylamino)-N-phenylbenzenesulfonamide, TFA (69)

Method C: using 3-chloro-2-hydroxybenzaldehyde and bromobenzene; $^1$H NMR (400 MHz, DMSO-$d_6$) δ 9.88 (s, 1H), 9.38 (s, 1H), 7.47-7.34 (m, 2H), 7.28-7.14 (m, 3H), 7.11-7.01 (m, 3H), 7.01-6.88 (m, 2H), 6.79 (t, J=7.78 Hz, 1H), 6.60-6.50 (m, 2H), and 4.29-4.23 (m, 2H); LC-MS retention time (Method 2): 5.442 min; HRMS: m/z (M+H)$^+$ (Calculated for $C_{19}H_{18}ClN_2O_3S$, 389.0721). found 389.0702.

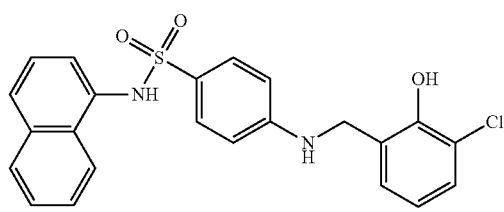 [SMILES: O=S(=O)(Nc1cccc2ccccc12)c1ccc(NCc2cccc(Cl)c2O)cc1]

4-(3-chloro-2-hydroxybenzylamino)-N-(naphthalen-1-yl)benzenesulfonamide, TFA (70)

Method D: using naphthalen-1-amine and 3-chloro-2-hydroxybenzaldehyde; $^1$H NMR (400 MHz, DMSO-$d_6$) δ 9.75 (s, 1H), 9.36 (s, 1H), 8.03 (dd, J=1.20, and 8.53 Hz, 1H), 7.90-7.80 (m, 1H), 7.70 (d, J=8.22 Hz, 1H), 7.54-7.28 (m, 3H), 7.23 (dd, J=1.58, and 8.01 Hz, 1H), 7.15 (dd, J=1.08, and 7.40 Hz, 1H), 7.02 (dd, J=1.58, and 7.65 Hz, 1H), 6.90 (t, J=5.82 Hz, 1H), 6.78 (t, J=7.79 Hz, 1H), 6.57-6.42 (m, 2H), and 4.24 (d, J=4.97 Hz, 2H); LC-MS retention time (Method 1): 2.755 min; HRMS: m/z (M+H)$^+$ (Calculated for $C_{23}H_{20}ClN_2O_3S$, 439.0878). found 439.0862.

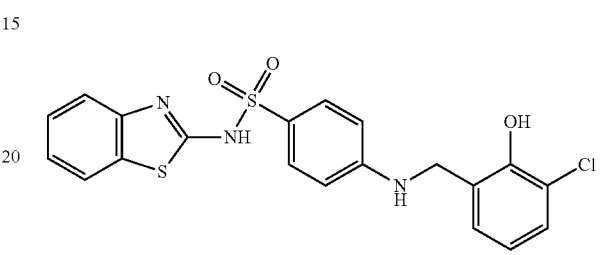

N-(benzo[d]thiazol-2-yl)-4-(3-chloro-2-hydroxybenzylamino)benzenesulfonamide, TFA (71)

Method C: using 3-chloro-2-hydroxybenzaldehyde and 2-bromobenzthiazole; $^1$H NMR (400 MHz, DMSO-$d_6$) δ 12.88 (s, 1H), 9.38 (s, 1H), 7.80-7.69 (m, 1H), 7.59-7.46 (m, 2H), 7.35 (ddd, J=1.24, 7.44, and 8.26 Hz, 1H), 7.31-7.13 (m, 3H), 7.12-7.02 (m, 1H), 6.95 (t, J=5.93 Hz, 1H), 6.78 (t, J=7.79 Hz, 1H), 6.69-6.52 (m, 2H), and 4.28 (d, J=5.72 Hz, 2H); LC-MS retention time (Method 2): 5.258 min; HRMS: m/z (M+H)$^+$ (Calculated for $C_{20}H_{17}ClN_3O_3S_2$, 446.0390) found 446.0379.

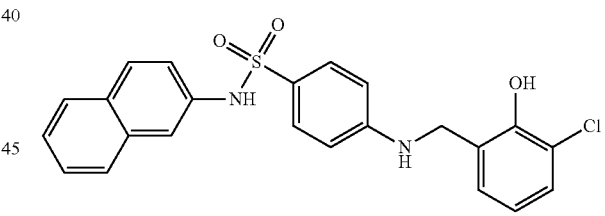

4-(3-chloro-2-hydroxybenzylamino)-N-(naphthalen-2-yl)benzenesulfonamide, TFA (72)

Method D: using naphthalen-2-amine and 3-chloro-2-hydroxybenzaldehyde; LC-MS retention time (Method 1): 2.637 min; HRMS: m/z (M+H)$^+$ (Calculated for $C_{23}H_{20}ClN_2O_3S$, 439.0878). found 439.0867.

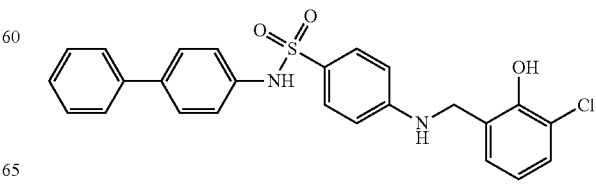

N-([1,1'-biphenyl]-4-yl)-4-((3-chloro-2-hydroxybenzyl)amino)benzenesulfonamide, TFA (73)

Method D: using biphenyl-4-amine and 3-chloro-2-hydroxybenzaldehyde; $^1$H NMR (400 MHz, DMSO-d$_6$) δ 10.03 (s, 1H), 9.37 (s, 1H), 7.61-7.36 (m, 9H), 7.35-7.04 (m, 5H), 6.97 (t, J=5.8 Hz, 1H), 6.78 (t, J=7.8 Hz, 1H), 6.62-6.52 (m, 2H), and 4.26 (d, J=5.7 Hz, 2H); LC-MS retention time (Method 2): 6.592 min; HRMS: m/z (M+H)$^+$ (Calculated for C$_{25}$H$_{22}$ClN$_2$O$_3$S, 465.1034). found 465.1021.

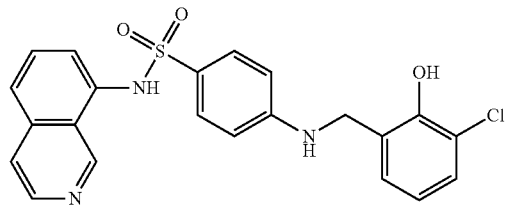 [SMILES: O=S(=O)(Nc1cccc2ccncc12)c1ccc(NCc2cccc(Cl)c2O)cc1]

4-(3-chloro-2-hydroxybenzylamino)-N-(isoquinolin-8-yl)benzenesulfonamide, TFA (74)

Method C: using 3-chloro-2-hydroxybenzaldehyde and 8-bromoisoquinoline; $^1$H NMR (400 MHz, DMSO-d$_6$) δ 9.60 (s, 1H), 8.55 (d, J=6.0 Hz, 1H), 8.09 (d, J=6.0 Hz, 1H), 7.99-7.71 (m, 2H), 7.46-7.29 (m, 3H), 7.23 (dd, J=1.6, and 7.9 Hz, 1H), 7.11-6.93 (m, 1H), 6.78 (t, J=7.8 Hz, 1H), 6.64-6.39 (m, 2H), and 4.24 (s, 2H); LC-MS retention time (Method 1): 1.669 min; HRMS: m/z (M+H)$^+$ (Calculated for C$_{22}$H$_{19}$ClN$_3$O$_3$S, 440.0830). found 440.0811.

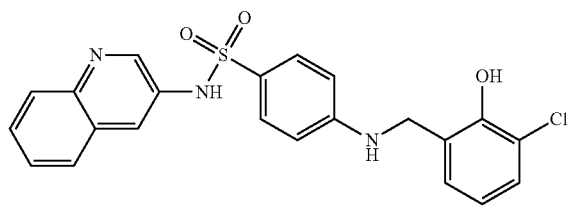 [SMILES: O=S(=O)(Nc1cnc2ccccc2c1)c1ccc(NCc2cccc(Cl)c2O)cc1]

4-(3-chloro-2-hydroxybenzylamino)-N-(quinolin-3-yl)benzenesulfonamide, TFA (75)

Method C: using 3-chloro-2-hydroxybenzaldehyde and 3-bromoquinoline; LC-MS retention time (Method 1): 2.346 min; HRMS: m/z (M+H)$^+$ (Calculated for C$_{22}$H$_{19}$ClN$_3$O$_3$S, 440.0830). found 440.0824.

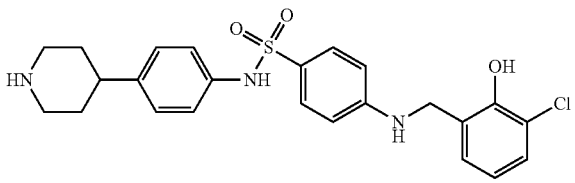 [SMILES: O=S(=O)(Nc1ccc(C2CCNCC2)cc1)c1ccc(NCc2cccc(Cl)c2O)cc1]

4-(3-chloro-2-hydroxybenzylamino)-N-(4-(piperidin-4-yl)phenyl)benzenesulfonamide, TFA (76)

Method D: using tert-butyl-4-(4-aminophenyl)piperidine-1-carboxylate and 3-chloro-2-hydroxybenzaldehyde. The Boc group was removed after the reductive amination with 4 M HCl in dioxane over a 30 min period. $^1$H NMR (400 MHz, DMSO-d$_6$) δ 10.20 (s, 1H), 9.71 (s, 1H), 7.87-7.59 (m, 2H), 7.57 (dd, J=1.64, and 7.96 Hz, 1H), 7.48-7.15 (m, 6H), 7.21-7.02 (m, 1H), 6.96-6.69 (m, 2H), 4.59 (d, J=5.77 Hz, 2H), 3.64 (s, 2H), 3.27 (t, J=12.85 Hz, 3H), 3.10-2.93 (m, 1H), 2.18 (d, J=13.73 Hz, 2H), and 1.98 (qd, J=4.00, and 13.16 Hz, 2H); LC-MS retention time (Method 1): 2.884 min; HRMS: m/z (M+H)$^+$ (Calculated for C$_{23}$H$_{20}$ClN$_2$O$_3$S, 472.1456). found 472.1442.

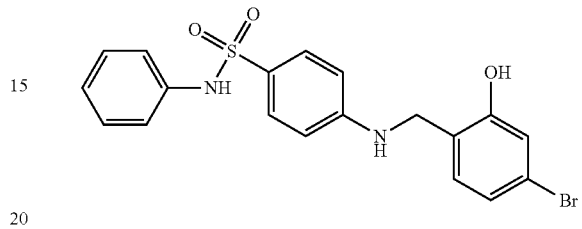

4-(4-bromo-2-hydroxybenzylamino)-N-phenylbenzenesulfonamide, TFA (77)

Method D: using 4-bromo-2-hydroxybenzaldehyde and benzylamine; $^1$H NMR (400 MHz, DMSO-d$_6$) δ 10.09 (s, 1H), 9.85 (s, 1H), 7.52-7.28 (m, 2H), 7.28-7.12 (m, 2H), 7.12-6.78 (m, 7H), 6.63-6.41 (m, 2H), 4.12 (d, J=2.80 Hz, 2H); LC-MS retention time (Method 2): 5.501 min; HRMS: m/z (M+H)$^+$ (Calculated for C$_{19}$H$_{18}$BrN$_2$O$_3$S, 434.0246). found 434.0239.

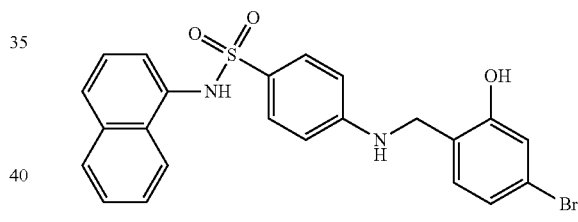

4-(4-bromo-2-hydroxybenzylamino)-N-(naphthalen-1-yl)benzenesulfonamide (78)

Method D: using 1-amino-naphthalene and 4-bromo-2-hydroxybenzaldehyde; $^1$H NMR (400 MHz, DMSO-d$_6$) δ 10.09 (d, J=1.50 Hz, 1H), 9.74 (s, 1H), 8.03 (dd, J=1.23, and 8.56 Hz, 1H), 7.87-7.80 (m, 1H), 7.70 (d, J=8.24 Hz, 1H), 7.45 (ddd, J=1.23, 6.81, and 8.11 Hz, 1H), 7.41-7.28 (m, 4H), 7.17-7.09 (m, 1H), 7.01-6.94 (m, 2H), 6.92-6.81 (m, 2H), 6.53-6.42 (m, 2H), and 4.12 (s, 2H); LC-MS retention time (Method 2): 6.282 min; HRMS: m/z (M+H)$^+$ (Calculated for C$_{23}$H$_{20}$BrN$_2$O$_3$S, 483.0373). found 483.0367.

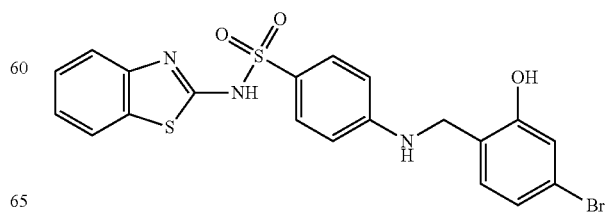

N-(benzo[d]thiazol-2-yl)-4-(4-bromo-2-hydroxybenzylamino)benzenesulfonamide, TFA (79)

Method D: using 2-aminobenzothiazole and 4-bromo-2-hydroxybenzaldehyde; $^1$H NMR (400 MHz, DMSO-d$_6$) δ 13.15 (s, 1H), 10.38 (s, 1H), 8.07-7.95 (m, 1H), 7.85-7.68 (m, 2H), 7.62 (ddd, J=1.22, 7.36, and 8.30 Hz, 1H), 7.54-7.40 (m, 2H), 7.37-7.04 (m, 5H), 6.93-6.67 (m, 2H), and 4.43 (d, J=5.75 Hz, 2H); LC-MS retention time (Method 1): 2.505 min; HRMS: m/z (M+H)$^+$ (Calculated for C$_{20}$H$_{17}$BrN$_3$O$_3$S$_2$, 491.9869). found 491.9855.

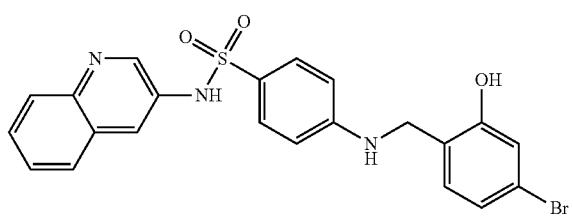 [SMILES: O=S(=O)(Nc1cnc2ccccc2c1)c1ccc(NCc2ccc(Br)cc2O)cc1]

4-(4-bromo-2-hydroxybenzylamino)-N-(quinolin-3-yl)benzenesulfonamide, TFA (80)

Method D: using 3-amino-quinoline and 4-bromo-2-hydroxybenzaldehyde; $^1$H NMR (400 MHz, DMSO-d6) δ 10.41 (d, J=2.1 Hz, 1H), 10.08 (s, 1H), 8.59 (d, J=2.6 Hz, 1H), 7.94-7.83 (m, 3H), 7.61 (tt, J=2.43, and 6.74 Hz, 1H), 7.59-7.41 (m, 3H), 7.01-6.88 (m, 2H), 6.85 (dt, J=2.11, and 8.10 Hz, 1H), 6.53 (dd, J=2.22, and 9.01 Hz, 2H), and 4.10 (s, 2H); LC-MS retention time (Method 1): 2.166 min; HRMS: m/z (M+H)$^+$ (Calculated for C$_{22}$H$_{19}$BrN$_3$O$_3$S, 485.0355). found 485.0331.

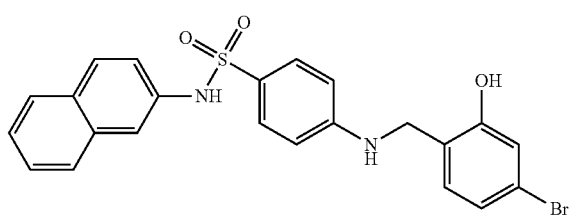 [SMILES: O=S(=O)(Nc1ccc2ccccc2c1)c1ccc(NCc2ccc(Br)cc2O)cc1]

4-(4-bromo-2-hydroxybenzylamino)-N-(naphthalen-2-yl)benzenesulfonamide, TFA (81)

Method D: using 2-amino-naphthalene and 4-bromo-2-hydroxybenzaldehyde; $^1$H NMR (400 MHz, DMSO-d$_6$) δ 10.09 (s, 1H), 10.07 (s, 1H), 7.79-7.66 (m, 3H), 7.51-7.30 (m, 5H), 7.25 (dd, J=2.19, and 8.81 Hz, 1H), 7.00-6.92 (m, 2H), 6.91-6.81 (m, 2H), 6.61-6.25 (m, 2H), and 4.09 (d, J=2.95 Hz, 2H); LC-MS retention time (Method 1): 2.856 min; HRMS: m/z (M+H)$^+$ (Calculated for C$_{23}$H$_{20}$BrN$_2$O$_3$S, 483.0373). found 483.0372.

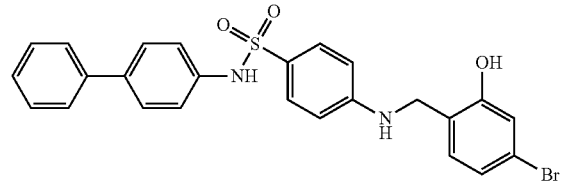 [SMILES: O=S(=O)(Nc1ccc(-c2ccccc2)cc1)c1ccc(NCc2ccc(Br)cc2O)cc1]

N-([1,1'-biphenyl]-4-yl)-4-((4-bromo-2-hydroxybenzyl)amino)benzenesulfonamide, TFA (82)

Method D: using 4-amino-biphenyl and 4-bromo-2-hydroxybenzaldehyde; $^1$H NMR (400 MHz, DMSO-d$_6$) δ 10.03 (s, 1H), 9.37 (s, 1H), 7.61-7.36 (m, 8H), 7.35-7.04 (m, 5H), 6.97 (t, J=5.8 Hz, 1H), 6.78 (t, J=7.8 Hz, 1H), 6.62-6.52 (m, 2H), 4.26 (d, J=5.7 Hz, 2H); LC-MS retention time (Method 2): 6.592 min; HRMS: m/z (M+H)$^+$ (Calculated for C$_{25}$H$_{22}$BrN$_2$O$_3$S, 510.0560). found 510.0549.

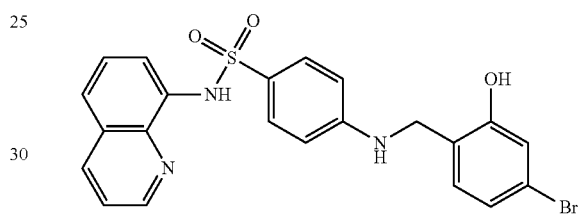

4-(4-bromo-2-hydroxybenzylamino)-N-(quinolin-8-yl)benzenesulfonamide, TFA (83)

Method D: using 8-amino-isoquinoline and 4-bromo-2-hydroxybenzaldehyde; LC-MS retention time (Method 1): 2.524 min; HRMS: m/z (M+H)$^+$ (Calculated for C$_{22}$H$_{19}$BrN$_3$O$_3$S, 485.0355). found 485.0345.

Systematic Structure-Activity Relationship (SAR) explorations as shown in Tables 1-3 were conducted. As shown in Table 1, the removal of the phenolic groups (8), 3-OMe group (9), or the 2-OH group (10) resulted in a complete loss of activity. Protecting the 2-OH moiety as methyl ether (compounds 11-12) or replacing with an amine (compounds 13 and 15) also negated all 12-LOX inhibitory activity. A bioisosteric replacement of the catechol moiety with an indole (17) was also inactive. The 2,3-dichloro derivative (18) had comparable activity to compound 1. Also, the 3-Cl (19, IC$_{50}$=6.1 μM) had comparable activity while the 3-Fluoro and 3-Bromo (20, IC$_{50}$=19 μM and 21, IC$_{50}$=13 μM) was ~4 to ~2.5-fold fold less active, respectively. An interesting and unexpected result was the 2-fold improvement in activity observed for the 4-bromo (22, IC$_{50}$=2.2 μM) and 4-chloro (27) derivatives. Other 4-substituted derivatives such as 4-methoxy (28) had reduced activity compared to compound 1. The 2-OH was important for activity and the 3-position is most optimal for the methoxy group. This preliminary SAR suggested that the 3-OMe could be replaced with a chloro group (19) and the 4-Bromo (22) while maintaining comparable, if not improved activity to compound 1.

TABLE 1

12-LOX Inhibition of Analogues 1, 8-34[a]

[Structures shown: compounds 1, 8-12 feature a thiazole-NH-SO2-phenyl-NH-CH2-R scaffold; compounds 13-34 feature a thiazole-NH-SO2-phenyl-NH-CH2-(2-hydroxyphenyl with R substituent) scaffold]

| compd | R | $IC_{50}$ [± SD] (μM) |
|---|---|---|
| 1 | 2-OH, 3-OMe—Ph | 5.1 [0.5] |
| 8 | Ph | >40 |
| 9 | 2-OH—Ph | >40 |
| 10 | 3-OMe—Ph | >40 |
| 11 | 2-OMe—Ph | >40 |
| 12 | 2,3-OMe—Ph | >40 |
| 13 | 2-$NH_2$—Ph | >40 |
| 14 | 3-OH—Ph | >40 |
| 15 | 2-$NH_2$, 3-OMe—Ph | >40 |
| 16 | 3-OH, 4-OMe—Ph | >40 |
| 17 | 7-indole | >40 |
| 18 | 2,3-Cl—Ph | >40 |
| 19 | 3-Cl | 6.2 [2.0] |
| 20 | 3-F | 19 [4] |
| 21 | 3-Br | 13 [1] |
| 22 | 4-Br | 2.2 [0.5] |
| 23 | 3-Me | >40 |
| 24 | 3-$NH_2$ | >40 |
| 25 | 3-$NO_2$ | >40 |
| 26 | 3-allyl | >40 |
| 27 | 4-Cl | 6.3 [1.0] |
| 28 | 4-OMe | 22 [11] |
| 29 | 5—Cl | >40 |
| 30 | 5—OMe | >40 |
| 31 | 5-$NH_2$ | >40 |
| 32 | 5-F | >40 |
| 33 | 5-$NO_2$ | >40 |
| 34 | 6-OMe | >40 |

[a]$IC_{50}$ values represent the half maximal (50%) inhibitory concentration as determined in the UV-vis cuvette-based assay in triplicate.

The next SAR profile focused on modification of the thiazole group as shown in Table 2. Changes to this region of the molecule led to analogs with improved potency. Replacing the thiazole moiety with a 2-benzothiazole (35, ML355) resulted in an 18-fold improvement in 12-LOX activity while retaining selectivity. The benzoxazole (36) and benzimidazole (37) possessed good to excellent activity, and introduction of a methyl group at the 4-position of the benzothiazole ring (39), maintained excellent 12-LOX activity ($IC_{50}$=0.24 μM). Potency against 12-LOX was also improved over 10-fold when the thiazole was replaced with a thiophene (38), but the substituted thiazole/isoxazole derivatives (40-43) did not show this increased potency. This was also the case with the phenyl derivative (48), a known thiophene bioisostere, which had potent activity against 12-LOX ($IC_{50}$=0.5 μM). Generally, larger aromatic [1-naphthalene (49) and 2-naphthalene (50)] and heteroaromatic compounds [3-quinoline (46), 8-isoquinoline (47), 2-pyridine (58) and 3-pyridine (59)] were well tolerated and had better potency than the thiazole derivative (1). In an effort to improve solubility by adding solubilizing functionality, a few phenyl derivatives substituted with a piperazine moiety at different positions around the aryl ring were synthesized (53-55). While these changes were tolerated, they had reduced activity compared to the top actives (e.g. entry 35, ML355).

Many of these analogs were also tested for activity against 15-LOX-1 to ensure that selectivity was maintained. These compounds were initially tested against 15-LOX-1 at a single concentration (25 μM) and an $IC_{50}$ was determined only on compounds of interest. These studies showed that replacement of the thiazole with a benzothiazole, and its derivatives maintained selectivity with 15/12-LOX ratios of 29-fold (35), 18-(39), 19-(62) and 20-(68). The 15-LOX/12-LOX selectivity ratio improved to over 100 with conversion of the benzothiazole to a benzoxazole (36), benzimidazole (37) and m-iPr substituted phenyl (67). The phenyl substitution (48) only had a selectivity ratio of 15. A wide-range of selectivity was observed despite the compounds bearing comparable structures, ranging from almost complete inhibition of 15-LOX-1 (e.g. 38 and 62) to minimal inhibition (e.g. 55, 58, and 66). The dramatic effect on selectivity between 12-LOX and 15-LOX-1 in this portion of the molecule, suggests that the bottom of the LOX active site is involved in binding, since it has been shown to control substrate specificity previously.

TABLE 2

12-LOX Inhibition of Analogues 35-68[a]

[Structure: sulfonamide-linked aniline with CH2-NH connected to 2-OH-3-OMe-phenyl, with R group]

| compd | R | 12-LOX IC50[+SD] (μM) | 15-LOX-1 IC50[+SD] (μM) | % inh[b] |
|---|---|---|---|---|
| 35 | 2-benzothiazole | 0.34 [0.04] | 9.7 [0.1] | |
| 36 | 2-benzoxazole | 0.79 [0.1] | >100 | |
| 37 | 2-benzimidazole | 0.57 [0.04] | >70 | |
| 38 | 2-thiophene | 0.35 [0.02] | | 100 |
| 39 | 4-Me-2-benzothiazole | 0.24 [0.01] | 0.69 [0.1] | |
| 40 | 4-Me-2-thiazole | 2.7 [0.2] | | 14 |
| 41 | 5-Me-2-thiazole | 3.0 [0.4] | | 75 |
| 42 | 5-Ph-2-thiazole | 91% b | | 77 |
| 43 | 4,5-Me-2-thiazole | 1.4 [0.3] | | 37 |
| 44 | 5-Me-3-isoxazole | 11 [1.2] | | |
| 45 | 3-OMe—Ph | 85% b | | 73 |
| 46 | 3-quinoline | 0.48 [0.1] | | 77 |
| 47 | 8-isoquinoline | 0.70 [0.2] | | 70 |
| 48 | Ph | 0.50 [0.05] | 7.6 [1.0] | |
| 49 | 1-naphthalene | 0.51 [0.06] | | 73 |
| 50 | 2-naphthalene | 0.33 [0.05] | | 54 |
| 51 | 1,4-bi-Ph | 1.3 [0.2] | | 60 |
| 52 | 1,3-bi-Ph | 82% b | | 70 |
| 53 | 3-piperazine-Ph | 3.5 [0.5] | | 31 |
| 54 | 4-piperazine-Ph | 11 [2.7] | | |
| 55 | 4-piperidine-Ph | 3.7 [0.6] | | 8 |
| 56 | 4-piperazine-3-pyr | 4.0 [0.6] | | 12 |
| 57 | 6-methyl-3-pyr | 5.0 [0.5] | | 18 |
| 58 | 2-pyr | 5.0 [0.5] | | 3 |
| 59 | 3-pyr | 7.0 [0.5] | | |
| 60 | 2-pyrimidine | 12 [1.0] | | |
| 61 | 3-tBu-Ph | 0.39 [0.8] | | 66 |
| 62 | 6-OMe-2-benzothiazole | 0.26 [0.3] | 5.1 [0.6] | |
| 63 | 4-Ph-2-thiazole | 0.18 [0.03] | | 87 |
| 64 | 3-morpholine-Ph | 3.8 [0.3] | | 50 |
| 65 | 4N-boc-piperidine-3-Ph | 0.76 [0.05] | | 34 |
| 66 | 3-piperidine-Ph | 1.1 [0.3] | | 4.7 |
| 67 | 3-iPr-Ph | 0.16 [0.02] | >100 | |
| 68 | 6-F-2-benzothiazole | 0.22 [0.05) | 4.5 [0.4] | |

[a]IC50 values represent the half maximal (50%) inhibitory concentration as determined in the UV-vis cuvette-based assay in triplicate.
[b]Represents inhibition at 25 μM.

As noted above (Table 1), replacement of the "right-hand" portion of the molecule with a 3-chloro-2-phenol (19) or 4-bromo-2-phenol (22) resulted in comparable potency to 1 with IC$_{50}$ values of 6.2 and 2.2 μM respectively. These groups were combined with some of the sulfonamide derivatives discovered as part of the initial SAR efforts (see Table 3, compounds 69-83). None of the compounds had improved potency and in almost all cases, had reduced activity. Generally, the 2-benzothiazole moiety gave the best activity with both the 3-Chloro-2-phenol (71; IC$_{50}$=1.6 μM) and 4-bromo-2-phenol (79; IC$_{50}$=1.7 μM), although the 1-naphthalene derivative 78 had comparable potency (IC$_{50}$=1.3 μM).

TABLE 3

12-LOX Inhibition of Analogues 69-83[a]

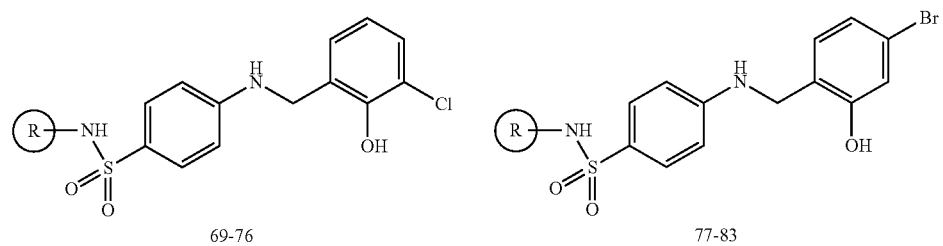

69-76 (3-Cl-2-OH phenyl); 77-83 (4-Br-2-OH phenyl)

| compd | R | 12-LOX IC50[+SD] (μM) | 15-LOX-1 IC50[+SD] (μM) | % inh[b] |
|---|---|---|---|---|
| 69 | Ph | 4.5 [0.4] | | 49 |
| 70 | 1-naphthalene | 1.6 [0.2] | | 70 |
| 71 | 2-benzothiazole | 1.3 [0.2] | 1.3 [0.2] | |
| 72 | 2-naphthalene | 2.3 [0.3] | | 75 |
| 73 | 4-bi-Ph | 4.2 [1.0] | | 73 |
| 74 | 8-isoquinoline | 4.5 [0.8] | | 63 |
| 75 | 3-quinoline | 5.3 [0.7] | | 58 |
| 76 | 4-piperidine-Ph | 6.3 [3.0] | | 4 |
| 77 | Ph | 2.9 [0.4] | | 82 |
| 78 | 1-naphthalene | 1.3 [0.3] | | 83 |
| 79 | 2-benzothiazole | 1.7 [0.8] | | 100 |

TABLE 3-continued

12-LOX Inhibition of Analogues 69-83[a]

Structures:
- 69-76: R–NH–SO₂–(phenyl)–NH–CH₂–(phenyl with Cl and OH)
- 77-83: R–NH–SO₂–(phenyl)–NH–CH₂–(phenyl with Br and OH)

| compd | R | 12−LOX IC50[+SD] ($\mu M$) | 15−LOX−1 IC50[+SD] ($\mu M$) | % inh[b] |
|---|---|---|---|---|
| 80 | 3-quinoline | 2.3 [0.5] | | 74 |
| 81 | 2-naphthalene | 2.2 [0.3] | | 78 |
| 82 | 4-bi-Ph | 2.5 [0.4] | | 80 |
| 83 | 8-quinoline | 5.6 [2.0] | | 55 |

[a]IC$_{50}$ values represent the half maximal (50%) inhibitory concentration as determined in the UV-vis cuvette-based assay in triplicate.
[b]Represents inhibition at 25 $\mu M$.

Further studies focusing on the selectivity of analogs (35, 36, and 37) against other human LOX isozymes (5-LOX and 15-LOX-2) were conducted. In addition, the compounds were tested against cyclooxygenase-1 (COX-1) and/or COX-2. As shown in Table 4, there was no significant inhibition against any of these related enzymes, with exception to ML355 which has modest potency (29-fold less active) towards 15-LOX-1. Few compounds reported in the literature have achieved both nM potency towards 12-LOX and selectivity against other isozymes.

TABLE 4

Selectivity and Redox Activity of Representative Analogues[a]

| analogue | 12-LOX[b] | 15-LOX-1[b] | 15-LOX-2[b] | 5-LOX[b] | COX-1/-2[c] | redox activity[d] |
|---|---|---|---|---|---|---|
| 1 | 5.1 | >50 | >40 | >200 | NT | NT |
| 35 | 0.34 | 9.7 | >100 | >100 | NI | NI |
| 36 | 0.79 | >100 | >100 | >100 | NI | NI |
| 37 | 0.57 | >100 | >100 | >35 | NI | NT |

[a]Selectivity profiling of 1, 35, 36, and 37.
[b]IC$_{50}$ values are reported in $\mu M$.
[c]Compounds were tested at 15 $\mu M$ and none of the compound exhibited inhibition above 10%.
[d]UV - vis pseudoperoxidase activity assay was performed on 35 and 36, and no degradation of the hydroperoxide product was observed at 234 nm, indicating a nonreductive inhibitory mechanism; NI = no inhibition and NT = not tested.

Figure 4:
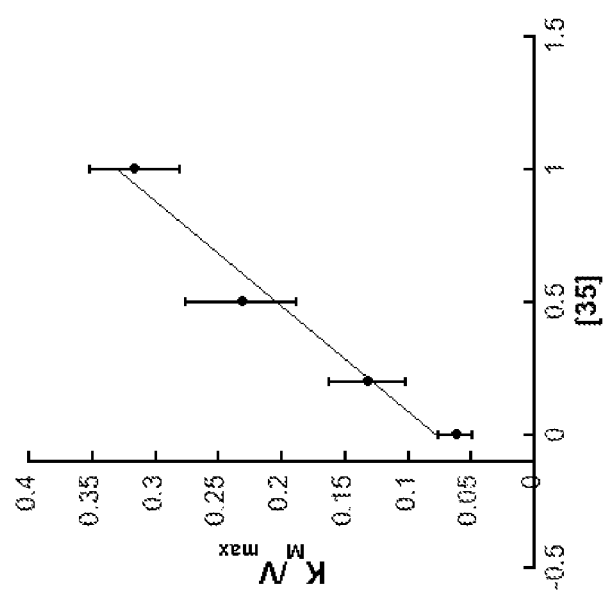
FIG. 4. Steady-state kinetics data for the determination of $K_i$ for 12-LOX with compound 35 (ML355). $K_M/V_{max}$ (x-intercept, $K_M/V_{max}$ units are µM/µmol/min/mg) versus [Inhibitor] (µM) is the secondary replot of the inhibition data, which yielded a $K_i$ of 0.35+/−0.08 µM.
Figure 5:
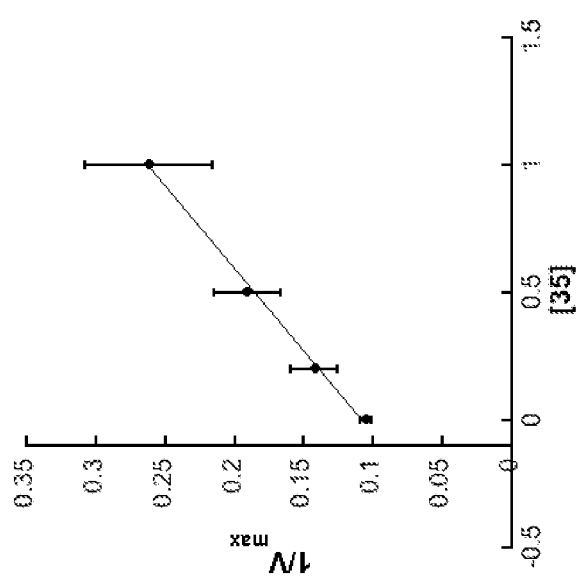
FIG. 5. Steady-state kinetics data for the determination of $K_i'$ for 12-LOX with compound 35 (ML355). $1/V_{max}$ (y-intercept, $1/V_{max}$ units are 1/µmol/min/mg) versus [Inhibitor] (µM) is the secondary replot of the inhibition data, which yielded a $K_i$ of 0.72+/−0.1 µM.
Figure 6:
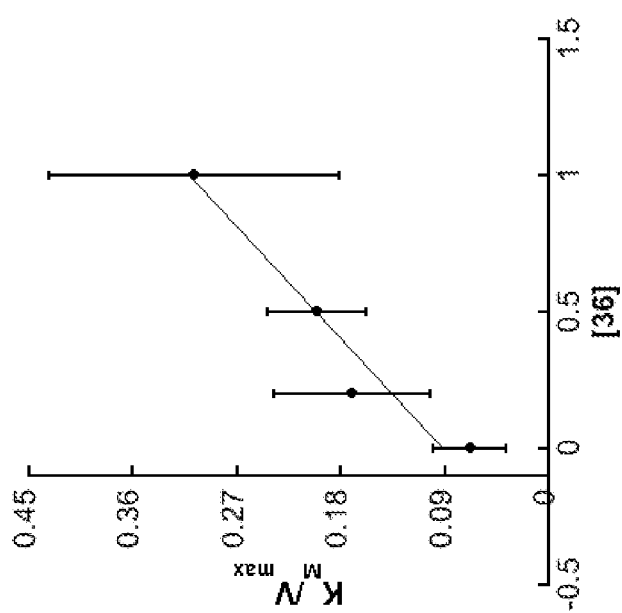
FIG. 6. Steady-state kinetics data for the determination of $K_i$ for 12-LOX with compound 36. $K_M/V_{max}$ (x-intercept, $K_M/V_{max}$ units are µM/µmol/min/mg) versus [Inhibitor] (µM) is the secondary replot of the inhibition data, which yielded a $K_i$ of 0.53+/−0.2 µM.
Figure 7:
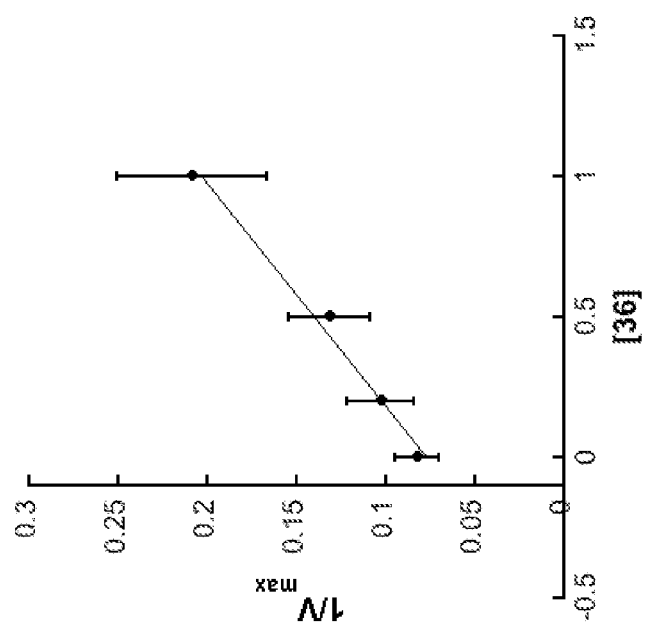
FIG. 7. Steady-state kinetics data for the determination of $K_i'$ for 12-LOX with compound 36. $1/V_{max}$ (y-intercept, $1/V_{max}$ units are 1/µmol/min/mg) versus [Inhibitor] (µM) is the secondary replot of the inhibition data, which yielded a $K_i$ of 0.63+/−0.1 µM.

LOX inhibitors are known to exhibit a variety of inhibitory mechanisms; therefore the UV pseudoperoxidase assay is used to investigate if the inhibition is reductive in nature. The assay was performed on 35 and 36 with 12-LOX and no degradation of the hydroperoxide product was observed at 234 nm, indicating a nonreductive inhibitory mechanism (Table 4). To investigate the inhibition mechanism further, steady-state kinetics were performed using both 35 and 36 by monitoring the formation of 12-HPETE as a function of substrate and inhibitor concentration in the presence of 0.01% Triton X-100. Replots of $K_m/V_{max}$ and $1/V_{max}$ versus inhibitor concentration yielded linear trends for both 35 and 36. The $K_i$ equaled 0.35±0.08 $\mu M$ for 35 and 0.53±0.2 $\mu M$ for 36, from the $K_m/V_{max}$ graphs (FIGS. 4 and 6). The $K_{i'}$ equaled 0.72±0.1 $\mu M$ for 35 and 0.62±0.1 $\mu M$ for 36, from the $1/V_{max}$ graphs (FIGS. 5 and 7). The data for both 35 and 36 correlate with their IC50 values (Table 2) and indicate that both molecules are mixed inhibitors, which is a common property of both 12-LOX and 15-LOX-1 inhibitors in general.

Figures 2A, 2B:
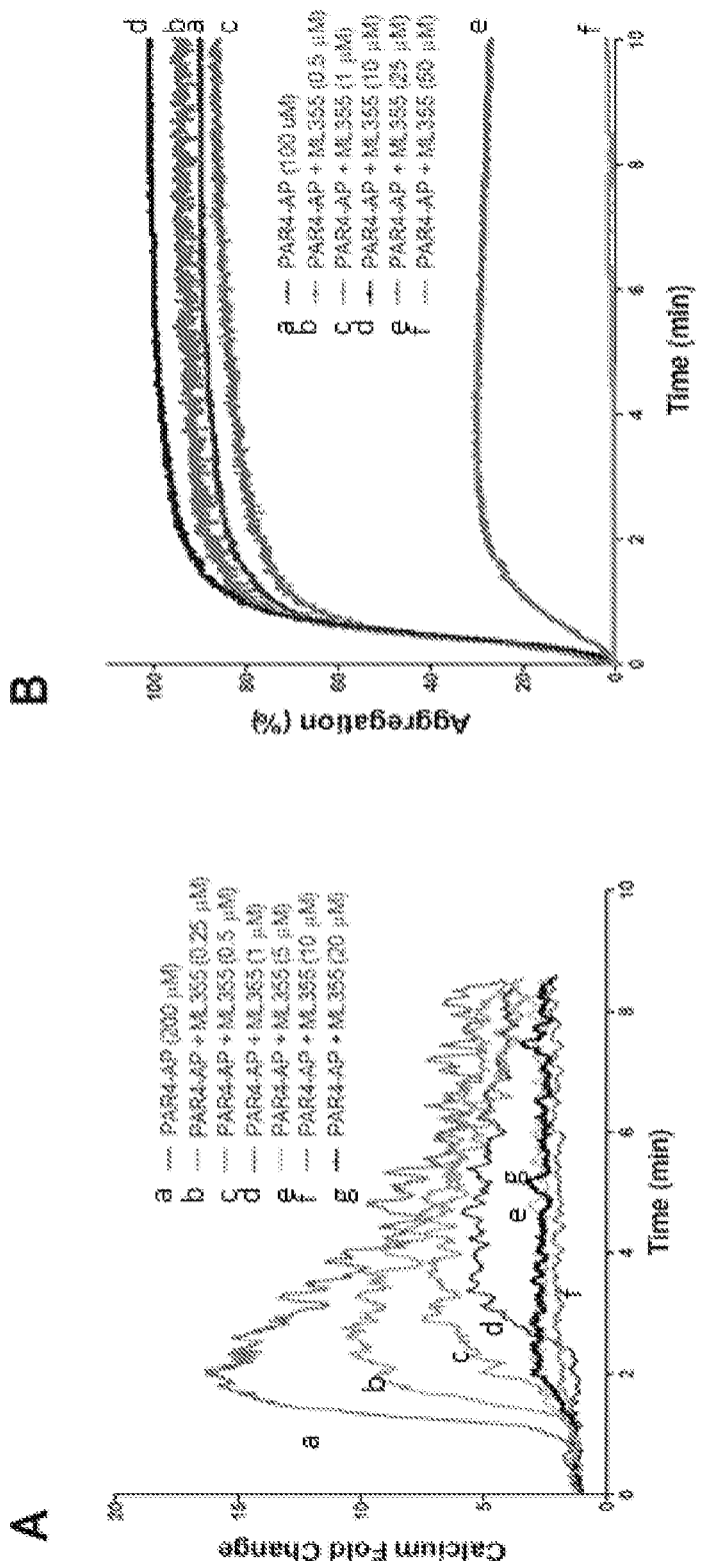
FIG. 2. PAR4-AP-induced calcium mobilization (A) and platelet aggregation (B) in human platelets.
Figure 8:
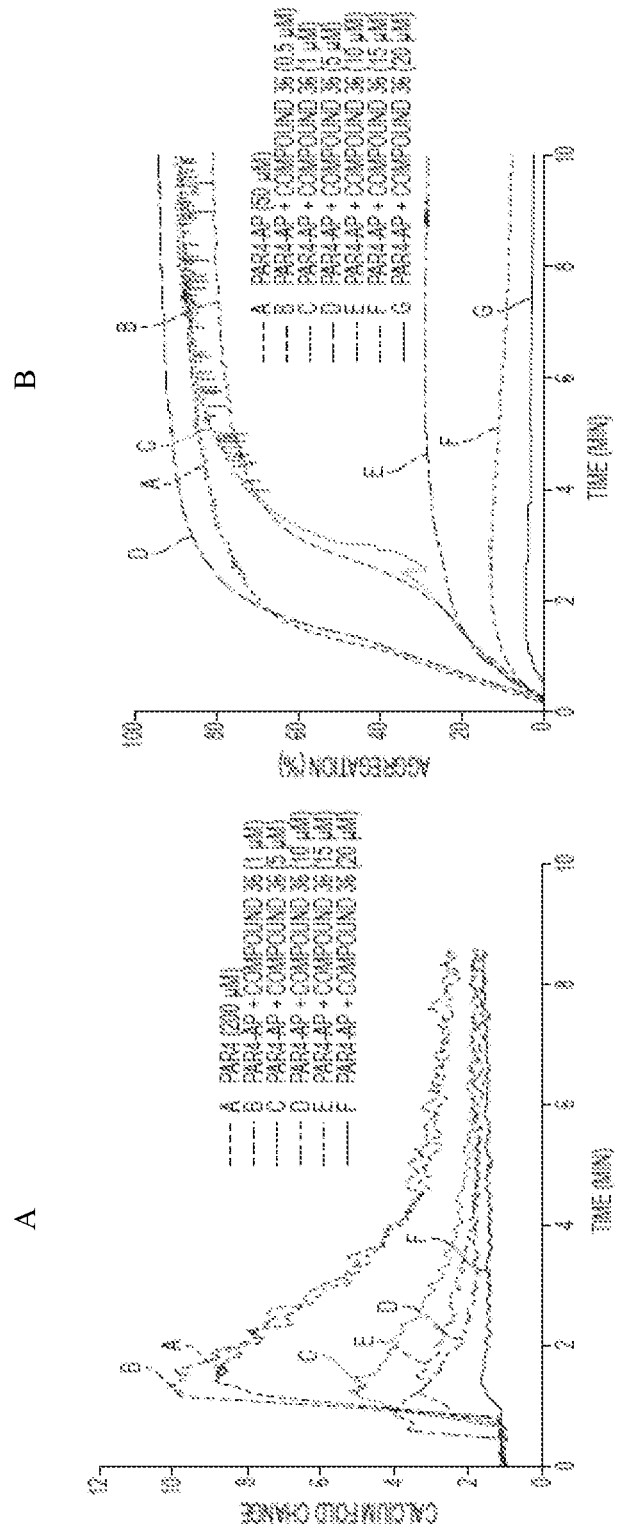
FIG. 8. PAR4-AP-induced calcium mobilization (A) and platelet aggregation (B) in human platelets. For A: Washed human platelets (1×10⁶ platelets/mL) were stimulated with 200 µM PAR4-AP in the absence or presence of increasing concentrations of compound 36. Calcium mobilization was decreased as the concentration of compound 36 was increased. Calcium was measured in real time using a C6 Accuri flow cytometer. The experiments were done in triplicate. For B: Platelet aggregation of human platelets (3×10⁸ platelets/mL) was measured in real-time using a Chronolog Lumi-Aggregometer (model 700D) following addition of PAR4-AP.

The activity of ML355 in relevant cell-based systems was explored. As noted previously, 12-LOX has been linked to platelet activation, which plays a central role in the regulation of primary hemostasis and arterial thrombosis. Consequently, failure to attenuate platelet activation results in excessive clot formation leading to adverse cardiovascular events such as myocardial infarction and stroke. Previous studies have shown that 12-LOX in human platelets is highly activated following stimulation of the protease-activated receptor-4 (PAR4) by the PAR4-activating peptide (PAR4-AP). Moreover, the bioactive metabolite of 12-LOX (12-HETE), resulting from the stereospecific oxidation of arachidonic acid (AA) and reduction by peroxidases, demonstrates pro-thrombotic effects in human platelets. Therefore, treatment of PAR4-AP-induced human platelets with a small molecule 12-LOX inhibitor attenuates the platelet aggregation in a dose dependent manner. To confirm this, washed human platelets (1×10⁶ platelets/ml) were stimulated with 200 $\mu M$ PAR4-AP in the absence or presence of increasing concentrations of ML355 (FIG. 2A). Calcium mobilization was decreased as the concentration of ML355 was increased. Calcium was measured in real time using a C6 Accuri flow cytometer. The experiments were done in triplicate. In addition, platelet aggregation of human platelets ($3 \times 10^8$ platelets/ml) was measured in real-time using a Chronolog Lumi-Aggregometer (model 700D) following addition of PAR4-AP (FIG. 2B). While 10 μM ML355 did not inhibit platelet aggregation, 25 μM ML355 inhibited 80% platelet aggregation in washed human platelets. The results in FIG. 2B show that ML355 does in fact significantly reduce PAR4-AP induced platelet aggregation. Further, 12-LOX has been shown to play a role in calcium mobilization in human platelets and inhibition of 12-LOX leads to a reduced concentration of free calcium in the platelet. To study this, human platelets were stimulated with 200 μM PAR4-AP and the free calcium in the platelet was measured, using a C6 Accuri flow cytometer with various concentrations of ML355 (FIG. 2A). These data demonstrate that at concentrations as low as 250 nM of ML355 calcium mobilization is reduced significantly (measured as fold change), with complete inhibition of calcium mobilization occurring at ~5 μM. Comparable results were obtained with another top active (compound 36) shown in FIG. 8.

Figures 3A, 3B, 3C, 3D, 3E:
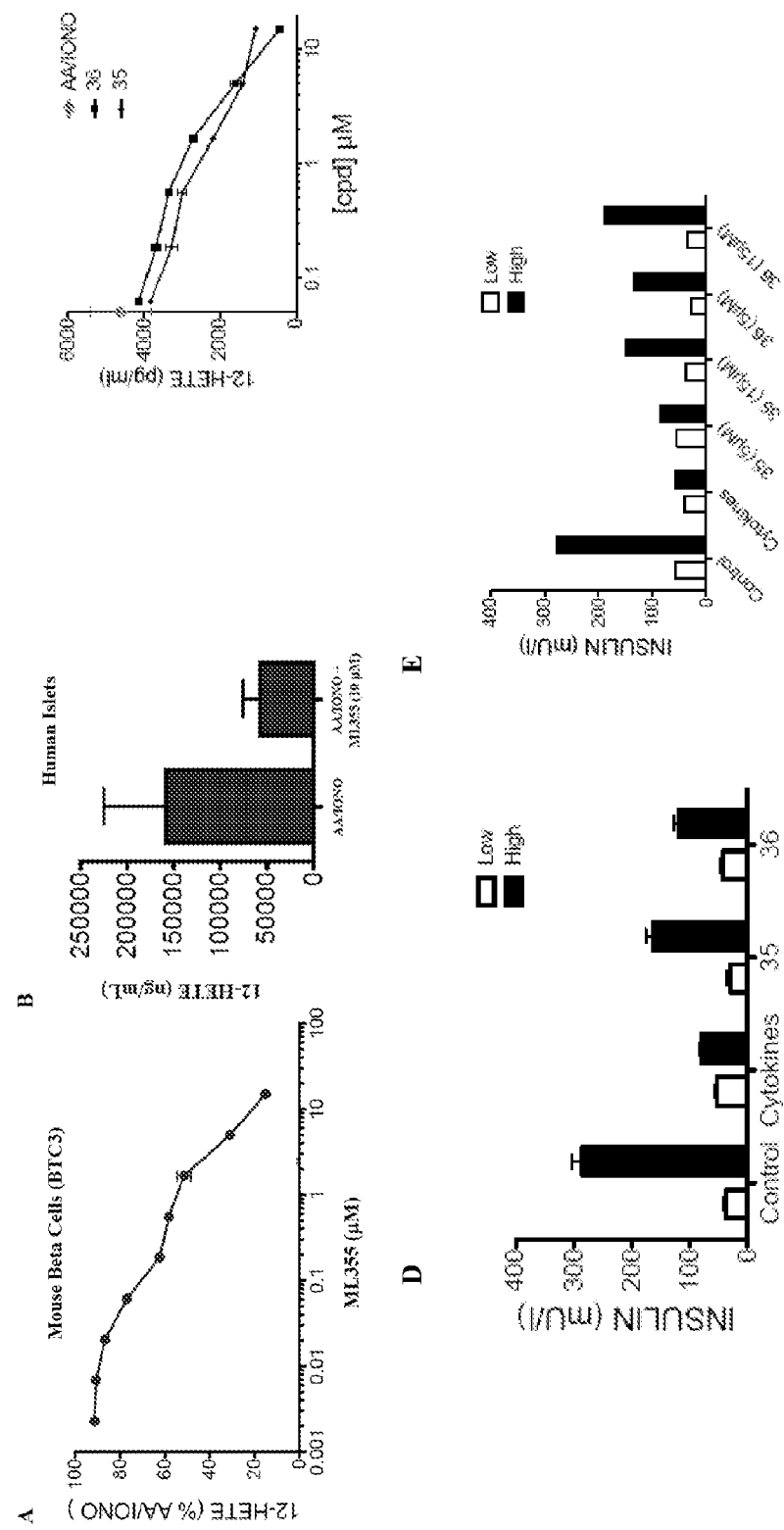
FIG. 3. Inhibition of 12-HETE in mouse beta cells (A) and human islets (B, C). Glucose-stimulated insulin secretion in human islets (D, E).
Figure 9:
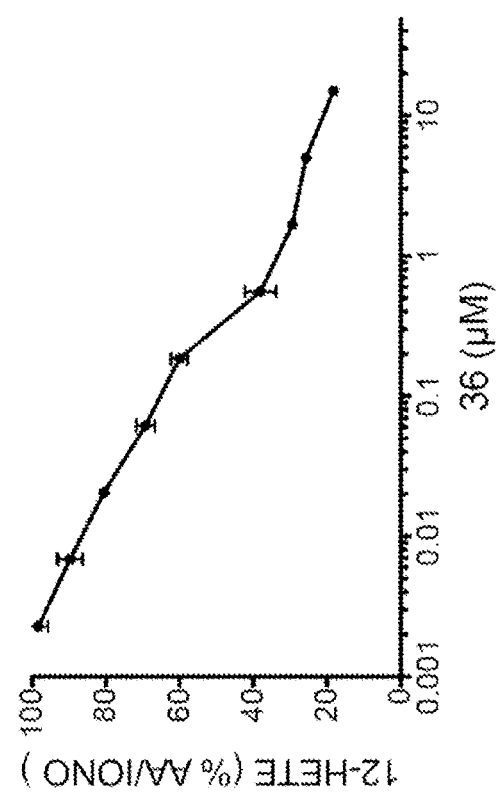
FIG. 9. Inhibition of 12-HETE by compound 36 in mouse beta cells. Mouse beta cells (BTC3) were treated with arachidonic acid and calcium ionophore (AA/IONO) alone or in the presence of compound 36. Graphed are the levels of 12-HETE expressed as a percentage of that detected in cells stimulated with AA/IONO alone. The data graphed in FIG. 3A is a representative experiment with each plotted data point being performed in triplicate. These plotted data are representative of four separate experimental determinations performed covering a lesser dose range. The graphed data are mean±SEM, n=3. Error bars for some points are masked by the symbol. The data was analyzed by non-linear regression for dose-response curve inhibition, using variable or restricted hill slope, $R^2$>0.81. This analysis was facilitated with Prism 5 software. In addition to compound, DMSO (stock solvent) was included with each condition. DMSO is also the solvent for the calcium ionophore (stimulant).

The ability of ML355 to inhibit 12-LOX in cell-based models relevant for diabetic disease was also assessed. As discussed above, 12-LOX is expressed in pancreatic β cells and its metabolic product, 12-HETE, is implicated in cytokine-induced cell death. Specifically, 12(S)-HETE has been shown to reduce metabolic activity inhibit insulin secretion and ultimately induce cell death in human islets. ML355 was tested in both a mouse derived β-cell line (BTC3) and human primary donor islets to determine its ability to inhibit AA/calcium ionophore induced stimulation of 12-HETE. ML355 was able to potently inhibit 12-HETE in BTC3 cells with an approximate $IC_{50}$ of 1 μM, as measured by ELISA (FIG. 3A). Given the difficulty in obtaining primary human islets from donated tissues, the activity in human islets was performed at a single concentration. The data presented in FIG. 3B demonstrates significant inhibition of AA/IONO-induced 12-HETE production, at 10 μM of ML355. Comparable results were obtained with another top active (compound 36) shown in FIG. 9.

Mouse beta cells (BTC3) were treated with arachidonic acid and calcium ionophore (AA/IONO) alone or in the presence of ML355 (FIG. 3A). Graphed are the levels of 12-HETE expressed as a percentage of that detected in cells stimulated with AA/IONO alone. In FIG. 3B the graph represents the increase (above control/unstimulated) in 12-HETE for human primary donor islets stimulated with arachidonic acid and calcium ionophore (AA/IONO) alone or in the presence of 10 μM of ML355. 12-HETE was measured by ELISA. In FIG. 3C the graph represents the levels of 12-HETE detected when human donor islets were treated with arachidonic acid and calcium ionophore (AA/IONO) alone or in the presence of different concentrations of compound 35 or 36. The data graphed in FIG. 3C is a representative experiment with each plotted data point being performed in triplicate. These plotted data are representative of three separate experimental determinations each performed on separate human donor islet preparations. The graphed data are mean±SEM, n=3. Error bars for some points are masked by the symbol.

FIGS. 3D and 3E show results from glucose-stimulated insulin secretion in human donor islet preparations in response to 3 mM glucose (Low) or 18 mM glucose (High) for control (untreated) islets. The islets were incubated with Cytokines (TNFα, IL-1β, IFNγ) and islets co-incubated with cytokines and compounds 35 or 36. FIGS. 3D and 3E represent results obtained in different human donor islet preparations. Uncoupling of glucose-stimulated insulin secretion by cytokines is inhibited by compounds 35 or 36.

While the above data demonstrates activity in disease relevant cell-based models, in order to validate the potential use of ML355 in proof of concept animal models, both its in vitro ADME and in vivo PK properties were determined. These data are summarized in Tables 5 and 6 respectively. ML355 demonstrated excellent microsomal stability with both rat ($T_{1/2}$>30 minutes) and mouse ($T_{1/2}$>300 minutes) and was found to be stable to mouse plasma over a 2 hour period (100% remaining) Moreover, ML355 showed no degradation over various aqueous buffers (pH 2-9) and was stable to 5 mM glutathione suggesting excellent stability (Supplemental Figure S5). Improved solubility is observed in assay buffer (qualitative analysis). In addition the benzoxazole derivative (36) has much improved solubility in buffer (>10-fold) albeit with slightly weaker potency towards 12-LOX.

TABLE 5

In Vitro ADME Profile for 35

| compd | PBS buffer (pH 7.4) solubility (μg/mL) | Microsomal stability $T_{1/2}$ (min)[a,b] | Microsomal stability $T_{1/2}$ (min)[a,b] | permeability ($1 \times 10^{-6}$ cm/s) | efflux ratio | mouse plasma stability remaining at 2 h (%) | PBS buffer (pH 7.4) stability at 48 h (%) |
|---|---|---|---|---|---|---|---|
| 35 | <5 | >30 (rat) | >300[a] (mouse) | 1.5 (A→B)[a] 394[c] | 1.8 | 100 | 100 |
| 36 | >60 | >30 (rat) | NT | 168[c] | NT | 100 | 100 |

[a] These experiments were conducted at Pharmaron Inc. All other studies were conducted at NCATS.

[b] Represents the stability in the presence of NADPH. 35 and 36 showed no degradation without NADPH present over a 1 h period.

[c] Represents permeability in the Parallel Artificial Membrane Permeability Assay (PAMPA) at pH 7.4.

TABLE 6

In Vivo PK (Mouse) at 3 mpk (IV) and 30 mpk PO for 35[a]

| compd | route[b] | $T_{1/2}$ (h) | $T_{max}$ (h) | $C_{max}$ (µM) | $AUC_{inf}$ (µM · h) | $V_d$ (L/kg) | Cl (mL/min/kg) | % F | MRT[c] |
|---|---|---|---|---|---|---|---|---|---|
| 35 | IV | 3.4 | NA | 112 | 34 | 0.55 | 3.4 | NA | 2.44 h |
|    | PO | 2.9 | 0.25 | 38 | 67 | NA | NA | 19.8 | NA |

[a]All experiments were conducted at Pharmaron Inc. using male CD1 mice (6-8 weeks of age). Data was collected in triplicate at 8 time points over a 24 h period.
[b]Formulated as a solution (5% DMSO, 10% Solutol, 20% PEG400, 65% water).
[c]Represents the time for elimination of 63.2% of the IV dose.

ML355 showed moderate cell permeability in the Caco-2 assay ($1.5 \times 10^{-6}$ cm/s) and does not appear to be a substrate for Pgp given the efflux ratio of <2. The in vivo PK (mouse) properties of the molecule were also explored (Table 6). Exploratory formulation studies led to an appropriate vehicle (DMSO:Solutol:PEG400:water; 5/10/20/65 v/v/v/v) in which ML355 was administered as a solution via IV (3 mpk) and PO (30 mpk). These studies demonstrate that ML355 is orally bioavailable (% F=~20), with a moderate half-life ($T_{1/2}$=2.9 hours). At 30 mpk dosing, ML355 achieves a $C_{max}$ of over 135 times the in vitro $IC_{50}$ and remains over $IC_{50}$ value for over 12 hours. The compound has low clearance (3.4 mL/min/kg) and good overall exposure ($AUC_{inf}$) of 38 µM. The volume of distribution ($V_d$) is 0.55 L/kg, which is low but suggests a reasonable distribution between tissue and blood. Given the favorable microsomal stability (phase I metabolism) yet modest in vivo $T_{1/2}$ it was believed that the phenolic moiety could be glucuronidated (phase II metabolism) leading to higher clearance than anticipated. In fact, incubation with UDPGA co-factor instead of NADPH led to a $T_{1/2}$ of ~8 minutes (vs. >30 minutes with NADPH). It was further believed that the sterically hindered environment of the 2-OH would possibly prevent glucuronidation from occurring, yet this data suggests otherwise. Another strategy which has been used to obviate a glucuronidation is to introduce electron-withdrawing groups next to the phenolic moiety of interest. Using this strategy analog 71 (2-OH, 3-Cl) was synthesized, however, this did not change the rate of glucuronidation. In addition to introducing other electron-withdrawing groups to the ring, another approach is to modify the phenolic hydroxyl using a pro-drug approach. Ideally, the pro-drug would be slowly hydrolyzed to the free phenol, after it has bypassed first-pass metabolism. This approach has been used successfully in several marketed drugs, which contain phenolic groups. (Ettmayer, P.; Amidon, G. L.; Clement B.; Testa, B. Lessons learned from marketed and investigational prodrugs. *J. Med. Chem.* 2004, 47, 2393-2404.)

As stated above, previously reported inhibitors of 12-LOX, such as baicalein and nor-dihydroguaiaretic acid (NDGA), "bromo-phenols" or "pyrazole derivatives" (see FIG. 1) are not only less potent and selective, but are also not easily amendable to further optimization. Our previously described 12-LOX inhibitor (ML127) does demonstrate potent inhibition (<500 nM) and excellent selectivity, but was found to exhibit tight flat SAR thus providing little opportunity for further modification. A structurally distinct, new chemotype that is different from all previously reported inhibitors, and possesses a drug-like scaffold was discovered. ML355, and related top analogs demonstrate potent (<500 nM) inhibition towards 12-LOX and excellent selectivity against related enzymes (15-LOX-1, 5-LOX, 15-LOX-2, COX 1/2). This series is readily amendable to structural modifications and displays clear and tractable SAR. ML355 exhibits a favorable in vitro ADME and in vivo PK profile with activity in disease relevant cell-based systems, such thrombosis (platelet aggregation and calcium mobilization) and diabetes (12-HETE reducing in β-cells).

Biological Reagents: All commercial fatty acids (Sigma-Aldrich Chemical Company) were re-purified using a Higgins HAIsil Semi-Preparative (5 µm, 250×10 mm) C-18 column. Solution A was 99.9% MeOH and 0.1% acetic acid; solution B was 99.9% $H_2O$ and 0.1% acetic acid. An isocratic elution of 85% A:15% B was used to purify all fatty acids, which were stored at −80° C. for a maximum of 6 months.

Human Platelets: Human platelets were obtained from healthy volunteers within the Thomas Jefferson University community and the Philadelphia area. These studies were approved by the Thomas Jefferson University Institutional Review Board, and informed consent was obtained from all donors before blood draw. Blood was centrifuged at 200 g for 13 min at room temperature. Platelet-rich plasma was transferred into a conical tube containing a 10% acid citrate dextrose solution (39 mM citric acid, 75 mM sodium citrate, and 135 mM glucose, pH 7.4) and centrifuged at 2000 g for 15 min at room temperature. Platelets were resuspended in Tyrode's buffer (12 mM $NaHCO_3$, 127 mM NaCl, 5 mM KCl, 0.5 mM $NaH_2PO_4$, 1 mM $MgCl_2$, 5 mM glucose, and 10 mM HEPES), and the final platelet concentration was adjusted to $3 \times 10^8$ platelets/mL after counting with a ZI Coulter particle counter (Beckman Coulter, Fullerton, Calif.). Reported results are the data obtained using platelets from at least three different subjects. Agonists and inhibitors were used at concentrations indicated in the figures and figure legends.

Over Expression and Purification of 12-Human Lipoxygenase, 5-Human Lipoxygenase, 12/15-Mouse Lipoxygenase and the 15-Human Lipoxygenases: Human platelet 12-lipoxygenase (12-LOX), human reticulocyte 15-lipoxygenase-1 (15-LOX-1), and human epithelial 15-lipoxygenase-2 (15-LOX-2), were expressed as N-terminally, $His_6$-tagged proteins and purified to greater than 90% purity, as evaluated by SDS-PAGE analysis. Human 5-lipoxygenase was expressed as a non-tagged protein and used as a crude ammonium sulfate protein fraction, as published previously. Iron content of 12-LOX was determined with a Finnigan inductively coupled plasma mass spectrometer (ICP-MS), using cobalt-EDTA as an internal standard. Iron concentrations were compared to standardized iron solutions and used to normalize enzyme concentrations.

High-Throughput Screen Materials: Dimethyl sulfoxide (DMSO) ACS grade was from Fisher, while ferrous ammonium sulfate, Xylenol Orange (XO), sulfuric acid, and Triton X-100 were obtained from Sigma-Aldrich.

12-Lipoxygenase qHTS Assay (AID: 1452): All screening operations were performed on a fully integrated robotic system (Kalypsys Inc, San Diego, Calif.). (Inglese, J. et al.

*Proc. Natl. Acad. Sci. U.S.A.* 2006, 103, 11473-11478.) Three μL of enzyme (approximately 80 nM 12-LOX, final concentration) was dispensed into 1536-well Greiner black clear-bottom assay plates. Compounds and controls (23 nL) were transferred via Kalypsys PinTool equipped with 1536-pin array. The plate was incubated for 15 min at room temperature, and then a 1 μL aliquot of substrate solution (50 μM arachidonic acid final concentration) was added to start the reaction. The reaction was stopped after 6.5 min by the addition of 4 μL FeXO solution (final concentrations of 200 μM Xylenol Orange (XO) and 300 μM ferrous ammonium sulfate in 50 mM sulfuric acid). After a short spin (1000 rpm, 15 sec), the assay plate was incubated at room temperature for 30 minutes. The absorbances at 405 and 573 nm were recorded using ViewLux high throughput CCD imager (Perkin-Elmer, Waltham, Mass.) using standard absorbance protocol settings. During dispense, enzyme and substrate bottles were kept submerged into a +4° C. recirculating chiller bath to minimize degradation. Plates containing DMSO only (instead of compound solutions) were included approximately every 50 plates throughout the screen to monitor any systematic trend in the assay signal associated with reagent dispenser variation or decrease in enzyme specific activity. Data were normalized to controls, and plate-based data corrections were applied to filter out background noise. Further details on data analysis are provided herein.

Lipoxygenase UV-Vis Assay: The inhibitor compounds were screened initially using one concentration point at 25 μM on a Perkin-Elmer Lambda 40 UV/Vis spectrophotometer. The percent inhibition was determined by comparing the enzyme rates of the control (DMSO solvent) and the inhibitor sample by following the formation of the conjugated diene product at 234 nm ($\in=25,000$ M$^{-1}$ cm$^{-1}$). The reactions were initiated by adding either of 30 nM 12-LOX, 40 nM 15-LOX-1, 200 nM 15-LOX-2 or 5-10 μL of 5-LOX crude extract to a cuvette with a 2 mL reaction buffer constantly stirred using a magnetic stir bar at room temperature (22° C.). Reaction buffers used for various lipoxygenase were as follows: 25 mM HEPES (pH 7.3), 0.3 mM CaCl$_2$, 0.1 mM EDTA, 0.2 mM ATP, 0.01% Triton X-100, 10 μM AA for the crude, ammonium sulfate precipitated 5-LOX; and 25 mM HEPES (pH 7.5), 0.01% Triton X-100, 10 μM AA for 12-LOX, 15-LOX-1 and 15-LOX-2. The substrate concentration was quantitatively determined by allowing the enzymatic reaction to go to completion in the presence of 15-LOX-2. For the inhibitors that showed more than 50% inhibition at the one point screens, IC$_{50}$ values were obtained by determining the % inhibition, relative to solvent vehicle only, at various inhibitor concentrations. The data was then plotted against inhibitor concentration, followed by a hyperbolic saturation curve fit (assuming total enzyme concentration [E]<<K$_i^{app}$, so IC$_{50}$~K$_i^{app}$). It should be noted that all of the potent inhibitors displayed greater than 80% maximal inhibition, unless stated in the tables. Inhibitors were stored at −20° C. in DMSO Steady State Inhibition Kinetics: The steady-state kinetics experiments were performed with ML355 to determine the mode of inhibition. The inhibitor concentrations of 0, 0.1, 0.2 and 0.35 μM were used. Reactions were initiated by adding substrate (range 1-5 μM AA) to approximately 30 nM 12-LOX in a constantly stirring 2 mL cuvette containing 25 mM HEPES buffer (pH 7.5), in the presence of 0.01% Triton X-100. Lipoxygenase rates were determined by monitoring the formation of the conjugated product, 12-HPETE, at 234 nm ($\in=25\,000$ M$^{-1}$ cm$^{-1}$) with a Perkin-Elmer Lambda 45 UV/Vis spectrophotometer. It should be noted that 12-LOX displays higher error in the K$_M$ values at low substrate concentrations (<1 μM) due to the limits of the spectrophotometer. To minimize this inherent error, it is best to add 12-LOX first, and then quickly initiate the reaction with the addition of the appropriate amount of substrate, which yielded significantly more reproducible results. The substrate concentration was quantitatively determined by allowing the enzymatic reaction to proceed to completion, using 15-LOX-2. Kinetic data were obtained by recording initial enzymatic rates, at varied substrate and inhibitor concentrations, and subsequently fitted to the Henri-Michaelis-Menten equation, using KaleidaGraph (Synergy) to determine the microscopic rate constants, V$_{max}$ (μmol/min/mg) and V$_{max}$/K$_M$ (μmol/min/mg/μM). The kinetic rate constants were subsequently replotted with 1/V$_{max}$, K$_M$/V$_{max}$ and 1/K$_M$ versus inhibitor concentration, yielding K$_i$.

Pseudoperoxidase Assay: The pseudo-peroxidase activity rates were determined with BWb70c as the positive control, 13-(S)—HPODE as the oxidizing product and 12-LOX or 15-LOX-1 on a Perkin-Elmer Lambda 40 UV/Vis spectrophotometer, as described previously.[25] Activity was determined by monitoring the decrease at 234 nm (product degradation) in buffer (50 mM Sodium Phosphate (pH 7.4), 0.3 mM CaCl$_2$, 0.1 mM EDTA, 0.01% Triton X100, and 20 μM 13-(S)—HPODE). About 60 nM 12-LOX was added to 2 mL buffer containing 20 μM 13-(S)—HPODE, constantly stirred with a rotating stir bar (22° C.). Reaction was initiated by addition of 20 μM inhibitor (1:1 ratio to product). The percent consumption of 13-(S)—HPODE was recorded and loss of product less than 20% was not considered as viable redox activity. Individual controls were conducted consisting of enzyme alone with product and ML355 alone with enzyme. These negative controls formed the baseline for the assay, reflecting non-pseudo-peroxidase dependent hydroperoxide product decomposition. To rule out the auto-inactivation of the enzyme from pseudo-peroxidase cycling, the 12-LOX residual activity was measured after the assay was complete. 20 μM AA was added to the reaction mixture and the residual activity was determined by comparing the initial rates with inhibitor and 13-(S)—HPODE versus inhibitor alone, since the inhibitor by itself inherently lowers the rate of the oxygenation. Activity is characterized by direct measurement of the product formation with the increase of absorbance at 234 nm.

Cyclooxygenase assay: Roughly 2-5 μg of either COX-1 or COX-2 were added to buffer containing 0.1 M Tris-HCl buffer (pH 8.0), 5 mM EDTA, 2 mM phenol and 1 μM hematin at 37° C. The selected inhibitors were added to the reaction cell, followed by an incubation of 5 minutes with either of the COX enzymes. The reaction was then initiated by adding 100 μM AA in the reaction cell. Data was collected using a Hansatech DW1 oxygen electrode and the consumption of oxygen was recorded. Indomethasin and the solvent DMSO, were used as positive and negative controls, respectively and the percent inhibition of the enzyme was calculated by comparing the rates from samples and the controls Platelet Aggregation: Washed platelets were adjusted to a final concentration of 3×10$^8$ platelets/mL. Where indicated, platelets were pretreated with ML355 for 10 min at the indicated concentrations for 1 min. The aggregation response to PAR4-AP was measured using an aggregometer with stirring at 1100 RPM at 37° C.

Calcium Mobilization: Platelets were recalcified to a final concentration of 1 mM followed by pre-incubation with Fluo-4 AM for 10 min. The platelets were then treated with ML355 for 10 min at the indicated concentrations before stimulation with the indicated agonist. Calcium mobilization was measured using the Accuri C6 flow cytometer.

Mouse Beta cells (12-HETE Inhibition) Assay: Cells were gown to 90% confluency in 24 well plates in DMEM (Cat#11885092, Life Technologies Grand Island, N.Y.)+ 10% FBS. Cells were pre-treated with ML355 and stimulated as for human islets. After four hours, the media was removed and spun at 1000 RPM for 5 minutes. The cleared supernatant was stored at −80° C. prior to analysis. For analysis, supernatants were extracted on SepPak c18 SPE column (Cat# WAT054945, Waters Corporation, Milford, Mass.) and dried under nitrogen gas before reconstitution in 500 μL of 12-HETE ELISA buffer and analysis following manufacturers recommendations (Cat#901-050, Enzo Life Sciences, Plymouth Meeting, Pa.).

Human Islet (12-HETE Inhibition) Assay: Human donor islets obtained from integrated islet distribution program (www.iidp.coh.org) were incubated overnight in CMRL media (Cat#15-110-CV MediaTech, Inc. Manassas, Va.) containing 10% Fetal Bovine Serum, 1U penicillin 1 μg streptomycin (pen/strep). Islets were equilibrated in serum free media, (CMRL containing pen/Strep and 1% fatty acid free human serum albumin (Cat# A1887 Sigma, St. Louis, Mo.)), for 1 hour prior to pretreatment with 10 μM ML355 for 30 mins. For 12-HETE induction, islets were treated with 100 μM arachachidonic acid (Cat# BML-FA003-0100, Enzo Life Sciences Plymouth Meeting, Pa.), and 5 μM A23187 (Cat# C7522, Sigma, St. Louis, Mo.), for 4 hours at 37° C. Islets were harvested, centrifuged at 1000 RPM for 5 minutes with cleared supernatant and islet pellet being stored at −80° C. For extraction of the supernatants, samples were acidified to pH 3 with 1N HCl for 30 minutes and spun at 1000 RPM for five minutes. Samples were added to a prepared column (prewashed with 3 mL EtOH, followed by 3 mL of H$_2$O) and washed with 3 mL H$_2$O, followed by 3 mL 15% EtOH, and 3 mL Hexane. The samples were eluted with 3 mL of ethyl acetate and dried under nitrogen gas before, reconstitution in 500 mL of 12-HETE ELISA sample buffer (Enzo Life Sciences, Plymouth Meeting, Pa.). Cell pellets were extracted using CHCl$_3$/MeOH and samples dried under nitrogen gas before reconstitution in 250 μL of ELISA sample buffer. 12-HETE levels in samples were determined using a 12-HETE ELISA kit (Cat#901-050, Enzo Life Sciences, Plymouth Meeting, Pa.).

Examples Related to the Use of 12-Lipoxygenase Inhibitors in Platelet Activation and Treatment of Thrombosis Example: Platelet 12-LOX is Essential for FcγRIIa-Mediated Platelet Activation Pharmacological inhibition of 12-LOX in human platelets resulted in significant attenuation of FcγRIIa-mediated aggregation. 12-LOX was shown to be essential for FcγRIIa-induced PLCγ2 activity leading to activation of calcium mobilization, Rap1 and PKC activation, and subsequent activation of the integrin αIIbβ3. Additionally, platelets from transgenic mice expressing human FcγRIIa but deficient in platelet 12-LOX failed to form normal platelet aggregates and exhibited deficiencies in Rap1 and αIIbβ3 activation following stimulation of the FcγRIIa receptor. These results support an essential role for 12-LOX in regulating FcγRIIa-mediated platelet function and identify 12-LOX as a therapeutic target to limit immune-mediated thrombosis.

Platelet 12(S)-lipoxygenase (12-LOX), an oxygenase highly expressed in platelets, has been shown to potentiate the activation of select signaling pathways including protease-activated receptor 4 (PAR4) and an ITAM-containing receptor complex (GPVI-FcRγ). The most well understood function of 12-LOX is production of oxylipins, most notable being the conversion of arachidonic acid (AA) to 12-hydroxyeicosatretraenoic acid (12-HETE) upon agonist stimulation of platelets through both GPCR- and non-GPCR-mediated pathways. 12-HETE is an oxylipin that has been shown to be pro-thrombotic in platelets. In carotid endarterectomy patients, intra-operative heparin increases the level of plasma 12-HETE which correlates with the patient's platelet reactivity to ADP ex vivo. While the mechanism by which 12-LOX regulates platelet activity remains to be fully elucidated, previous publications have demonstrated the ability of 12-LOX activity to augment key signaling components of platelet activation including Rap1, Ca$^{2+}$ mobilization, αIIbβ3 activation, and dense granule secretion. Since 12-LOX activity was recently shown to be required for normal GPVI-mediated platelet activation and FcγRIIa shares common signaling components with GPVI, the inventors sought to identify if 12-LOX is a vital component of the FcγRIIa signaling pathway.

In this study human platelets were treated with a 12-LOX inhibitor, ML355, or vehicle control prior to FcγRIIa stimulation to determine if 12-LOX plays a role in the FcγRIIa signaling pathway. Pharmacological inhibition of 12-LOX activity in human platelets attenuated FcγRIIa-mediated platelet aggregation. Consistent with the human studies, murine platelets isolated from hFcR transgenic mice deficient in 12-LOX had an attenuated aggregation in response to FcγRIIa stimulation compared to wild-type hFcR transgenic mice. The activity of 12-LOX was further demonstrated to be essential for early PLCγ2 activation as well as other downstream effectors, such as calcium mobilization, Rap1, PKC, αIIbβ3 activation, and dense granule secretion, while not directly impinging on the phosphorylation of FcγRIIa itself. This study is the first to identify 12-LOX activity as an essential component of normal FcγRIIa signaling in platelets. Further, the results of this study suggest for the first time that 12-LOX may represent a novel therapeutic target to treat immune-mediated thrombocytopenia and thrombosis.

12-LOX Regulates FcγRIIa-Mediated Platelet Aggregation

Figures 11A, 11B:
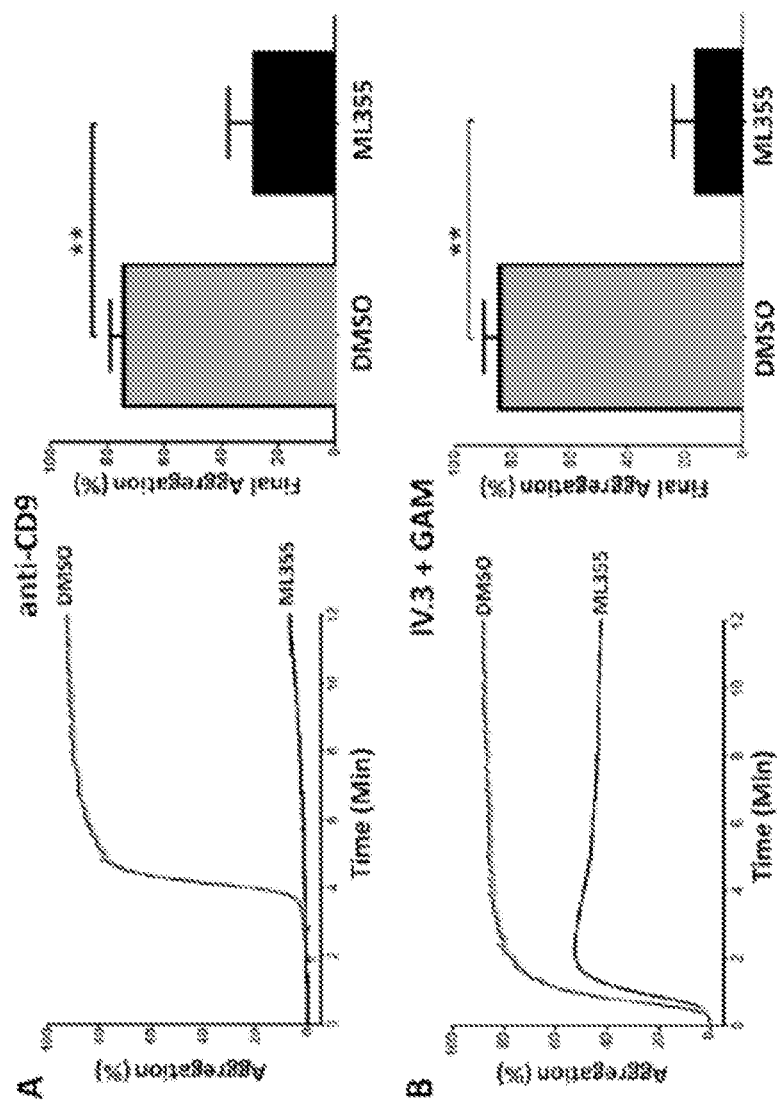
FIGS. 11A-11B show that 12-LOX modulates FcγRIIa-mediated platelet aggregation. Washed human platelets were pretreated with DMSO (vehicle control) or ML355 (20 µM) for 15 minutes and platelet aggregation was measured following FcγRIIa stimulation by (FIG. 11A) anti-CD9 or (FIG. 11B) crosslinking of IV.3, a FcγRIIa mouse monoclonal antibody, and goat anti-mouse Fab2 (IV.3+GAM). Left panel depicts a representative aggregation tracing of anti-CD9 antibody stimulated platelets pre-treated with ML355 or DMSO. Right panel depicts final platelet aggregation of anti-CD9 stimulated platelets that had been treated with ML355 (n=7) or DMSO (n=4). **P<0.01.
Figures 12A, 12B, 12C:
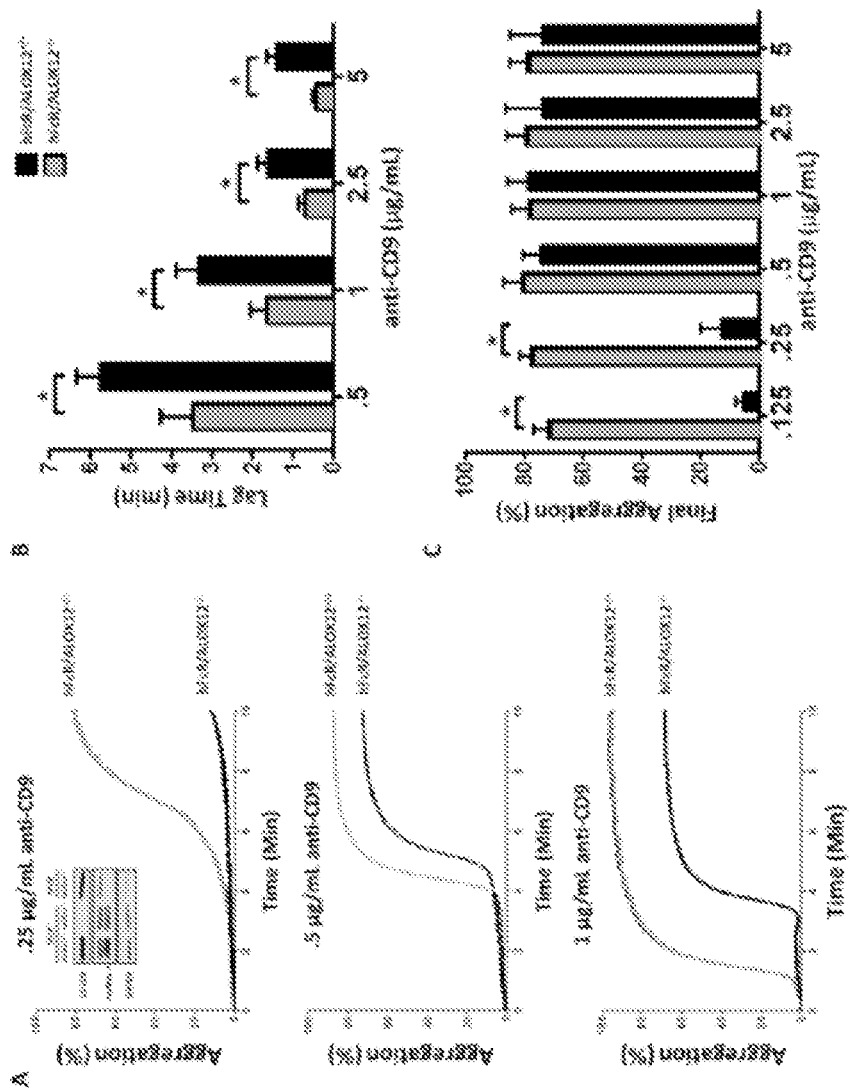
FIGS. 12A-12C show that murine platelets require 12-LOX for normal FcγRIIa-induced platelet aggregation. A dose response of anti-CD9-induced platelet aggregation was performed with washed platelets from hFcR/ALOX12$^{+/+}$ or hFcR/ALOX12$^{-/-}$ mice. Prior to aggregation fibrinogen (75 µg/mL) and $CaCl_2$ (1 mM) were added to platelets.

12-LOX was previously shown to regulate GPVI-mediated platelet aggregation. In platelets, FcγRIIa utilizes many of the same downstream signaling effectors as GPVI-FcRγ (4). To determine if 12-LOX plays a role in FcγRIIa-mediated platelet aggregation, washed human platelets were treated with ML355, a selective 12-LOX inhibitor or DMSO (vehicle control) followed by FcγRIIa-induced aggregation. Inhibition of platelet 12-LOX activity attenuated FcγRIIa-mediated platelet aggregation via anti-CD9 stimulation (FIG. 11A) or FcγRIIa antibody cross-linking (FIG. 11B). To confirm the decrease in FcγRIIa-mediated platelet aggregation was due to pharmacological inhibition of 12-LOX and not an off-target effect of the ML355, ex vivo platelet aggregation was measured following anti-CD9 stimulation in humanized FcγRIIa (hFcR) transgenic mice expressing 12-LOX (ALOX12$^{+/+}$) or deficient in 12-LOX (ALOX12$^{−/−}$). Platelets from mice deficient in 12-LOX (hFcR/ALOX12$^{−/−}$) showed a delayed (FIG. 12B) and attenuated (FIG. 12C) aggregation in response to anti-CD9 stimulation (0.125 and 0.25 μg/mL) when compared to platelets from mice expressing functional 12-LOX (hFcR/

ALOX12$^{+/+}$). These data suggest that platelets lacking 12-LOX activity through pharmacological or genetic ablation exhibits a significantly attenuated aggregation response to FcγRIIa activation.

12-LOX Regulates αIIbβ3 and Rap1 Activity in FcγRIIa Stimulated Platelets

Figures 13A, 13B:
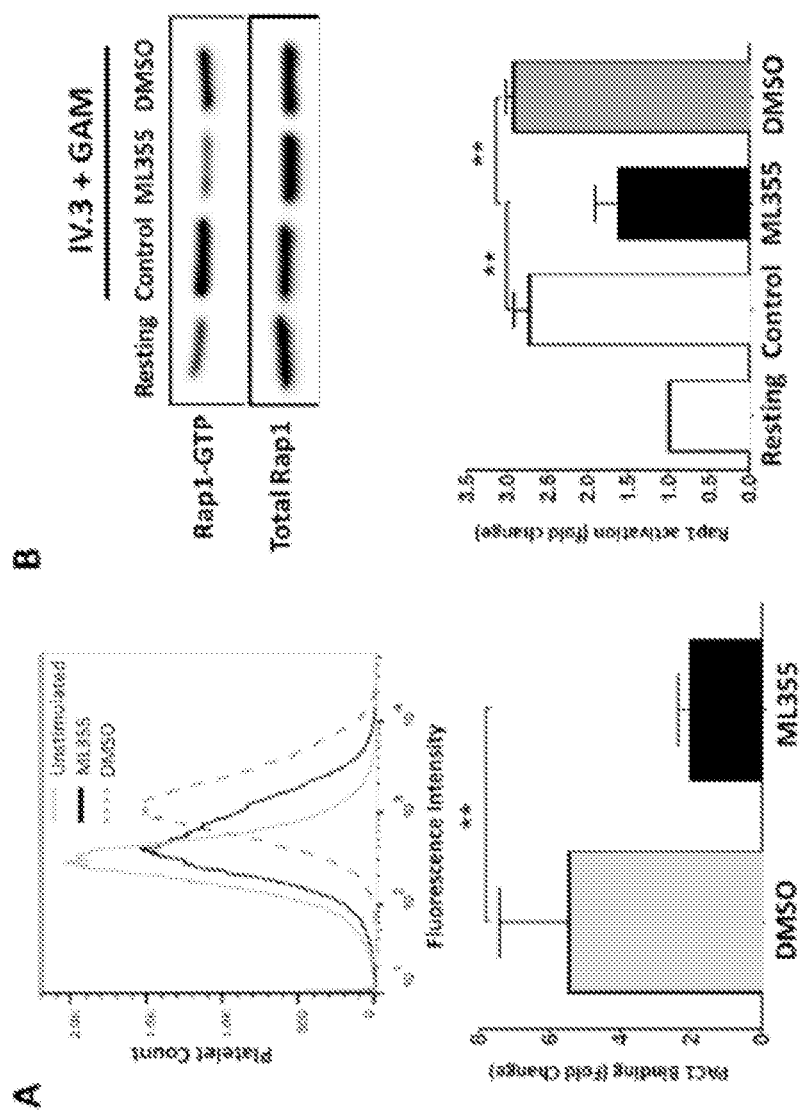
FIGS. 13A-13B show that FcγRIIa-mediated Rap1 and integrin αIIbβ3 activation are potentiated by 12-LOX. Washed human platelets pre-treated with ML355 or DMSO were stimulated with IV.3 and GAM crosslinking and (FIG. 13A) αIIbβ3 integrin activation and (FIG. 13B) Rap1 activation were assessed. PAC1-FITC was used to measure αIIbβ3 activation by flow cytometry. A composite bar graph of PAC1-FITC fold changes relative to the unstimulated PAC1-FITC fluoresence. Activated Rap1 was pulled down using Ral-GDS and blotted with a Rap1 antibody. Active Rap1 was measured using LI-COR and then normalized to total Rap1 and unstimulated for fold change in Rap1 activity. ** P<0.01

FIGS. 11 and 12 suggest 12-LOX is essential for normal FcγRIIa-mediated platelet aggregation; however, the component(s) in the FcγRIIa pathway regulated by 12-LOX remain unclear. As the activation of integrin αIIbβ3 is required for platelet aggregation, the potential role of 12-LOX in mediating αIIbβ3 activation in FcγRIIa-stimulated platelets was investigated, αIIbβ3 activation was measured by flow cytometry in FcγRIIa-stimulated platelets treated with ML355. Rap1 is a small GTPase whose activation is essential for activation of αIIbβ3. Therefore, Rap1 activation was measured following FcγRIIa stimulation in platelets following treatment with or without ML355. As shown in FIG. 13B, while stimulation of platelets in the absence of pretreatment (control) resulted in a significant increase in Rap1-GTP, platelets treated with ML355 failed to activate Rap1. Platelets treated with DMSO showed no attenuation in active Rap1 compared to control.

Figures 14A, 14B:
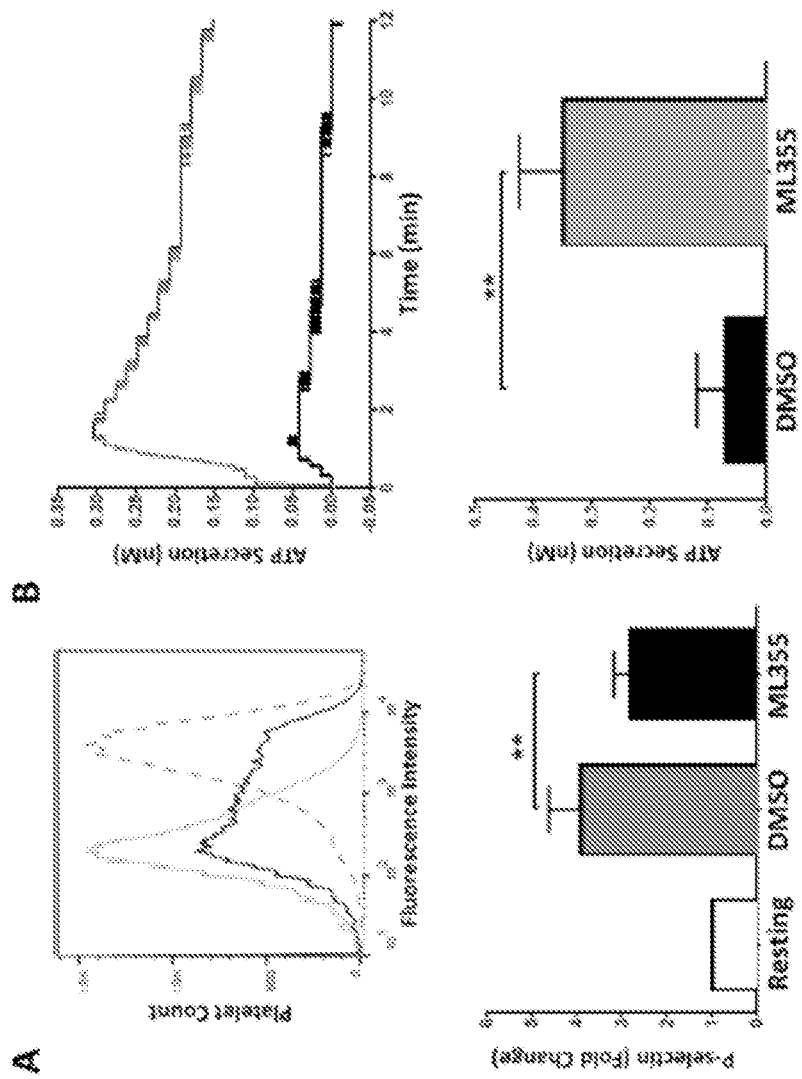
FIGS. 14A-14B show that dense granule secretion mediated by FcγRIIa activation is regulated by 12-LOX. Washed human platelets pre-treated with DMSO or ML355 were stimulated by FcγRIIa crosslinking (IV.3+GAM) and (FIG. 14A) alpha granule secretions was measured by using P-Selectin-PE conjugated antibody in a flow cytometer, while (FIG. 14B) ATP secretion was measured as a surrogate marker for dense granule secretion in an aggregometer. A composite of P-Selectin stained platelets treated with ML355 or DMSO (n=4). A bar graph of DMSO or ML355 treated platelets measured for ATP secretion following FcγRIIa crosslinking (n=4).

12-LOX Regulates Dense but not Alpha Granule Secretion in FcγRIIa Activated Platelets The release of alpha and dense granules from activated platelets serves to amplify platelet aggregation. Surface expression of P-selectin was used as a surrogate marker to measure alpha granule secretion in FcγRIIa-stimulated platelets. Treatment with ML355 did not result in attenuation of agonist-induced surface expression of P-selectin compared to control conditions (FIG. 14A). However, FcγRIIa-stimulated platelets treated with ML355 showed a significant decrease in ATP release compared with DMSO treated platelets (FIG. 14B). These data suggest 12-LOX is a regulator of dense secretion downstream of FcγRIIa stimulation in platelets.

12-LOX Modulates Proximal Signaling Components of the FcγRIIa Pathway in Human Platelets As shown in FIG. 13, 12-LOX activity is required for the normal activation of distal signaling components (Rap1, αIIbβ3, and platelet aggregation) of the FcγRIIa pathway. Crosslinking of FcγRIIa with immunoglobulins also initiates proximal signaling components' activation that eventually leads to platelet aggregation. FcγRIIa initiates ITAM phosphorylation resulting in Syk activation. Syk activation leads to activation of phospholipase gamma 2 (PLCγ2) resulting in calcium release and PKC activation, both of which are critical for platelet activation. To determine where in this complex signaling milieu 12-LOX plays an essential role in FcγRIIa signaling in the platelet, the individual signaling components directly downstream of FcγRIIa initiation were assessed in the presence or absence of ML355.

Figures 15A, 15B:
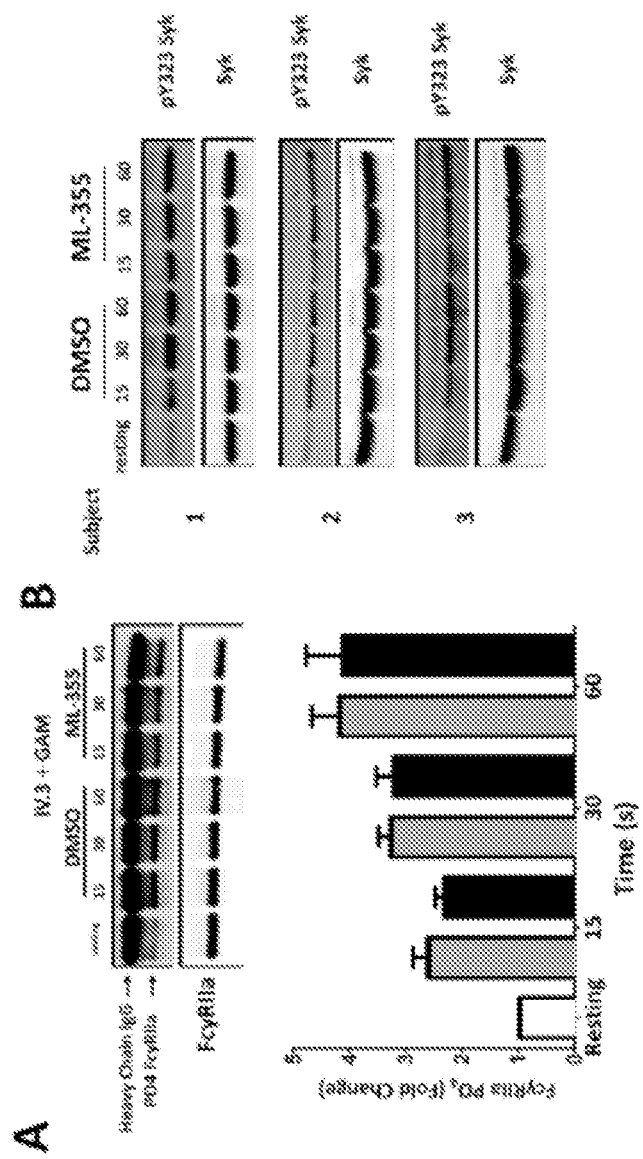
FIGS. 15A-15B show the role of 12-LOX in regulating the FcγRIIa signaling complex. Washed human platelets were pre-treated with ML355 (20 μM) or vehicle control prior to IV.3 and GAM stimulation.

To investigate whether 12-LOX directly regulated FcγRIIa phosphorylation, FcγRIIa was immunoprecipitated from IV.3+GAM-stimulated platelets treated with ML355 or DMSO and immunoblotted for phosphorylation of FcγRIIa. No difference in FcγRIIa phosphorylation was detected in FcγRIIa-stimulated platelets in control or ML355 treated conditions (FIG. 15A). This data suggests that 12-LOX activity is not required for phosphorylation of FcγRIIa itself.

Figures 16A, 16B, 16C:
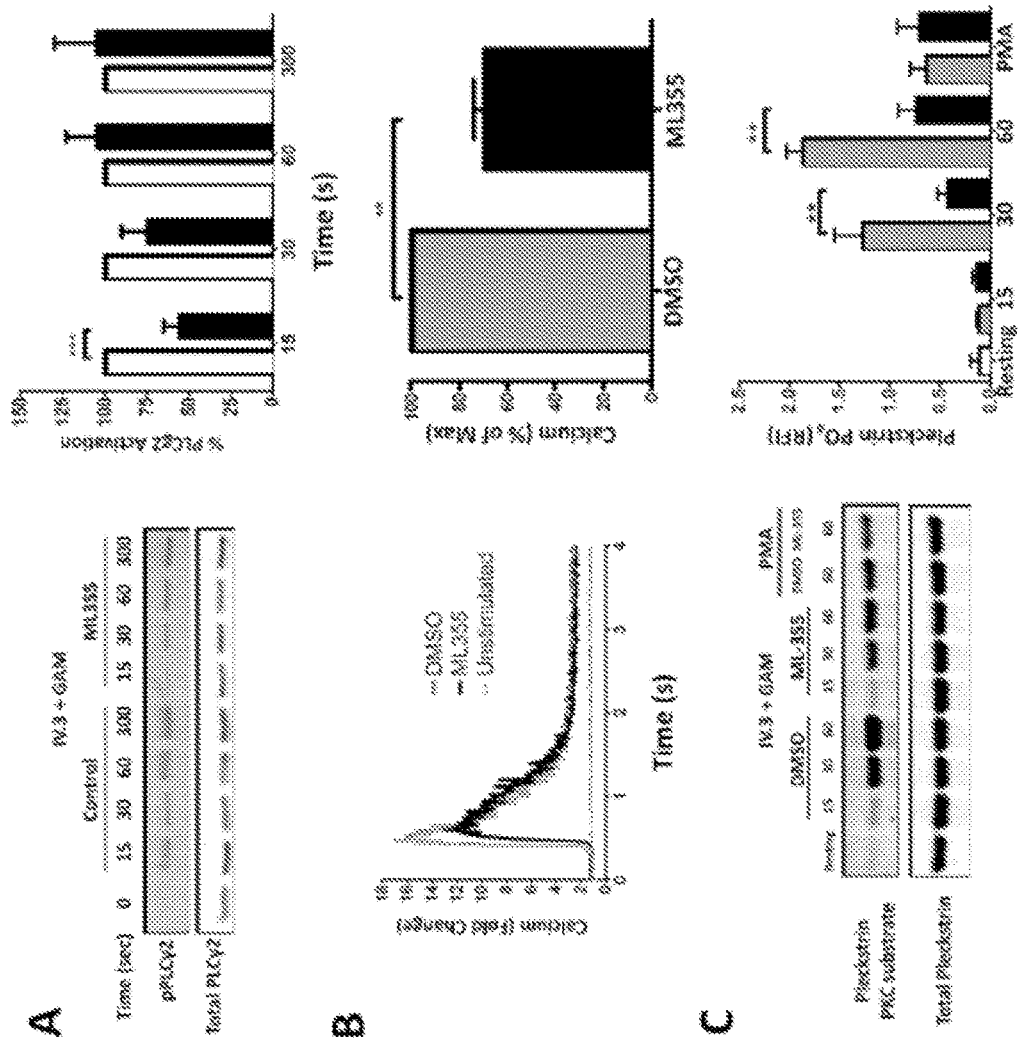
FIGS. 16A-16C show that 12-LOX modulates early signaling components of the FcγRIIa pathway in human platelets. Washed human platelets were pre-treated with ML355 (20 μM) or vehicle control prior to IV.3 and GAM stimulation.

Phosphorylation of FcγRIIa results in recruitment and activation of the tyrosine kinase Syk which is crucial for the formation of the LAT signalosome. The phosphorylation of Syk was measured following FcγRIIa stimulation of platelets in the presence or absence of ML355. The degree of Syk phosphorylation in response to FcγRIIa cross-linking in the presence of ML355 was varied in the subjects tested and may be due to inter-individual variability. Hence, while the observed attenuation of Syk phosphorylation in the presence of ML355 was minor, the number of subjects tested was too small to definitively identify Syk as a node of regulation by 12-LOX (FIG. 15B). To assess if 12-LOX regulates PLCγ2 activation downstream of FcγRIIa, PLCy2 phosphorylation was measured in washed human platelets in the presence or absence of ML355. Platelets stimulated by FcγRIIa antibody cross-linking were phosphorylated within 15 seconds following stimulation. Platelets treated with ML355 however showed attenuated PLCy2 phosphorylation at 15 and 30 seconds compared to control conditions (FIG. 16A).

Since 12-LOX attenuated FcγRIIa-mediated PLCγ2 activation, its effects on intracellular calcium release were measured. Washed human platelets were stimulated by FcγRIIa-mediated antibody cross-linking in the presence of ML355 or vehicle control and calcium release was measured. Platelets treated with ML355 exhibited a decrease in intracellular Ca$^{2+}$ following platelet stimulation compared to DMSO treated platelets (FIG. 16B). As PLCy2 activation leads to activation of PKC in in platelets in part through calcium mobilization, the potential regulation of FcγRIIa-mediated PKC activity by 12-LOX was also evaluated. A significant decrease in PKC activation in platelets treated with ML355 at 30 and 60 seconds was observed compared to platelets treated with the vehicle control (FIG. 16C). This regulation of PKC was determined to be indirect since PKC activation by PMA, a direct PKC activator, showed no difference in its ability to activate PKC either in control or ML355 treated platelets.

Discussion

Figure 17:
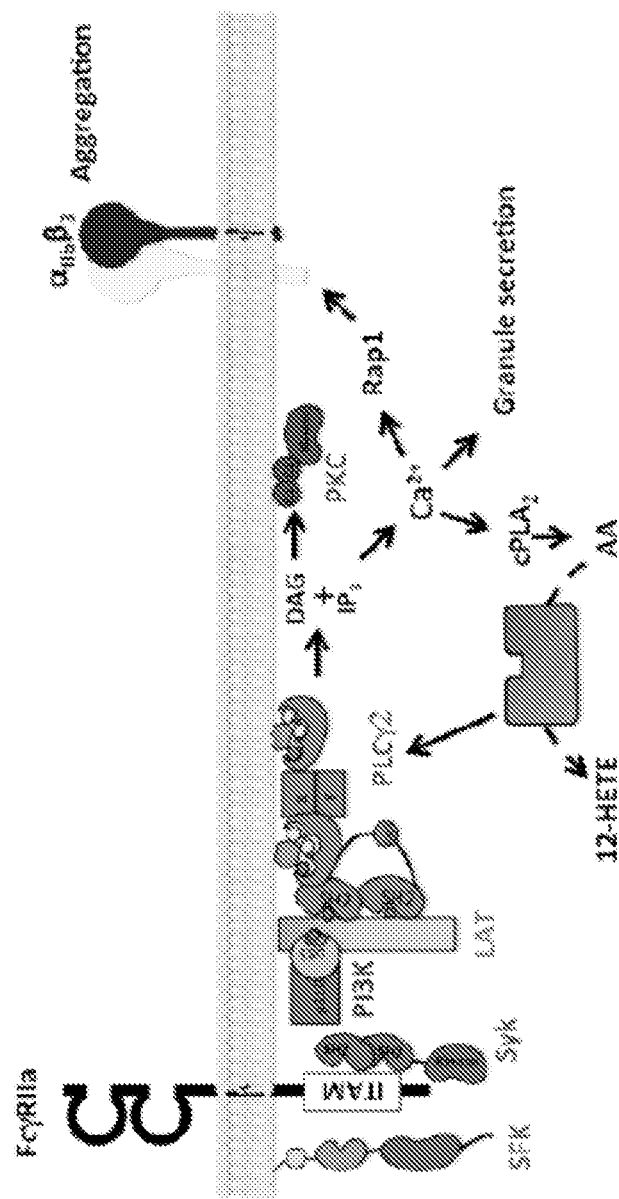
FIG. 17 is a schematic model of 12-LOX role in the regulation of FcγRIIa pathway. 12-LOX regulates early PLCγ2 activation-mediated by FcγRIIa stimulation, which is essential for full calcium release in the platelets. Calcium flux is required for cPLA2 activity to generate free fatty acids, such as arachidonic acid (AA). Subsequently, Rap1 activation is also dependent on 12-LOX activity in order to activate integrin αIIbβ3 for platelet aggregation.
Figures 18A, 18B:
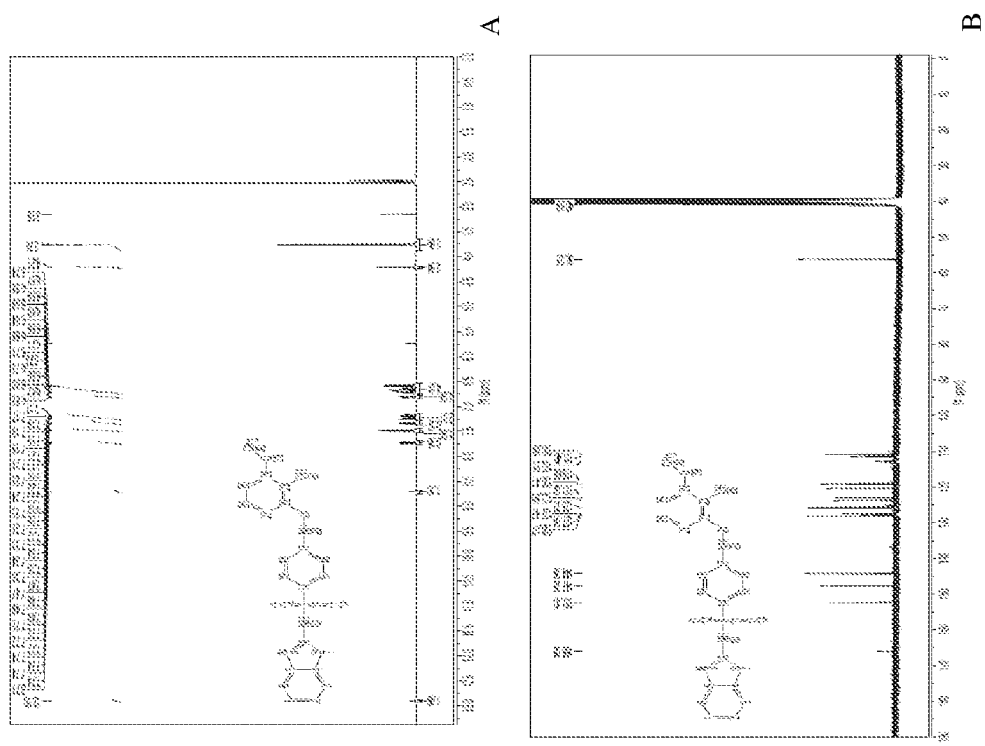
FIG. 18 shows $^1$H NMR data for compound ML355 (FIG. 18A) and $^{13}$C NMR for compound ML-355 (FIG. 18B).
Figure 19:
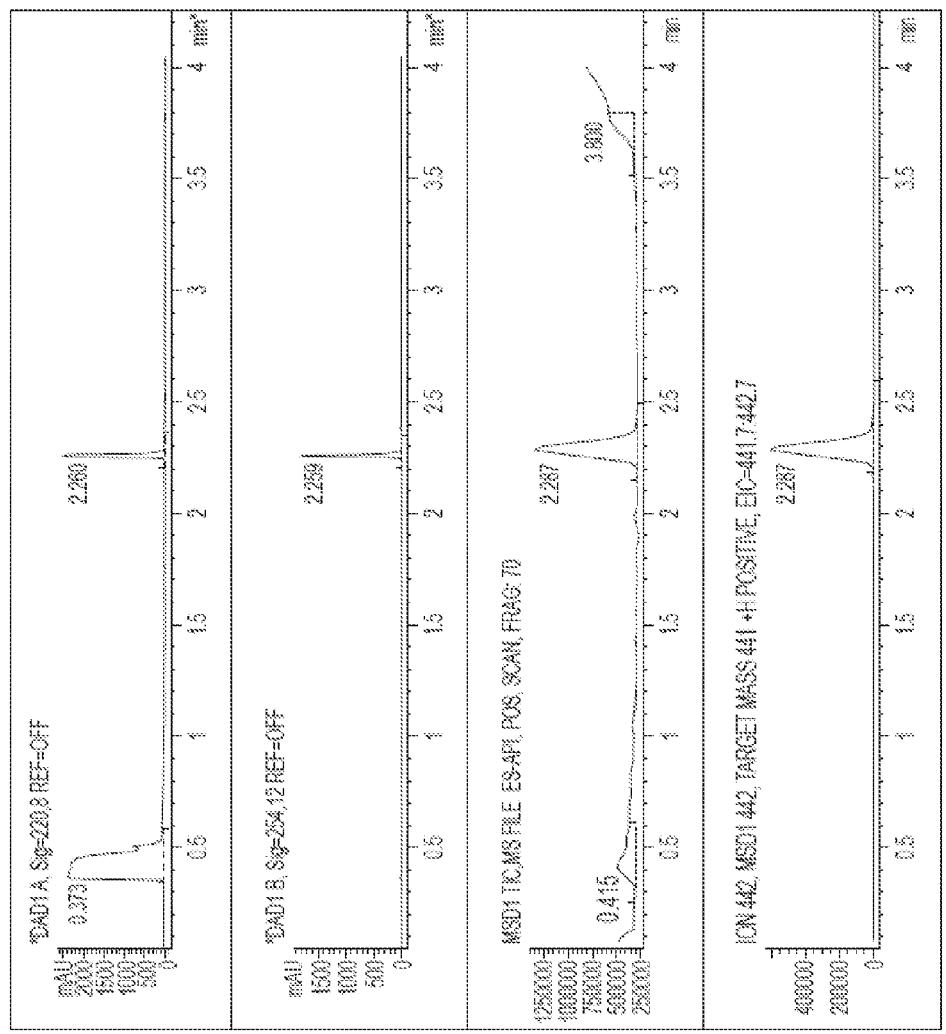
FIG. 19 shows LC/MS characterization for compound ML355 at 220 nm (top) and 254 nm (bottom).
Figures 20A, 20B:
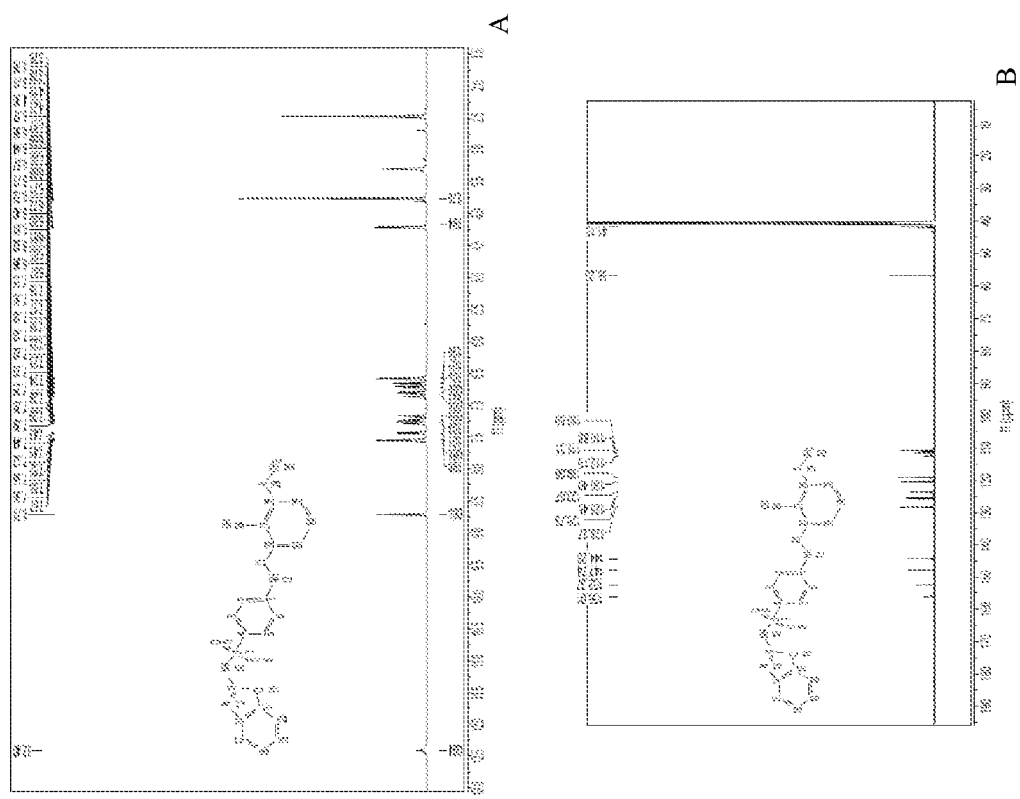
FIG. 20 shows $^1$H NMR data for compound 36 (FIG. 20A) and $^{13}$C NMR for compound 36 (FIG. 20B).
Figure 21:
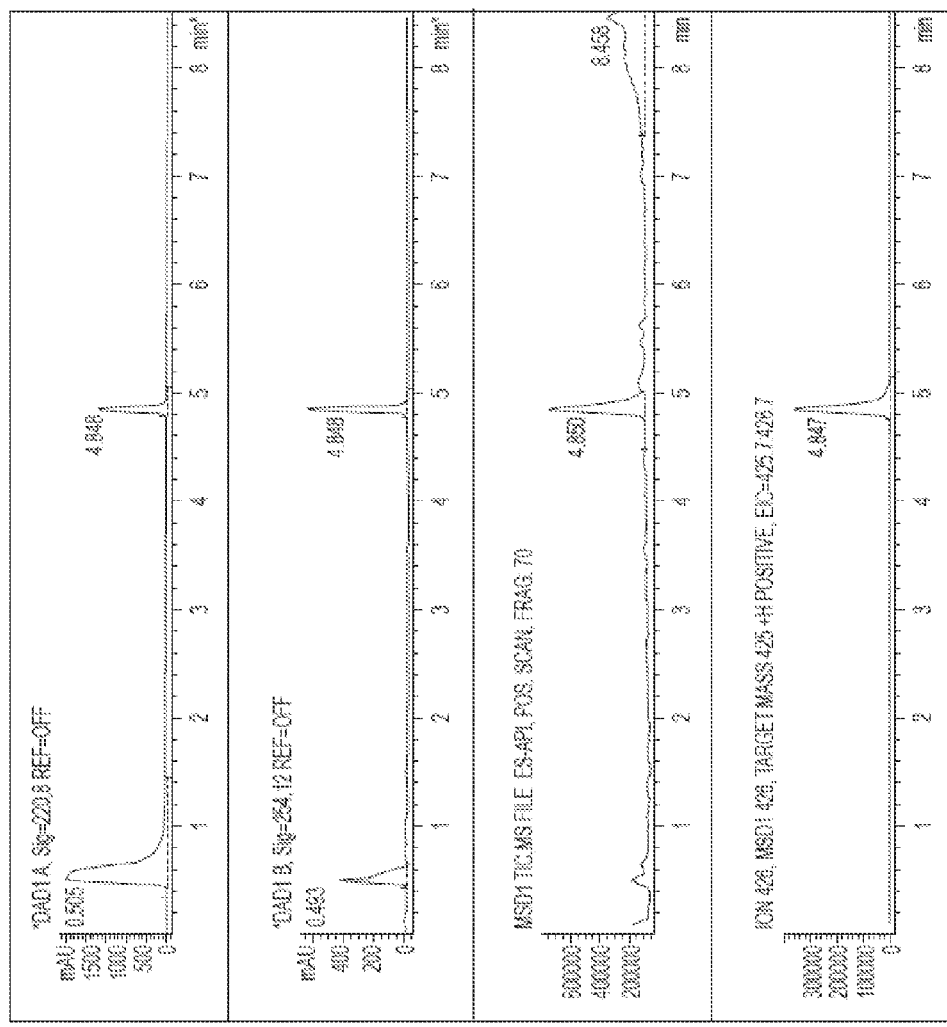
FIG. 21 shows LC/MS characterization for compound 36 at 220 nm (top) and 254 nm (bottom).
Figures 22A, 22B:
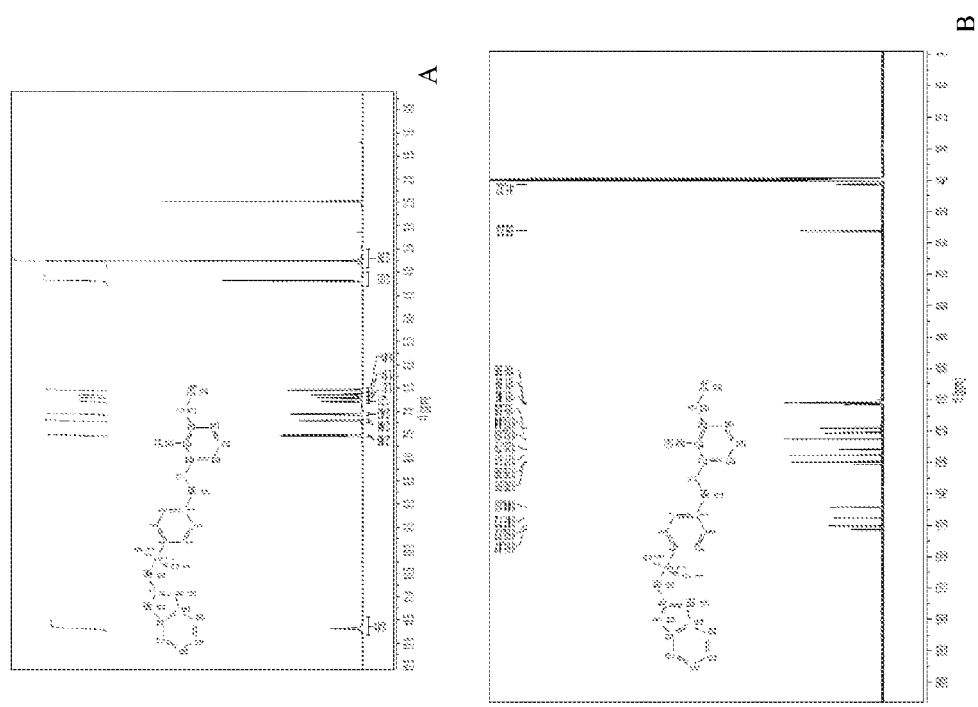
FIG. 22 shows $^1$H NMR data for compound 37 (FIG. 22A) and $^{13}$C NMR for compound 37 (FIG. 22B).
Figure 23:
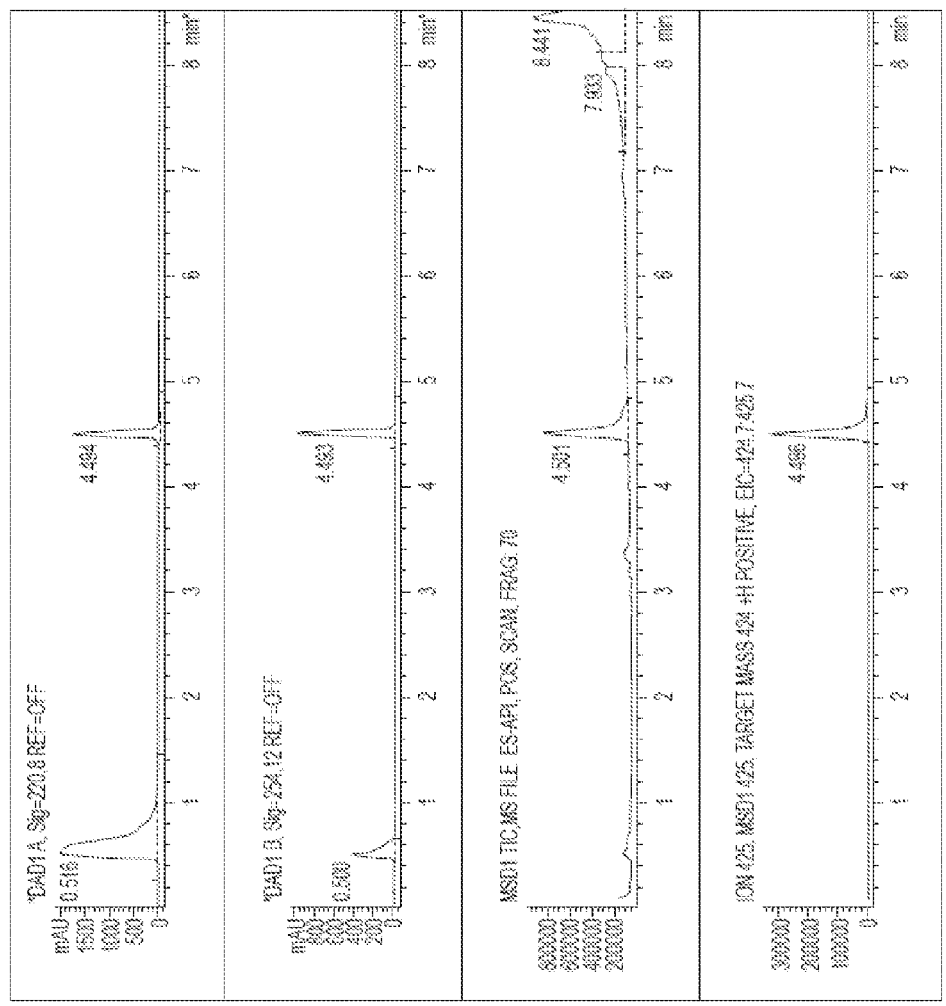
FIG. 23 shows LC/MS characterization for compound 37 at 220 nm (top) and 254 nm (bottom).

12-LOX has recently been shown to be an important regulator of GPVI-mediated platelet activation As FcγRIIa and GPVI are purported to signal via a conserved pathway, 12-LOX may play an essential role in the regulation of FcγRIIa signaling in human platelets. This study is the first to demonstrate that 12-LOX is an essential component of FcγRIIa immune mediated platelet activation. Human platelets treated with a 12-LOX inhibitor, ML355, or FcγRIIa transgenic mouse platelets deficient in 12-LOX, showed significantly attenuated aggregation in response to FcγRIIa-mediated activation. To investigate the underlying mechanism by which 12-LOX regulates FcγRIIa-mediated platelet activation, the activity of multiple signaling intermediates in the FcγRIIa pathway were assessed in the presence of the 12-LOX inhibitor ML355. Following stimulation, platelets treated with ML355 were significant attenuated along multiple signaling steps in the immune-mediated FcγRIIa activation pathway including αIIbβ3, Rap1, Ca2+, PLCγ2, PKC, and dense granule secretion (FIG. 17).

The primary known function of 12-LOX is to produce oxylipins (such as 12(S)-HETE) from the fatty acid substrate AA, the predominant fatty acid in the platelet, following platelet activation. Previous publications have shown selective 12-LOX inhibitors significantly reduced 12-HETE production. Though blocking 12-HETE production has been associated with reduced platelet-mediated reactivity, the direct role of 12-HETE on platelet activation remains unclear. Oxylipins generated from COX-1, another oxygenase in platelets, generally act as signaling mediators through GPCRs on the platelet surface. In the case of 12-HETE, published work has demonstrated it signals through GPR31, a GPCR; however, while recent genetic screens have shown the expression of GPR31 in human platelets, there is no direct evidence of GPR31 protein expression on the surface of platelets. In addition to potential autocrine or paracrine signaling through GPR31, 12-LOX oxylipins produced in the platelet may incorporate back into the membrane to induce their regulatory effects. There is a precedent for oxylipin integration into the membrane as 12-HETE has been shown to be esterified into phospholipids in the plasma membrane upon platelet activation. A third potential explanation of the mechanism by which 12-LOX regulates FcγRIIa-mediated signaling may be through direct or indirect 12-LOX scaffolding within the cell. 12-LOX complex formation as a means to regulate downstream signaling has previously been implicated in regulation of cell growth and tumorgenesis. While all of these regulatory mechanisms are plausible, the rapid speed by which 12-LOX impinges on the FcγRIIa pathway leaves favors the possibility that 12-LOX and not a 12-LOX oxylipin may act as a direct regulatory component of the FcγRIIa pathway.

Although 12-LOX activity is required for normal FcγRIIa-mediated platelet activation, the direct molecular component by which 12-LOX activity is required has yet to be determined. 12-LOX was not required for FcγRIIa phosphorylation and only partially affected Syk phosphorylation, suggesting 12-LOX activity is not directly regulating Src family kinase activity. However, 12-LOX activity was shown to be important for early PLCγ2 activation, indicating 12-LOX may be an important regulator in the kinetics of PLCγ2 activation affecting downstream effectors. The delay in PLCγ2 activation due to 12-LOX inhibition may be attributed to direct regulation of PLCγ2 or regulation of upstream effectors such as LAT or BTK. The data presented here narrows the scope of where 12-LOX impinges on the FcγRIIa pathway to a proximal point in the signaling pathway between the receptor and PLCγ2.

Methods

Mice and platelet preparation: FcγRIIA transgenic mice (hFcR/ALOX12$^{+/+}$) were bred with platelet 12-lipoxygenase knockout (ALOX12$^{-/-}$) mice to generate FcγRIIA transgenic mice deficient in platelet 12-lipoxygenase (hFcR/ALOX12$^{-/-}$). All mice were housed in the mouse facility of Thomas Jefferson University (TJU). Experimental procedures were approved by the Animal Care and Use Committee of TJU. Blood was drawn from the inferior vena cava of 12 week old anesthetized mice using a syringe containing sodium citrate. Mouse platelet preparation was prepared as described in (Yeung et al., 2012). Murine platelets were resuspended in tyrodes buffer containing fibrinogen (75 μg/mL) and CaCl$_2$ (1 mM).

Preparation of washed human platelets: Prior to blood collection written informed consent was obtained from all volunteers. Washed platelets were isolated from the blood of healthy volunteers as previously described (14). Washed platelets were resuspended in tyrodes buffer at $3.0 \times 10^8$ platelets/mL unless otherwise indicated. All studies performed with human platelets were approved by the Thomas Jefferson University Institutional Review Board.

FcγRIIa-mediated platelet activation: FcγRIIa-mediated platelet activation was initiated by two distinct models; either 1) FcγRIIa antibody cross-linking or 2) CD9 monoclonal antibody stimulation. To cross-link FcγRIIa, washed platelets were incubated with IV.3, an FcγRIIa mouse monoclonal antibody, for one minute followed by the addition of a goat anti-mouse (GAM) IgG antibody to cross-link FcγRIIa. The concentration of FcγRIIa cross-linking antibodies used for each experiment is indicated in the text. Alternatively, washed human platelets were stimulated with an anti-CD9 monoclonal antibody to activate FcγRIIa mediated signaling. Due to inter-individual variability in anti-CD9 response, a range of anti-CD9 concentration (0.25-1 ug/ml) was used to achieve an aggregation of EC80. In studies using the 12-LOX inhibitor (ML355), washed platelets were incubated with either ML355 (20 μM), or DMSO (vehicle control) for 15 minutes prior to FcγRIIa stimulation.

Platelet aggregation: Platelet aggregation was measured with a lumi-aggregometer (Chronolog Corp, Model 700D) under stirring conditions at 37° C.

PLCγ2 phosphorylation: Washed human platelets were adjusted to $5 \times 10^8$ platelets/mL and stimulated in an aggregometer by antibody cross-linking of FcγRIIa and lysed at designated times with 5× reducing buffer to stop the reaction. Samples were separated on a 7.5% SDS-PAGE gel. Antibodies to PLCγ2 and phospho-Y759 PLCγ2, a marker of PLCγ2 activation, were used to evaluate the relative levels of total and active PLCγ2, respectively.

Calcium mobilization: Intracellular calcium release was measured as previously described. Briefly, washed human platelets were resuspended at $1.0 \times 10^6$ platelets/mL in tyrodes buffer containing 1 mM calcium. Platelets were incubated with Fluo-4 am, a cell permeable calcium sensitive dye, for ten minutes prior to stimulation. Platelets were stimulated by FcγRIIa antibody cross-linking and fluorescence intensity was measured in real-time by flow cytometry. Data is reported as the fold change in the fluorescence intensity comparing maximum fluorescence intensity relative to fluorescence intensity prior to platelet stimulation.

Rap1 activation: Washed human platelets were stimulated by FcγRIIa antibody cross-linking for 5 minutes and aggregation was stopped with 2× platelet lysis buffer. RalGDS-RBD was used to selectively precipitate the active conformation of Rap1 from the platelet lysate as previously described. Total platelet lysate and Rap1 pull-down samples were run on a SDS-PAGE gel and identified by Western blot with a Rap1 antibody. The levels of active Rap1 were normalized to the amount of total Rap1 contained in each sample.

PKC activation assay: Washed platelets were stimulated by FcγRIIa antibody cross-linking under stirring conditions (1100 rpm) in an aggregometer at 37° C. Reactions were stopped by the addition of 5× Laemmli sample buffer at the indicated times. As a positive control platelets were treated with PMA (1 mM), a direct PKC agonist, for one minute. Samples were run on an SDS-PAGE gel and Western blots were performed using antibodies specific for PKC substrate phosphorylation and pleckstrin.

Dense granule secretion: ATP release was measured from washed platelets as surrogate for dense granule secretion. Prior to activation washed platelets were incubated with Chronolume Reagent, an ATP sensitive dye, for one minute. Platelets were stimulated with FcγRII antibody cross-linking under stirring conditions and fluorescence was measured in real-time using a lumi-aggregometer.

Alpha granule release and αIIbβ3 activation: Prior to stimulation, washed platelets were pre-incubated with a either FITC-conjugated P-selectin antibody or FITC-conjugated PAC-1, an antibody specific for the active conformation of αIIbβ3. Platelets were stimulated with FcγRIIa antibody cross-linking and reactions were stopped by the addition of 2% formaldehyde at indicated times. Fluorescence intensity was measured by flow cytometry. Results are reported as mean fluorescence intensity.

Western Blotting: Standard Western blots for Rap1 activation, PKC substrates, and PLCγ2 phosphorylation were used and band intensity were quantified with the Odyssey Infrared Imaging System (LIC-OR Biosystems).

Statistical analysis: Where applicable, data represents the mean±S.E.M. Statistical significance was determined using GraphPad Prism software. A P value less than 0.05 was considered significant.

REFERENCES

1. Aharony, D.; Smith, J. B.; Silver, M. J. Regulation of arachidonate-induced platelet aggregation by the lipoxygenase product, 12-hydroperoxyeicosatetraenoic acid. Biochim. Biophys. Acta 1982, 718, 193-200.
2. Amagata, T.; Whitman, S.; Johnson, T.; Stessmann, C. C.; Carroll, J.; Loo, C.; Clardy, J.; Lobkovsky, E.; Crews, P.; Holman, T. R. Sponge Derived Terpenoids with Selectivity towards Human 15-Lipoxygenase versus Human 12-Lipoxygenase. J. Nat. Prod. 2003, 66, 230-235.
3. Arai M, Yamamoto N, Moroi M, Akamatsu N, Fukutake K, and Tanoue K. Platelets with 10% of the normal amount of glycoprotein VI have an impaired response to collagen that results in a mild bleeding tendency. British journal of haematology. 1995; 89(1):124-30.
4. Asselin J, Gibbins J M, Achison M, Lee Y H, Morton L F, Farndale R W, Barnes M J, and Watson S P. A collagen-like peptide stimulates tyrosine phosphorylation of syk and phospholipase C gamma2 in platelets independent of the integrin alpha2beta1. Blood. 1997; 89(4): 1235-42.
5. Berger, W.; De Chandt, M. T.; Cairns, C. B. Zileuton: Clinical Implications of 5-Lipoxygenase Inhibition in Severe Airway Disease. Int. J. Clin. Pract. 2007, 61, 663-676.
6. Bergmeier W, and Stefanini L. Platelet ITAM signaling. Current opinion in hematology. 2013; 20(5):445-50.
7. Bertoni A, Tadokoro S, Eto K, Pampori N, Parise L V, White G C, and Shattil S J. Relationships between Rap1b, affinity modulation of integrin alpha IIbbeta 3, and the actin cytoskeleton. The Journal of biological chemistry. 2002; 277(28):25715-21.
8. Blake R A, Schieven G L, and Watson S P. Collagen stimulates tyrosine phosphorylation of phospholipase C-gamma 2 but not phospholipase C-gamma 1 in human platelets. FEBS letters. 1994; 353(2):212-6.
9. Bledzka K, Smyth S S, and Plow E F. Integrin alphaIIb-beta3: from discovery to efficacious therapeutic target. Circulation research. 2013; 112(8):1189-200.
10. Bleich, D.; Chen, S.; Zipser, B.; Sun, D.; Funk, C. D.; Nadler, J. L. Resistance to type 1 diabetes induction in 12-lipoxygenase knockout mice. J. Clin. Invest. 1999, 103, 1431-1436.
11. Brash, A. R. A review of possible roles of the platelet 12-lipoxygenase. Circulation 1985, 72, 702-707.
12. Brass L F, Manning D R, and Shattil S J. GTP-binding proteins and platelet activation. Progress in hemostasis and thrombosis. 1991; 10(127-174)
13. Catalano, A.; Procopio, A. New aspects on the role of lipoxygenases in cancer progression. Histol. Histopathol. 2005, 20, 969-975.
14. Chang, J.; Blazek, E.; Kreft, A. F.; Lewis, A. J. Inhibition of platelet and neutrophil phospholipase A2 by hydroxyeicosatetraenoic acids (HETES). A novel pharmacological mechanism for regulating free fatty acid release. Biochem. Pharmacol. 1985, 34, 1571-1575.
15. Chen, M.; Yang, Z. D.; Smith, K. M.; Carter, J. D.; Nadler, J. L. Activation of 12-Lipoxygenase in proinflammatory cytokine-mediated β-cell toxicity. Diabetologia 2005, 48, 486-495.
16. Chen, X.-S.; Brash, A.; and Funk, C. Purification and characterization of recombinant histidine-tagged human platelet 12-lipoxygenase expressed in a baculovirus/insect cell system. Eur. J. Biochem. 1993, 214, 845-852.
17. Chrzanowska-Wodnicka M, Smyth S S, Schoenwaelder S M, Fischer T H, and White G C, 2nd. Rap1b is required for normal platelet function and hemostasis in mice. The Journal of clinical investigation. 2005; 115(3):680-7.
18. Cichewicz, R. H.; Kenyon, V. A.; Whitman, S.; Morales, N. M.; Arguello, J. F.; Holman, T. R.; Crews, P. Redox inactivation of human 15-lipoxygenase by marine-derived meroditerpenes and synthetic chromanes: archetypes for a unique class of selective and recyclable inhibitors. J. Am. Chem. Soc. 2004, 126, 14910-14920.
19. Coffey M J, Jarvis G E, Gibbins J M, Coles B, Barrett N E, Wylie O R, and O'Donnell V B. Platelet 12-lipoxygenase activation via glycoprotein VI: involvement of multiple signaling pathways in agonist control of H(P)ETE synthesis. Circulation research. 2004; 94(12):1598-605.
20. Cyrus, T.; Witztum, J. L.; Rader, D. J.; Tangirala, R.; Fazio, S.; Linton, M. F.; Funk, C. D. Disruption of the 12/15-lipoxygenase gene diminishes atherosclerosis in apo E-deficient mice J. Clin. Invest. 1999, 103, 1597-1604.
21. Deschamps, J. D.; Gautschi, J. T.; Whitman, S.; Johnson, T. A.; Gassner, N. C.; Crews, P.; Holman, T. R. Discovery of platelet-type 12-human lipoxygenase selective inhibitors by high-throughput screening of structurally diverse libraries, Bioorg. Med. Chem. 2007, 15, 6900-6908.
22. Deschamps, J. D.; Kenyon, V. A.; Holman, T. R. Baicalein is a potent in vitro inhibitor against both reticulocyte 15-human and platelet 12-human lipoxygenases. Bioorg. Med. Chem. 2006, 14, 4295-4301.
23. Ettmayer, P.; Amidon, G. L.; Clement B.; Testa, B. Lessons learned from marketed and investigational prodrugs. J. Med. Chem. 2004, 47, 2393-2404.
24. Fukami M H, and Salganicoff L. Human platelet storage organelles. A review. Thrombosis and haemostasis. 1977; 38(4):963-70.
25. Fulp, A. B.; Johnson, M. S.; Markworth, J.; Marron, B. E.; Seconi, D. C.; West, C. W.; Wang, X.; Zhou, S. Sodium Channel Blockers. US Patent WO/2009/012242, Jul. 14, 2008.
26. Gan, Q.-F.; Browner, M. F.; Sloane, D. L.; Sigal, E. Defining the arachidonic acid binding site of human 15-lipoxygenase. J. Biol. Chem. 1996, 271, 25412-25418
27. Ghosh, J. Inhibition of Arachidonate 5-Lipoxygenase Triggers Prostate Cancer Cell Death through Rapid Activation of C-Jun N-Terminal Kinase. Biochem. Biophys. Res. Commun. 2003, 307, 342-349.
28. Ghosh, J., Myers, C. E. Inhibition of Arachidonate 5-Lipoxygenase Triggers Massive Apoptosis in Human Prostate Cancer Cells. Proc. Natl. Acad. Sci. U.S.A 1998, 95, 13182-13187.
29. Gibbins J, Asselin J, Farndale R, Barnes M, Law C L, and Watson S P. Tyrosine phosphorylation of the Fc receptor gamma-chain in collagen-stimulated platelets. The Journal of biological chemistry. 1996; 271 (30): 18095-9.
30. Greinacher A, Althaus K, Krauel K, and Selleng S. Heparin-induced thrombocytopenia. Hamostaseologie. 2010; 30(1):17-8, 20-8.
31. Guo Y, Zhang W, Giroux C, Cai Y, Ekambaram P, Dilly A K, Hsu A, Zhou S, Maddipati K R, Liu J, et al. Identification of the orphan G protein-coupled receptor 31. GPR31 as a receptor for 12-(S)-hydroxyeicosatetraenoic acid. The Journal of biological chemistry. 2011; 286(39): 33832-40.
32. Harats, D.; Shaish, A.; George, J.; Mulkins, M.; Kurihara, H.; Levkovitz, H.; Sigal, E. Overexpression of 15-lipoxygenase in vascular endothelium accelerates early atherosclerosis in LDL receptor-deficient mice. Arteriosler. Thromb. Vasc. Biol. 2000, 20, 2100-2105.
33. Holmsen H, and Weiss H J. Secretable storage pools in platelets. Annual review of medicine. 1979; 30(119-34.
34. Honn, K. V.; Timár, J.; Rozhin, J.; Bazaz, R.; Sameni, M.; Ziegler, G.; Sloane, B. A lipoxygenase metabolite, 12-(S)-HETE, stimulates protein kinase C-mediated release of cathepsin B from malignant cells. Exp. Cell. Res. 1994, 214, 120-130.
35. Hoobler, E. K.; Holz, C.; Holman, T. R. Pseudoperoxidase investigations of hydroperoxides and inhibitors with human lipoxygenases. Bioorg. Med. Chem. 2013, 21, 3894-3899.
36. Ikei, K. N.; Yeung, J.; Apopa, P. L.; Ceja, J.; Vesci, J.; Holman, T. R., Holinstat, M. Investigations of human platelet-type 12-Lipoxygenase:role of lipoxygenase products in platelet activation. J. Lipid Res. 2012, 53, 2546-2559.
37. Inglese, J.; Auld, D. S.; Jadhav, A.; Johnson, R. L.; Simeonov, A.; Yasgar, A.; Zheng, W.; Austin, C. P. Quantitative High-Throughput Screening: A Titration-Based Approach That Efficiently Identifies Biological Activities in Large Chemical Libraries. Proc. Natl. Acad. Sci. U.S.A. 2006, 103, 11473-11478.
38. Israels S J, McNicol A, Robertson C, and Gerrard J M. Platelet storage pool deficiency: diagnosis in patients with prolonged bleeding times and normal platelet aggregation. British journal of haematology. 1990; 75(1):118-21.
39. Jankun J, Aleem A M, Malgorzewicz S, Szkudlarek M, Zavodszky M I, Dewitt D L, Feig M, Selman S H, and Skrzypczak-Jankun E. Synthetic curcuminoids modulate the arachidonic acid metabolism of human platelet 12-lipoxygenase and reduce sprout formation of human endothelial cells. Molecular cancer therapeutics. 2006; 5(5):1371-82.
40. Kamitani, H.; Geller, M.; Eling, T. The possible involvement of 15-lipoxygenase/leukocyte type 12-lipoxygenase in colorectal carcinogenesis. Adv. Exp. Med. Biol. 1999, 469, 593-598.
41. Kandouz M, Nie D, Pidgeon G P, Krishnamoorthy S, Maddipati K R, and Honn K V. Platelet-type 12-lipoxygenase activates N F-kappaB in prostate cancer cells. Prostaglandins & other lipid mediators. 2003; 71(3-4): 189-204.
42. Kasirer-Friede A, Kahn M L, and Shattil S J. Platelet integrins and immunoreceptors. Immunological reviews. 2007; 218(247-64.
43. Katoh A, Ikeda H, Murohara T, Haramaki N, Ito H, and Imaizumi T. Platelet-derived 12-hydroxyeicosatetraenoic acid plays an important role in mediating canine coronary thrombosis by regulating platelet glycoprotein IIb/IIIa activation. Circulation. 1998; 98(25):2891-8.
44. Kenyon, V.; Chorny, I.; Carvajal, W. J.; Holman, T. R.; Jacobson, M. P. Novel human lipoxygenase inhibitors discovered using virtual screening with homology models. J. Med. Chem. 2006, 49, 1356-1363.
45. Kenyon, V.; Rai, G.; Jadhav, A.; Schultz, L.; Armstrong, M.; Jameson, B. A.; Perry, S.; Joshi, N.; Bougie, J. M.; Leister, W.; Taylor-Fishwick D. A.; Nadler, J. L.; Holinstat, M.; Simeonov, A.; Maloney, D. J.; Holman, T. R. Discovery of Potent and Selective Inhibitors of Human Platelet-Type 12-Lipoxygenase. J. Med. Chem. 2011, 54, 5485-5497.
46. Lee, Y. K.; Parks, D. J.; Lu, T.; Thieu, T. V.; Markotan, T.; Pan, W.; McComsey, D. F.; Milkiewicz, K. L.; Crysler, C. S.; Ninan, N.; Abad, M. C.; Giardino, E. C.; Maryanoff, B. E.; Damiano, B. P.; Player, M. R. J. Med. Chem. 2008, 51, 282-297.
47. Luci D K, Jameson J B, 2nd, Yasgar A, Diaz G, Joshi N, Kantz A, Markham K, Perry S, Kuhn N, Yeung J, et al. Synthesis and structure-activity relationship studies of 4-((2-hydroxy-3-methoxybenzyl)amino)benzenesulfonamide derivatives as potent and selective inhibitors of 12-lipoxygenase. Journal of medicinal chemistry. 2014; 57(2):495-506.
48. Ma, K.; Nunemaker, C. S.; Wu, R.; Chakrabarti, S. K.; Taylor-Fishwick, D. A.; Nadler, J. L. 12-Lipoxygenase Products Reduce Insulin Secretion and β-cell Viability in Human Islets. J. Clin. Endocrinol. Metab. 2010, 95, 887-893.
49. Madsen, P. et al. Optimization of Alkylidene Hydrazide Based Humna Glucagon Receptor Antagonists. Discovery of the Highly Potent and Orally Available 3-Cyano-4-hydroxybenzoic Acid [1-(2,3,5,6-Tetramethylbenzyl)-1H-indol-4-ylmethylene]hydrazide. J. Med. Chem. 2002, 45, 5755-5775.
50. Malterud, K. E.; Rydland, K. M. Inhibitors of 15-lipoxygenase from orange peel. J. Agric. Food Chem. 2000, 48, 5576-5580. (c) Moreau, R. A.; Agnew, J.; Hicks, K. B.; Powell, M. J. Modulation of lipoxygenase activity by bacterial hopanoids. J. Nat. Prod. 1997, 60, 397-398.
51. McDuffie, M.; Maybee, N. A.; Keller, S. R.; Stevens, B. K.; Garmey, J. C.; Morris, M. A.; Kropf, E.; Rival, C.; Ma, K.; Carter, J. D. Tersey, S. A.; Nunemaker, C. S.; Nadler, J. L. Nonobese diabetic (NOD) mice congenic for a targeted deletion of 12/15-Lipoxygenase are protected from autoimmune diabetes. Diabetes 2008, 57, 199-209.
52. McMahon G S, Jones C I, Hayes P D, Naylor A R, and Goodall A H. Transient heparin-induced platelet activation linked to generation of platelet 12-lipoxygenase. Findings from a randomised controlled trial. Thrombosis and haemostasis. 2013; 109(6):1099-107.
53. McNicol A, and Israels S J. Platelet dense granules: structure, function and implications for haemostasis. Thrombosis research. 1999; 95(1):1-18.
54. Morgan L T, Thomas C P, Kuhn H, and O'Donnell V B. Thrombin-activated human platelets acutely generate oxidized docosahexaenoic-acid-containing phospholipids via 12-lipoxygenase. The Biochemical journal. 2010; 431(1): 141-8.
55. Moroi M, Jung S M, Okuma M, and Shinmyozu K. A patient with platelets deficient in glycoprotein VI that lack both collagen-induced aggregation and adhesion. The Journal of clinical investigation. 1989; 84(5):1440-5.
56. Nakano, H., Inoue, T., Kawasaki, N., Miyataka, H., Matsumoto, H., Taguchi, T., Inagaki, N., Nagai, H., Satoh, T. Synthesis and Biological Activities of Novel Antiallergic Agents with 5-Lipoxygenase Inhibiting Action. Bioorg. Med. Chem. 2000, 8, 373-280.
57. Nappez, C.; Liagre, B.; Beneytout, J. L. Changes in lipoxygenase activities in human erythroleukemia (HEL) cells during diosgenin-induced differentiation. Cancer Lett. 1995, 96, 133-140.
58. Natarajan, R.; Esworthy, R.; Bai, W.; Gu, J. L.; Wilczynski, S.; Nadler, J. L. Increase 12-lipoxygenase expression in breast cancer cells and tissues. Regulation by epidermal growth factor. J. Clin. Endocrinol. Metab. 1997, 82, 1790-1798.

59. Nie D, Krishnamoorthy S, Jin R, Tang K, Chen Y, Qiao Y, Zacharek A, Guo Y, Milanini J, Pages G, et al. Mechanisms regulating tumor angiogenesis by 12-lipoxygenase in prostate cancer cells. The Journal of biological chemistry. 2006; 281(27):18601-9.

60. Nie, D.; Hillman, G. G.; Geddes, T.; Tang, K.; Pierson, C.; Grignon, D. J.; Honn, K. V. Platelet-type 12-lipoxygenase in a human prostate carcinoma stimulates angiogenesis and tumor growth. Cancer Res. 1998, 58, 4047-4051.

61. Nie, D.; Tang, K.; Diglio, C.; Honn, K. Eicosanoid regulation of angiogenesis: role of endothelial arachidonate 12-lipoxygenase. Blood 2000, 95, 2304-2311.

62. Nyby, M. D.; Sasaki, M.; Ideguchi, Y.; Wynne, H. E.; Hori, M. T.; Berger, M. E.; Golub, M. S.; Brickman, A. S.; Tuck, M. L. Platelet lipoxygenase inhibitors attenuate thrombin- and thromboxane mimetic-induced intracellular calcium mobilization and platelet aggregation. J. Pharmacol. Exp. Ther. 1996, 278, 503-509.

63. Ohri, R. V.; Radosevich, A. T.; Hrovat, K. J.; Musich, C.; Huang, D.; Holman, T. R.; Toste, F. D. A Re(V)-catalyzed C—N bond-forming route to human lipoxygenase inhibitors, Org. lett. 2005, 7, 2501-2504.

64. Phillips D R, and Agin P P. Platelet membrane defects in Glanzmann's thrombasthenia. Evidence for decreased amounts of two major glycoproteins. The Journal of clinical investigation. 1977; 60(3):535-45.

65. Pratico, D.; Zhukareva, V.; Yao, Y.; Uryu, K.; Funk, C. D.; Lawson, J. A.; Trojanowski, J. Q.; Lee, V. M. 12/15-Lipoxygenase is increased in Alzheimer's disease: possible involvement in brain oxidative stress. Am. J. Pathol. 2004, 164, 1655-1662.

66. Radmark, O., Samuelsson, B. 5-Lipoxygenase: Regulation and Possible Involvement in Atherosclerosis. Prostaglandins Other Lipid Mediat. 2007, 83, 162-174.

67. Reilly M P, Sinha U, Andre P, Taylor S M, Pak Y, Deguzman F R, Nanda N, Pandey A, Stolla M, Bergmeier W, et al. PRT-060318, a novel Syk inhibitor, prevents heparin-induced thrombocytopenia and thrombosis in a transgenic mouse model. Blood. 2011; 117(7):2241-6.

68. Robinson, S. J.; Hoobler, E. K.; Riener, M.; Loveridge, S. T.; Tenney, K.; Valeriote, F. A.; Holman, T. R.; Crews, P. Using enzyme assays to evaluate the structure and bioactivity of sponge-derived meroterpenes. J. Nat. Prod. 2009, 72, 1857-1863.

69. Rosenfeld S I, Looney R J, Leddy J P, Phipps D C, Abraham G N, and Anderson C L. Human platelet Fc receptor for immunoglobulin G. Identification as a 40,000-molecular-weight membrane protein shared by monocytes. The Journal of clinical investigation. 1985; 76(6):2317-22.

70. Sailer, E. R.; Schweizer, S.; Boden, S. E.; Ammon, H. P. T.; Safayhi, H. Characterization of an acetyl-11-keto-B-boswellic acid and arachidonate-binding regulatory site of 5-lipoxygenase using photoaffinity labeling. Eur. J. Biochem. 1998, 256, 364-368.

71. Segraves, E. N.; Shah, R. R.; Segraves, N. L.; Johnson, T. A.; Whitman, S.; Sui, J. K.; Kenyon, V. A.; Cichewicz, R. H.; Crews, P.; Holman, T. R. Probing the activity differences of simple and complex brominated aryl compounds against 15-soybean, 15-human, and 12-human lipoxygenase. J. Med. Chem. 2004, 47, 4060-4065.

72. Serhan, C. N.; Petasis, N. A. Resolvins and Protectins in Inflammation Resolution. Chem. Rev. 2011, 111, 5922-5943.

73. Solomon, E. I.; Zhou, J.; Neese, F.; Pavel, E. G. New insights from spectroscopy into the structure/function relationships of lipoxygenases. Chem. Biol. 1997, 4, 795-808. (b) Brash, A. R. Lipoxygenases: Occurrence, Functions, Catalysis and Acquisition of Substrate. J. Biol. Chem. 1999, 274, 23679-23682.

74. Soriano, A. F.; Helfrich, B.; Chan, D. C.; Heasley, L. E.; Bunn, P. A.; Chou, T. C. Synergistic effects of new chemopreventive agents and conventional cytotoxic agents against human lung cancer cell lines. Cancer Res. 1999, 59, 6178-6184.

75. Strehl A, Munnix I C, Kuijpers M J, van der Meijden P E, Cosemans J M, Feijge M A, Nieswandt B, and Heemskerk J W. Dual role of platelet protein kinase C in thrombus formation: stimulation of pro-aggregatory and suppression of procoagulant activity in platelets. The Journal of biological chemistry. 2007; 282(10):7046-55.

76. Sugiyama T, Okuma M, Ushikubi F, Sensaki S, Kanaji K, and Uchino H. A novel platelet aggregating factor found in a patient with defective collagen-induced platelet aggregation and autoimmune thrombocytopenia. Blood. 1987; 69(6):1712-20.

77. Suzuki-Inoue K, Fuller G L, Garcia A, Eble J A, Pohlmann S, Inoue O, Gartner T K, Hughan S C, Pearce A C, Laing G D, et al. A novel Syk-dependent mechanism of platelet activation by the C-type lectin receptor CLEC-2. Blood. 2006; 107(2):542-9.

78. Suzuki-Inoue K, Inoue O, and Ozaki Y. Novel platelet activation receptor CLEC-2: from discovery to prospects. Journal of thrombosis and haemostasis: JTH. 2011; 9 Suppl 1(44-55)

79. Takai T. Roles of Fc receptors in autoimmunity. Nature reviews Immunology. 2002; 2(8):580-92.

80. Thomas C P, Morgan L T, Maskrey B H, Murphy R C, Kuhn H, Hazen S L, Goodall A H, Hamali H A, Collins P W, and O'Donnell V B. Phospholipid-esterified eicosanoids are generated in agonist-activated human platelets and enhance tissue factor-dependent thrombin generation. The Journal of biological chemistry. 2010; 285 (10): 6891-903.

81. Thomas, C. P.; Morgan, L. T.; Maskrey, B. H.; Murphy, R. C; Kuhn, H.; Hazen, S. L.; Goodall, A. H.; Hamali, H. A.; Collins, P. W.; O'Donnell, V. D. Phospholipid-esterified eicosanoids are generated in agonist-activated human platelets and enhance tissue factor-dependant thrombin generation. J. Biol. Chem. 2010, 285, 6891-6903.

82. Timár, J.; Silletti, S.; Bazaz, R.; Raz, A.; Honn, K. V. Regulation of melanoma-cell motility by the lipoxygenase metabolite 12-(S)-HETE. Int. J. Cancer, 1993, 55, 1003-1010.

83. Tsuji M, Ezumi Y, Arai M, and Takayama H. A novel association of Fc receptor gamma-chain with glycoprotein VI and their co-expression as a collagen receptor in human platelets. The Journal of biological chemistry. 1997; 272(38):23528-31.

84. van Leyen, K.; Arai, K.; Jin, G.; Kenyon, V.; Gerstner, B.; Rosenberg, P. A.; Holman, T. R.; Lo, E. H. Novel lipoxygenase inhibitors as neuroprotective reagents. J. Neurosci. Res. 2008, 86, 904-909.

85. van Leyen, K.; Kim, H. Y.; Lee, S. R.; Jin, G.; Arai, K.; Lo, E. H. Baicalein and 12/15-lipoxygenase in the ischemic brain. Stroke. 2006, 37, 3014-3018.

86. Vasquez-Martinez, Y.; Ohri, R. V.; Kenyon, V.; Holman, T. R.; Sepulveda-Boza, S. Structure-activity relationship studies of flavonoids as potent inhibitors of human platelet 12-hLO, reticulocyte 15-hLO-1, and prostate epithelial 15-hLO-2. Bioorg. Med. Chem. 2007, 15, 7408-7425.
87. Wang, X.; Guram, A.; Ronk, M.; Milne, J. E.; Tedrow, J. S.; Faul, M. M. Copper-catalyzed N-arylation of sulfonamides with aryl bromides. Tetrahedron Lett. 2012, 53, 7-10.
88. Watanabe N, Bodin L, Pandey M, Krause M, Coughlin S, Boussiotis V A, Ginsberg M H, and Shattil S J. Mechanisms and consequences of agonist-induced talin recruitment to platelet integrin alphaIIbbeta3. The Journal of cell biology. 2008; 181(7):1211-22.
89. Whitman, S.; Gezginci, M.; Timmermann, B. N.; Holman, T. R. Structure-activity relationship studies of nordihydroguaiaretic acid inhibitors toward soybean, 12-human, and 15-human lipoxygenase. J. Med. Chem. 2002, 45, 2659-2661.
90. Yacoub D, Theoret J F, Villeneuve L, Abou-Saleh H, Mourad W, Allen B G, and Merhi Y. Essential role of protein kinase C delta in platelet signaling, alpha IIb beta 3 activation, and thromboxane A2 release. The Journal of biological chemistry. 2006; 281(40):30024-35.
91. Yamamoto, S. Mammalian lipoxygenases: Molecular Structures and functions. Biochim. Biophys. Acta. 1992, 1128, 117-131. (b) Funk, C. D.; Keeney, D. S.; Oliw, E. H.; Vogel, S.; Muller-Decker, K.; Mincheva, A.; Lichter, P.; Marks, F.; Krieg, P. Murine epidermal lipoxygenase (Aloxe) encodes a 12-lipoxygenase isoform. FEBS Lett. 1997, 402, 162-166.
92. Yanaga F, Poole A, Asselin J, Blake R, Schieven G L, Clark E A, Law C L, and Watson S P. Syk interacts with tyrosine-phosphorylated proteins in human platelets activated by collagen and cross-linking of the Fc gamma-IIA receptor. The Biochemical journal. 1995; 311 (Pt 2)(471-8.
93. Yeung J, Apopa P L, Vesci J, Stolla M, Rai G, Simeonov A, Jadhav A, Fernandez-Perez P, Maloney D J, Boutaud O, et al. 12-lipoxygenase activity plays an important role in PAR4 and GPVI-mediated platelet reactivity. Thrombosis and haemostasis. 2013; 110(3):569-81.
94. Yeung, J.; Apopa, P. L.; Vesci, J.; Kenyon, V.; Rai, G.; Jadhav, A.; Simeonov, A.; Holman, T. R.; Maloney, D. J.; Boutaud, O.; Holinstat. Protein Kinase C Regulation of 12-Lipoxygenase-Mediated Human Platelet Activation. Mol. Pharmacol. 2012, 81, 420-430.
95. Zhi H, Rauova L, Hayes V, Gao C, Boylan B, Newman D K, McKenzie S E, Cooley B C, Poncz M, and Newman P J. Cooperative integrin/ITAM signaling in platelets enhances thrombus formation in vitro and in vivo. Blood. 2013; 121(10):1858-67.

The invention claimed is:
1. A compound that is

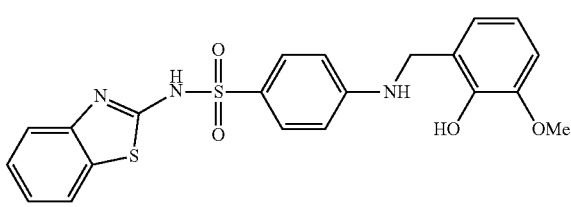

or a pharmaceutically acceptable salt thereof.

2. A compound that is

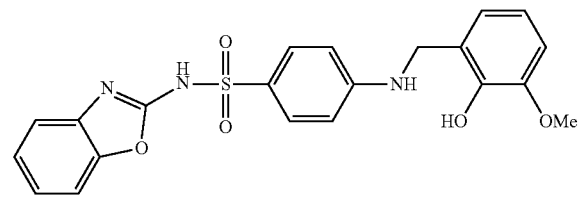 [SMILES: COc1cccc(CNc2ccc(S(=O)(=O)Nc3nc4ccccc4s3)cc2)c1O]

or a pharmaceutically acceptable salt thereof.

3. A compound that is

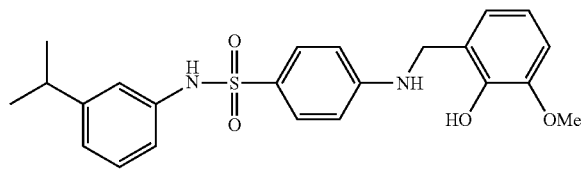

or a pharmaceutically acceptable salt thereof.

4. A compound of Formula (I)

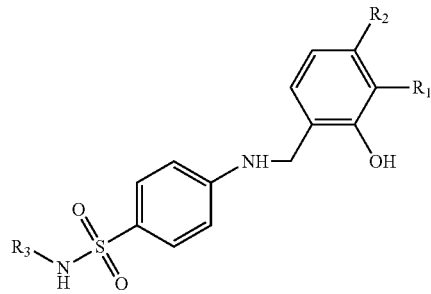

wherein $R_1$ is methoxy;
$R_2$ is H; and
$R_3$ is selected from the group consisting of 2-benzothiazole, 4-methyl-2-benzothiazole, 6-fluoro-2-benzothiazole, 6-methoxy-2-benzothiazole, 2-benzoxazole, 2-benzimidazole, 2-thiophene, 4-methyl-2-thiazole, 5-methyl-2-thiazole, 4,5-methyl-2-thiazole, 4-phenyl-2-thiazole, 3-quinoline, 8-isoquinoline, phenyl, 1,4-biphenyl, 1-naphthalene, 2-naphthalene, 3-piperazine-phenyl, 4-piperidine-phenyl, 3-piperidine-phenyl, 2-pyridine, 3-pyridine, 4-piperazine-3-pyridine, 3-tert-butyl-phenyl, 3-morpholine-phenyl, 4N-boc-piperidine-3-phenyl, and 3-isopropyl-phenyl.

5. The compound of claim 4, wherein $R_3$ is selected from the group consisting of 2-benzothiazole, 4-methyl-2-benzothiazole, 6-methoxy-2-benzothiazole, 2-benzoxazole, 2-benzimidazole, 2-thiophene, 4-phenyl-2-thiazole, 3-quinoline, 8-isoquinoline, phenyl, 1-napthalene, 2-napthalene, 3-tert-butyl-phenyl, 4N-boc-piperidine-3-phenyl, and 3-isopropyl-phenyl.

6. A compound of Formula (I)

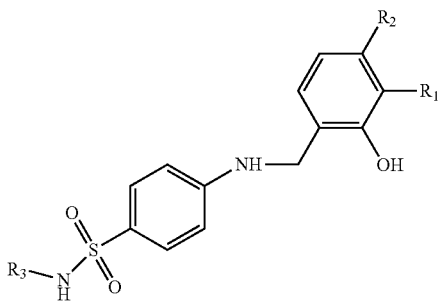

wherein $R_1$ is Cl or H, and $R_2$ is Br or H, wherein when $R_1$ is Cl, $R_2$ is H, and when $R_1$ is H, $R_2$ is Br; and $R_3$ is selected from the group consisting of phenyl, 4-biphenyl, thiazole, 1-napthalene, 2-napthalene, 2-benzothiazole, 3-quinoline, 8-isoquinoline, and 4-phenyl-piperidine, wherein when $R_3$ is 4-phenyl-piperidine, $R_1$ is Cl and $R_2$ is H.

7. The compound of claim 6, wherein $R_3$ is selected from the group consisting of 1-napthalene, 2-benzothiazole, 2-napthalene.

8. A method for treating or preventing thrombosis, comprising administering to a mammal thereof a therapeutically or prophylactically effective amount of a compound of claim 4, or salt thereof.

9. A method for treating or preventing thrombosis comprising administering to a mammal thereof a therapeutically or prophylactically effective amount of a compound of claim 6, or salt thereof.

* * * * *

UNITED STATES PATENT AND TRADEMARK OFFICE
CERTIFICATE OF CORRECTION

PATENT NO. : 10,266,488 B2
APPLICATION NO. : 15/028386
DATED : April 23, 2019
INVENTOR(S) : David J. Maloney et al.

Page 1 of 1

It is certified that error appears in the above-identified patent and that said Letters Patent is hereby corrected as shown below:

In the Specification

In Column 1, Lines 21-34, please delete:
"This invention was made with government support under the intramural research program of the National Center forAdvancing Translational Sciences and the Molecular Libraries Initiative of the National Institutes of Health Roadmap for Medical Research grant no. U54MH084681, the National Institute of Health grant no. R01 GM56062, the Molecular Libraries Initiative of the National Institutes of Health Roadmap for Medical Research grant no. R03 MH081283, NIH grant no. S10 - RR20939, the National Heart, Lung, and Blood Institute ( NHLBI ) grant no. HL114405 and the National Institute of General Medical Sciences ( NIGMS ) grant no. GM105671. The government has certain rights in the invention."

And insert:
--This invention was made with government support under MH084681, GM056062, MH081283, RR020939, HL114405, and GM105671 awarded by the National Institutes of Health. The government has certain rights in the invention.--

Signed and Sealed this
Fourth Day of May, 2021

Drew Hirshfeld
*Performing the Functions and Duties of the
Under Secretary of Commerce for Intellectual Property and
Director of the United States Patent and Trademark Office*